(12) United States Patent
Luettgen

(10) Patent No.: US 10,016,254 B2
(45) Date of Patent: Jul. 10, 2018

(54) DENTAL WATER JET

(71) Applicant: WATER PIK, INC., Fort Collins, CO (US)

(72) Inventor: Harold A. Luettgen, Windsor, CO (US)

(73) Assignee: Water Pik, Inc., Fort Collins, CO (US)

( * ) Notice: Subject to any disclaimer, the term of this patent is extended or adjusted under 35 U.S.C. 154(b) by 756 days.

(21) Appl. No.: 14/579,652

(22) Filed: Dec. 22, 2014

(65) Prior Publication Data

US 2015/0173850 A1     Jun. 25, 2015

Related U.S. Application Data

(60) Provisional application No. 61/919,511, filed on Dec. 20, 2013.

(51) Int. Cl.
*A61C 17/02* (2006.01)
*A61C 1/00* (2006.01)

(52) U.S. Cl.
CPC ........ *A61C 1/0092* (2013.01); *A61C 17/0202* (2013.01); *A61C 17/0205* (2013.01)

(58) Field of Classification Search
CPC ..... A61C 1/0084; A61C 1/0092; A61C 17/02; A61C 17/0202; A61H 13/005; A61M 3/0258; A61M 3/0279
See application file for complete search history.

(56) References Cited

U.S. PATENT DOCUMENTS

| 555,588 A | 3/1896 | Spencer |
|---|---|---|
| 1,278,225 A | 9/1918 | Schamberg |
| 1,452,258 A | 4/1923 | Smith |
| 1,464,419 A | 8/1923 | Gill |
| 1,480,310 A | 1/1924 | Smith |
| 1,498,267 A | 6/1924 | Hachman |
| 1,602,742 A * | 10/1926 | Bennett ................... A47L 15/39 15/75 |
| 1,650,686 A | 11/1927 | Binks |
| 1,669,889 A | 5/1928 | Andrews et al. |
| 1,681,320 A | 8/1928 | Bergl et al. |

(Continued)

FOREIGN PATENT DOCUMENTS

| CA | 851479 | 9/1970 |
|---|---|---|
| CH | 655237 | 4/1987 |

(Continued)

OTHER PUBLICATIONS

US RE27,274, 01/1972, Mattingly (withdrawn)

(Continued)

*Primary Examiner* — Justine Yu
*Assistant Examiner* — Christopher Miller
(74) *Attorney, Agent, or Firm* — Dorsey & Whitney LLP

(57) ABSTRACT

A dental water jet provides a pressurized water stream for cleaning gums and teeth. The embodiment includes a base unit defining a cavity. The cavity contains a pump, which may move pressurized water from a reservoir to a tip in fluid communication with the pump. A flow control knob may be turned to selectively adjust the water pressure supplied by the tip between a minimum and a maximum value. Fluid may flow from the reservoir and ultimately into the tip to provide oral irrigation and/or cleaning of the teeth, gums, and tongue.

25 Claims, 30 Drawing Sheets

(56) References Cited

U.S. PATENT DOCUMENTS

| | | |
|---|---|---|
| 1,933,454 A | 10/1933 | Sidney |
| 1,940,111 A | 12/1933 | Austin |
| D93,019 S | 8/1934 | Hose |
| 1,977,782 A | 10/1934 | Roy |
| 2,107,686 A | 2/1938 | Bramsen et al. |
| 2,421,498 A * | 6/1947 | Guedel ............... A61C 17/00 29/DIG. 101 |
| D159,872 S | 8/1950 | Skold |
| 2,531,730 A | 11/1950 | Henderson |
| 2,595,666 A | 5/1952 | Hutson |
| 2,669,233 A | 2/1954 | Friend |
| 2,709,227 A | 5/1955 | Foley et al. |
| 2,733,713 A * | 2/1956 | Kabnick ............ A61H 13/005 601/162 |
| 2,783,919 A | 3/1957 | Ansell |
| 2,794,437 A | 6/1957 | Tash |
| 2,870,932 A | 1/1959 | Davis |
| 2,984,452 A | 5/1961 | Hooper |
| 3,089,490 A | 5/1963 | Goldberg |
| 3,096,913 A | 7/1963 | Jousson |
| 3,144,867 A | 8/1964 | Trupp et al. |
| D202,041 S | 8/1965 | Burzlaff |
| 3,209,956 A | 10/1965 | McKenzie |
| 3,216,619 A | 11/1965 | Richards et al. |
| 3,225,759 A | 12/1965 | Drapen et al. |
| 3,227,158 A | 1/1966 | Mattingly |
| 3,266,623 A | 8/1966 | Poferl |
| 3,297,558 A | 1/1967 | Hillquist |
| D208,778 S | 10/1967 | Koch |
| D209,204 S | 11/1967 | St. Clair et al. |
| D209,395 S | 11/1967 | Gilbert |
| D210,018 S | 1/1968 | Mattingly et al. |
| D210,019 S | 1/1968 | Johnson et al. |
| 3,370,214 A | 2/1968 | Aymar |
| 3,391,696 A | 7/1968 | Woodward |
| 3,393,673 A * | 7/1968 | Mattingly ............ A61C 1/0092 417/415 |
| 3,400,999 A | 9/1968 | Goldstein |
| 3,418,552 A | 12/1968 | Holmes |
| 3,420,228 A | 1/1969 | Kalbfeld |
| 3,425,410 A | 2/1969 | Cammack |
| 3,453,969 A | 7/1969 | Mattingly |
| 3,465,751 A | 9/1969 | Powers |
| 3,467,083 A | 9/1969 | Mattingly |
| 3,467,286 A * | 9/1969 | Ostrowsky ............ A61C 17/02 137/209 |
| D215,920 S | 11/1969 | McCarty et al. |
| 3,487,828 A | 1/1970 | Troy |
| 3,489,268 A | 1/1970 | Meierhoefer |
| 3,495,587 A | 2/1970 | Freedman |
| 3,496,933 A | 2/1970 | Lloyd |
| 3,499,440 A | 3/1970 | Gibbs |
| 3,500,824 A | 3/1970 | Gilbert |
| 3,501,203 A | 3/1970 | Falk |
| 3,502,072 A | 3/1970 | Stillman |
| 3,517,669 A | 6/1970 | Buono et al. |
| D218,270 S | 8/1970 | Soper |
| 3,522,801 A | 8/1970 | Robinson |
| 3,532,221 A | 10/1970 | Kaluhiokalani et al. |
| 3,536,065 A | 10/1970 | Moret |
| 3,537,444 A | 11/1970 | Garn |
| 3,538,950 A | 11/1970 | Porteners |
| 3,547,110 A | 12/1970 | Balamuth |
| 3,561,433 A | 2/1971 | Kovach |
| D220,334 S | 3/1971 | Mackay et al. |
| 3,570,525 A | 3/1971 | Borsum |
| 3,572,375 A | 3/1971 | Rosenberg |
| 3,578,884 A | 5/1971 | Jacobson |
| D220,996 S | 6/1971 | Irons |
| 3,583,609 A | 6/1971 | Oppenheimer |
| 3,590,813 A * | 7/1971 | Roszyk ............... A61C 1/0092 222/318 |
| 3,608,548 A | 9/1971 | Lewis |
| 3,612,045 A * | 10/1971 | Dudas ............... A61C 17/0214 601/162 |
| D222,862 S | 1/1972 | Cook |
| 3,636,947 A | 1/1972 | Balamuth |
| 3,651,576 A | 3/1972 | Massa |
| 3,669,101 A | 6/1972 | Kleiner |
| 3,703,170 A | 11/1972 | Ryckman, Jr. |
| 3,718,974 A * | 3/1973 | Buchtel ............... A61C 1/0007 433/27 |
| 3,747,595 A | 7/1973 | Grossan |
| 3,768,472 A | 10/1973 | Hodosh et al. |
| 3,771,186 A * | 11/1973 | Moret ............... A61C 17/028 15/22.1 |
| 3,783,364 A | 1/1974 | Gallanis et al. |
| 3,809,506 A | 5/1974 | Malcosky |
| 3,809,977 A | 5/1974 | Balamuth et al. |
| 3,811,432 A | 5/1974 | Moret |
| 3,820,532 A | 6/1974 | Eberhardt et al. |
| 3,827,147 A | 8/1974 | Condon |
| 3,837,166 A | 9/1974 | Hiraoka |
| 3,840,795 A | 10/1974 | Roszyk et al. |
| 3,847,145 A | 11/1974 | Grossan |
| 3,854,209 A | 12/1974 | Franklin et al. |
| 3,863,628 A | 2/1975 | Vit |
| 3,871,560 A | 3/1975 | Crippa |
| 3,874,506 A | 4/1975 | Hill et al. |
| 3,912,125 A | 10/1975 | Acklin |
| 3,943,628 A | 3/1976 | Kronman et al. |
| 3,959,883 A | 6/1976 | Walls et al. |
| 3,973,558 A | 8/1976 | Stouffer et al. |
| 3,977,084 A * | 8/1976 | Sloan ............... A61C 17/005 15/29 |
| 4,001,526 A | 1/1977 | Olson |
| 4,004,302 A | 1/1977 | Hori |
| 4,007,739 A | 2/1977 | Bron et al. |
| 4,013,227 A | 3/1977 | Herrera |
| 4,052,002 A | 10/1977 | Stouffer et al. |
| D246,667 S | 12/1977 | Mackay et al. |
| D246,668 S | 12/1977 | Mackay et al. |
| 4,060,870 A | 12/1977 | Cannarella |
| 4,075,761 A | 2/1978 | Behne et al. |
| 4,078,558 A | 3/1978 | Woog et al. |
| 4,089,079 A | 5/1978 | Nicholson |
| 4,094,311 A | 6/1978 | Hudson |
| 4,108,167 A | 8/1978 | Hickman et al. |
| 4,108,178 A | 8/1978 | Betush |
| 4,109,650 A | 8/1978 | Peclard |
| 4,122,845 A | 10/1978 | Stouffer et al. |
| 4,133,971 A * | 1/1979 | Boyd ............... A47L 9/2842 15/DIG. 10 |
| 4,135,501 A | 1/1979 | Leunissan |
| 4,141,352 A | 2/1979 | Ebner et al. |
| 4,144,646 A | 3/1979 | Takemoto et al. |
| 4,149,315 A | 4/1979 | Page, Jr. et al. |
| 4,154,375 A | 5/1979 | Bippus |
| 4,160,383 A | 7/1979 | Rauschenberger |
| 4,171,572 A | 10/1979 | Nash |
| 4,182,038 A | 1/1980 | Fleer |
| 4,200,235 A | 4/1980 | Monschke |
| 4,201,200 A | 5/1980 | Hubner |
| 4,210,380 A * | 7/1980 | Brzostek ............ H01R 13/5833 439/456 |
| 4,215,476 A | 8/1980 | Armstrong |
| 4,219,618 A | 8/1980 | Leonard |
| 4,227,878 A | 10/1980 | Lohn |
| 4,229,634 A | 10/1980 | Hickman et al. |
| 4,236,889 A | 12/1980 | Wright |
| D258,097 S | 2/1981 | Wistrand |
| 4,248,589 A | 2/1981 | Lewis |
| 4,249,899 A | 2/1981 | Davis |
| 4,257,458 A | 3/1981 | Kondo et al. |
| 4,262,799 A | 4/1981 | Perrett |
| 4,266,934 A | 5/1981 | Pernot |
| 4,276,023 A | 6/1981 | Phillips et al. |
| 4,276,880 A | 7/1981 | Malmin |
| 4,302,186 A | 11/1981 | Cammack et al. |
| 4,303,064 A | 12/1981 | Buffa |
| 4,303,070 A | 12/1981 | Ichikawa et al. |
| 4,306,862 A | 12/1981 | Knox |

(56) References Cited

U.S. PATENT DOCUMENTS

| | | |
|---|---|---|
| 4,315,741 A | 2/1982 | Reichl |
| 4,319,568 A | 3/1982 | Tregoning |
| 4,331,422 A | 5/1982 | Heyman |
| 4,337,040 A | 6/1982 | Cammack et al. |
| 4,340,365 A | 7/1982 | Pisanu |
| 4,340,368 A | 7/1982 | Lococo |
| D266,117 S | 9/1982 | Oberheim |
| 4,353,694 A | 10/1982 | Pelerin |
| 4,363,626 A | 12/1982 | Schmidt et al. |
| 4,365,376 A | 12/1982 | Oda et al. |
| 4,370,131 A | 1/1983 | Banko |
| 4,374,354 A | 2/1983 | Petrovic et al. |
| 4,382,167 A | 5/1983 | Maruyama et al. |
| 4,382,786 A | 5/1983 | Lohn |
| D270,000 S | 8/1983 | Ketler |
| 4,396,011 A * | 8/1983 | Mack e .......... A61H 23/02 128/DIG. 15 |
| 4,412,823 A | 11/1983 | Sakai et al. |
| 4,416,628 A | 11/1983 | Cammack |
| 4,442,830 A | 4/1984 | Markau |
| 4,442,831 A | 4/1984 | Trenary |
| 4,452,238 A | 6/1984 | Kerr |
| 4,454,866 A | 6/1984 | Fayen |
| 4,512,769 A | 4/1985 | Kozam et al. |
| 4,517,962 A | 5/1985 | Heckele |
| 4,531,912 A | 7/1985 | Schuss et al. |
| 4,531,913 A | 7/1985 | Taguchi |
| 4,534,340 A | 8/1985 | Kerr et al. |
| 4,552,130 A | 11/1985 | Kinoshita |
| 4,561,214 A | 12/1985 | Inoue |
| D283,374 S | 4/1986 | Cheuk-Yiu |
| 4,585,415 A | 4/1986 | Hommann |
| 4,591,777 A | 5/1986 | McCarty et al. |
| 4,592,728 A | 6/1986 | Davis |
| 4,602,906 A | 7/1986 | Grunenfelder |
| 4,607,627 A | 8/1986 | Leber et al. |
| 4,613,074 A | 9/1986 | Schulze |
| 4,619,009 A | 10/1986 | Rosenstatter |
| 4,619,612 A | 10/1986 | Weber et al. |
| 4,629,425 A | 12/1986 | Detsch |
| 4,636,198 A | 1/1987 | Stade |
| 4,642,037 A | 2/1987 | Fritchman |
| 4,644,937 A * | 2/1987 | Hommann .......... A61C 17/02 433/80 |
| 4,645,488 A | 2/1987 | Matukas |
| 4,647,831 A | 3/1987 | O'Malley et al. |
| 4,648,838 A | 3/1987 | Schlachter |
| 4,650,475 A | 3/1987 | Smith et al. |
| 4,655,198 A | 4/1987 | Hommann |
| 4,669,453 A | 6/1987 | Atkinson et al. |
| 4,672,953 A | 6/1987 | DiVito |
| 4,673,396 A | 6/1987 | Urbaniak |
| D291,354 S | 8/1987 | Camens |
| 4,716,352 A | 12/1987 | Hurn et al. |
| 4,749,340 A | 6/1988 | Ikeda et al. |
| 4,770,632 A * | 9/1988 | Ryder .......... A61C 1/0092 433/101 |
| D298,565 S | 11/1988 | Kohler, Jr. et al. |
| 4,783,321 A | 11/1988 | Spence |
| 4,787,845 A | 11/1988 | Valentine |
| 4,787,847 A | 11/1988 | Martin et al. |
| 4,798,292 A | 1/1989 | Hauze |
| 4,803,974 A * | 2/1989 | Powell .......... A61C 17/02 206/368 |
| 4,804,364 A | 2/1989 | Dieras et al. |
| 4,810,148 A * | 3/1989 | Aisa .......... B03C 1/286 252/62.54 |
| 4,818,229 A | 4/1989 | Vasile |
| 4,820,152 A | 4/1989 | Warrin et al. |
| 4,821,923 A | 4/1989 | Skorka |
| 4,824,368 A | 4/1989 | Hickman |
| 4,826,431 A | 5/1989 | Fujimura et al. |
| 4,827,551 A | 5/1989 | Maser et al. |
| 4,832,683 A | 5/1989 | Idemoto et al. |
| 4,854,869 A | 8/1989 | Lawhorn |
| 4,861,340 A | 8/1989 | Smith et al. |
| 4,862,876 A | 9/1989 | Lih-Sheng |
| 4,869,720 A | 9/1989 | Chernack |
| 4,880,382 A | 11/1989 | Moret et al. |
| 4,886,452 A | 12/1989 | Lohn |
| 4,900,252 A | 2/1990 | Liefke et al. |
| 4,902,225 A | 2/1990 | Lohn |
| 4,903,687 A | 2/1990 | Lih-Sheng |
| 4,906,187 A | 3/1990 | Amadera |
| 4,907,744 A | 3/1990 | Jousson |
| 4,925,450 A | 5/1990 | Imonti et al. |
| 4,928,675 A | 5/1990 | Thornton |
| 4,930,660 A | 6/1990 | Porteous |
| 4,941,459 A | 7/1990 | Mathur |
| 4,950,159 A | 8/1990 | Hansen |
| 4,958,629 A * | 9/1990 | Peace .......... A61H 9/00 601/165 |
| 4,958,751 A | 9/1990 | Curtis et al. |
| 4,959,199 A | 9/1990 | Brewer |
| 4,961,698 A | 10/1990 | Vlock |
| 4,966,551 A | 10/1990 | Betush |
| 4,969,874 A | 11/1990 | Michel et al. |
| 4,973,246 A | 11/1990 | Black |
| 4,973,247 A | 11/1990 | Varnes et al. |
| 4,973,250 A | 11/1990 | Milman |
| 4,975,054 A | 12/1990 | Esrock |
| 4,979,503 A | 12/1990 | Chernack |
| 4,979,504 A | 12/1990 | Mills |
| 4,989,590 A | 2/1991 | Baum et al. |
| 4,998,880 A | 3/1991 | Nerli |
| 5,013,241 A | 5/1991 | Von Gutfeld et al. |
| 5,019,054 A | 5/1991 | Clement et al. |
| 5,014,884 A | 6/1991 | Wunsch |
| 5,027,798 A | 7/1991 | Primiano |
| 5,029,576 A | 7/1991 | Evans, Sr. |
| 5,033,617 A | 7/1991 | Hartwein et al. |
| 5,033,961 A | 7/1991 | Kankler et al. |
| D318,918 S | 8/1991 | Hartwein |
| 5,046,486 A | 9/1991 | Grulke et al. |
| 5,049,071 A | 9/1991 | Davis et al. |
| 5,060,825 A | 10/1991 | Palmer et al. |
| 5,061,180 A | 10/1991 | Wiele |
| 5,062,795 A | 11/1991 | Woog |
| 5,064,168 A | 11/1991 | Raines et al. |
| D322,314 S | 12/1991 | Ohbayashi |
| 5,071,346 A | 12/1991 | Domaas |
| 5,082,115 A | 1/1992 | Hutcheson |
| 5,082,443 A | 1/1992 | Lohn |
| 5,085,317 A | 2/1992 | Jensen et al. |
| 5,086,756 A | 2/1992 | Powell |
| 5,095,893 A | 3/1992 | Rawden, Jr. |
| 5,098,291 A | 3/1992 | Curtis et al. |
| 5,098,676 A | 3/1992 | Brooks, Jr. |
| 5,100,319 A | 3/1992 | Baum |
| 5,117,871 A | 6/1992 | Gardner et al. |
| 5,125,835 A | 6/1992 | Young |
| 5,127,831 A | 7/1992 | Bab |
| 5,142,723 A | 9/1992 | Lustig et al. |
| 5,150,841 A | 9/1992 | Silvenis et al. |
| 5,172,810 A | 12/1992 | Brewer |
| 5,173,273 A | 12/1992 | Brewer |
| 5,183,035 A | 2/1993 | Weir |
| 5,197,458 A | 3/1993 | Ito et al. |
| 5,197,460 A | 3/1993 | Ito et al. |
| 5,199,871 A | 4/1993 | Young |
| 5,203,697 A | 4/1993 | Malmin |
| 5,203,769 A | 4/1993 | Clement et al. |
| 5,204,004 A | 4/1993 | Johnston et al. |
| 5,208,933 A | 5/1993 | Lustig et al. |
| 5,215,193 A | 6/1993 | Dennis |
| 5,218,956 A | 6/1993 | Handler et al. |
| 5,220,914 A | 6/1993 | Thompson |
| 5,228,646 A | 7/1993 | Raines |
| 5,230,624 A | 7/1993 | Wolf et al. |
| 5,232,687 A | 8/1993 | Geimer |
| 5,235,968 A | 8/1993 | Woog |
| 5,241,714 A | 9/1993 | Barry |
| 5,246,367 A | 9/1993 | Ito et al. |

(56) References Cited

U.S. PATENT DOCUMENTS

| | | |
|---|---|---|
| 5,252,064 A | 10/1993 | Baum et al. |
| D341,200 S | 11/1993 | Yoshimoto |
| 5,257,933 A | 11/1993 | Jousson |
| 5,261,448 A | 11/1993 | Furuya et al. |
| D341,943 S | 12/1993 | Si-Hoe |
| 5,267,586 A | 12/1993 | Jankavaara |
| 5,269,684 A | 12/1993 | Fischer |
| 5,281,137 A | 1/1994 | Jousson |
| 5,281,139 A | 1/1994 | Frank et al. |
| 5,282,745 A | 2/1994 | Wiltrout et al. |
| 5,286,192 A | 2/1994 | Dixon |
| 5,286,201 A | 2/1994 | Yu |
| 5,295,832 A | 3/1994 | Evans |
| 5,297,962 A | 3/1994 | O'Connor et al. |
| D346,212 S | 4/1994 | Hosl |
| 5,301,381 A | 4/1994 | Klupt |
| 5,302,123 A | 4/1994 | Bechard |
| 5,317,691 A | 5/1994 | Traeger |
| 5,321,865 A | 6/1994 | Kaeser |
| 5,323,770 A * | 6/1994 | Ito .................... A61C 17/02 601/162 |
| 5,331,704 A | 7/1994 | Rosen et al. |
| 5,344,317 A | 9/1994 | Pacher et al. |
| 5,346,677 A | 9/1994 | Risk |
| D351,892 S | 10/1994 | Wolf et al. |
| 5,360,338 A | 11/1994 | Waggoner |
| 5,368,548 A | 11/1994 | Jousson |
| 5,370,534 A | 12/1994 | Wolf et al. |
| D354,168 S | 1/1995 | Hartwein |
| D354,559 S | 1/1995 | Knute |
| 5,378,149 A | 1/1995 | Stropko |
| 5,380,201 A | 1/1995 | Kawata |
| D356,864 S | 3/1995 | Woog |
| 5,399,089 A | 3/1995 | Eichman et al. |
| D358,883 S | 5/1995 | Vos |
| 5,456,672 A | 10/1995 | Diederich et al. |
| 5,465,445 A | 11/1995 | Yeh |
| 5,467,495 A | 11/1995 | Boland et al. |
| 5,468,148 A | 11/1995 | Ricks |
| 5,470,305 A | 11/1995 | Arnett et al. |
| 5,474,450 A | 12/1995 | Chronister |
| 5,474,451 A | 12/1995 | Dalrymple et al. |
| 5,476,379 A | 12/1995 | Disel |
| 5,484,281 A | 1/1996 | Renow et al. |
| 5,487,877 A | 1/1996 | Choi |
| 5,490,779 A | 2/1996 | Malmin |
| 5,505,916 A | 4/1996 | Berry, Jr. |
| D369,656 S | 5/1996 | Vos |
| D370,125 S | 5/1996 | Craft et al. |
| 5,525,058 A | 6/1996 | Gallant et al. |
| 5,526,841 A | 6/1996 | Detsch et al. |
| 5,540,587 A | 7/1996 | Malmin |
| 5,547,374 A | 8/1996 | Coleman |
| D373,631 S | 9/1996 | Maeda et al. |
| 5,554,014 A | 9/1996 | Becker |
| 5,554,025 A | 9/1996 | Kinsel |
| 5,556,001 A | 9/1996 | Weissman et al. |
| 5,564,629 A | 10/1996 | Weissman et al. |
| D376,893 S | 12/1996 | Gornet |
| D377,091 S | 12/1996 | Scott, Sr. |
| 5,613,259 A | 3/1997 | Craft et al. |
| 5,616,028 A | 4/1997 | Hafele et al. |
| 5,626,472 A | 5/1997 | Pennetta |
| 5,634,791 A | 6/1997 | Matsuura et al. |
| 5,636,987 A | 6/1997 | Serfaty |
| 5,640,735 A | 6/1997 | Manning |
| D382,407 S | 8/1997 | Craft et al. |
| 5,653,591 A | 8/1997 | Loge |
| 5,659,995 A | 8/1997 | Hoffman |
| 5,667,483 A | 9/1997 | Santos |
| D386,576 S | 11/1997 | Wang et al. |
| 5,683,192 A | 11/1997 | Kilfoil |
| 5,685,829 A | 11/1997 | Allen |
| 5,685,851 A | 11/1997 | Murphy et al. |
| 5,697,784 A | 12/1997 | Hafele et al. |
| D388,612 S | 1/1998 | Stutzer et al. |
| D388,613 S | 1/1998 | Stutzer et al. |
| D389,091 S | 1/1998 | Dickinson |
| 5,709,545 A | 1/1998 | Johnston et al. |
| D390,934 S | 2/1998 | McKeone |
| 5,716,007 A | 2/1998 | Nottingham et al. |
| 5,718,668 A | 2/1998 | Arnett et al. |
| 5,746,595 A | 5/1998 | Ford |
| 5,749,726 A | 5/1998 | Kinsel |
| 5,759,502 A | 6/1998 | Spencer et al. |
| 5,779,471 A | 7/1998 | Tseng et al. |
| 5,779,654 A | 7/1998 | Foley et al. |
| 5,795,153 A | 8/1998 | Rechmann |
| 5,796,325 A | 8/1998 | Lundell et al. |
| 5,833,065 A | 11/1998 | Burgess |
| 5,836,030 A | 11/1998 | Hazeu et al. |
| D402,744 S | 12/1998 | Zuege |
| 5,851,079 A | 12/1998 | Horstman et al. |
| D403,511 S | 1/1999 | Serbinski |
| D406,334 S | 3/1999 | Rosenthal et al. |
| 5,876,201 A | 3/1999 | Wilson et al. |
| D408,511 S | 4/1999 | Allen et al. |
| 5,901,397 A | 5/1999 | Häfele et al. |
| 5,934,902 A | 8/1999 | Abahusayn |
| D413,975 S | 9/1999 | Maeda |
| D416,999 S | 11/1999 | Miyamoto |
| D417,082 S | 11/1999 | Classen et al. |
| 5,993,402 A | 11/1999 | Sauer et al. |
| 6,030,215 A | 2/2000 | Ellion et al. |
| 6,038,960 A | 3/2000 | Fukushima et al. |
| 6,039,180 A | 3/2000 | Grant |
| 6,041,462 A | 3/2000 | Marques |
| 6,047,429 A | 4/2000 | Wu |
| D424,181 S | 5/2000 | Caplow |
| D425,615 S | 5/2000 | Bachman et al. |
| D425,981 S | 5/2000 | Bachman et al. |
| 6,056,710 A | 5/2000 | Bachman et al. |
| D426,633 S | 6/2000 | Bachman et al. |
| 6,089,865 A | 7/2000 | Edgar |
| 6,116,866 A | 9/2000 | Tomita et al. |
| 6,120,755 A | 9/2000 | Jacobs |
| 6,124,699 A | 9/2000 | Suzuki et al. |
| D434,500 S | 11/2000 | Pollock et al. |
| 6,159,006 A | 12/2000 | Cook et al. |
| 6,164,967 A | 12/2000 | Sale et al. |
| D435,905 S | 1/2001 | Bachman et al. |
| D437,049 S | 1/2001 | Hartwein |
| 6,193,512 B1 | 2/2001 | Wallace |
| 6,193,932 B1 | 2/2001 | Wu et al. |
| 6,199,239 B1 | 3/2001 | Dickerson |
| 6,200,134 B1 | 3/2001 | Kovac |
| D439,781 S | 4/2001 | Spore |
| 6,217,835 B1 | 4/2001 | Riley et al. |
| D441,861 S | 5/2001 | Hafliger |
| 6,230,717 B1 | 5/2001 | Marx et al. |
| 6,233,773 B1 | 5/2001 | Karge et al. |
| 6,234,205 B1 | 5/2001 | D'Amelio et al. |
| 6,237,178 B1 | 5/2001 | Krammer et al. |
| 6,247,929 B1 | 6/2001 | Bachman et al. |
| 6,280,190 B1 | 8/2001 | Hoffman |
| D448,236 S | 9/2001 | Murray |
| 6,293,792 B1 | 9/2001 | Hanson |
| D449,884 S | 10/2001 | Tobin et al. |
| D453,453 S | 2/2002 | Lun |
| D455,201 S | 4/2002 | Jones |
| D455,203 S | 4/2002 | Jones |
| 6,363,565 B1 | 4/2002 | Paffrath |
| D457,949 S | 5/2002 | Krug |
| D464,799 S | 10/2002 | Crossman et al. |
| 6,468,482 B1 | 10/2002 | Frieze et al. |
| 6,475,173 B1 | 11/2002 | Bachman et al. |
| 6,485,451 B1 | 11/2002 | Roberts et al. |
| 6,497,375 B1 | 12/2002 | Srinath et al. |
| 6,497,572 B2 | 12/2002 | Hood et al. |
| 6,502,584 B1 | 1/2003 | Fordham |
| D470,660 S | 2/2003 | Schaber |
| 6,532,837 B1 * | 3/2003 | Magussen, Jr. ....... B01L 3/0279 73/864.01 |
| 6,558,344 B2 | 5/2003 | McKinnon et al. |

(56) References Cited

U.S. PATENT DOCUMENTS

| | | | |
|---|---|---|---|
| 6,561,808 B2 | 5/2003 | Neuberger et al. |
| D475,346 S | 6/2003 | McCurrach et al. |
| D476,743 S | 7/2003 | D'Silva |
| 6,589,477 B1 | 7/2003 | Frieze et al. |
| 6,602,071 B1 | 8/2003 | Ellion et al. |
| 6,632,091 B1 | 10/2003 | Cise et al. |
| D482,451 S | 11/2003 | Page et al. |
| 6,640,999 B2 | 11/2003 | Peterson |
| 6,647,577 B2 | 11/2003 | Tam |
| 6,659,674 B2 | 12/2003 | Carlucci et al. |
| 6,669,059 B2 | 12/2003 | Mehta |
| D484,971 S | 1/2004 | Hartwein |
| 6,681,418 B1 | 1/2004 | Bierend |
| D486,573 S | 2/2004 | Callaghan et al. |
| 6,689,078 B1 | 2/2004 | Rehkemper et al. |
| 6,699,208 B2 | 3/2004 | Bachman et al. |
| 6,719,561 B2 | 4/2004 | Gugel et al. |
| D489,183 S | 5/2004 | Akahori et al. |
| 6,739,782 B1 | 5/2004 | Rehkemper et al. |
| 6,740,053 B2 | 5/2004 | Kaplowitz |
| D490,899 S | 6/2004 | Gagnon |
| D491,728 S | 6/2004 | Jimenez |
| D492,996 S | 7/2004 | Rehkemper et al. |
| 6,761,324 B2 | 7/2004 | Chang |
| 6,766,549 B2 | 7/2004 | Klupt |
| D495,142 S | 8/2004 | Berde |
| D495,143 S | 8/2004 | Berde |
| 6,779,216 B2 | 8/2004 | Davies et al. |
| 6,783,004 B1 | 8/2004 | Rinner |
| 6,783,505 B1 | 8/2004 | Lai |
| 6,796,796 B2 | 9/2004 | Segal |
| D498,643 S | 11/2004 | Pryor |
| 6,814,259 B1 | 11/2004 | Foster et al. |
| D499,885 S | 12/2004 | Xi |
| 6,835,181 B2 | 12/2004 | Hippensteel |
| D500,599 S | 1/2005 | Callaghan |
| 6,836,917 B2 * | 1/2005 | Blaustein ............ A61C 17/222 15/22.1 |
| 6,837,708 B2 | 1/2005 | Chen et al. |
| 6,884,069 B2 | 4/2005 | Goldman |
| 6,902,337 B1 | 6/2005 | Kuo |
| 6,907,879 B2 | 6/2005 | Drinan et al. |
| D509,585 S | 9/2005 | Kling et al. |
| D513,638 S | 1/2006 | Pan |
| D515,215 S | 2/2006 | Wang |
| D522,652 S | 6/2006 | Massey |
| 7,080,980 B2 | 7/2006 | Klupt |
| D529,661 S | 10/2006 | Schmidt |
| D530,010 S | 10/2006 | Luettgen et al. |
| 7,117,555 B2 | 10/2006 | Fattori et al. |
| D532,570 S | 11/2006 | Vizcarra |
| 7,131,838 B2 | 11/2006 | Suzuki et al. |
| D533,720 S | 12/2006 | Vu |
| 7,147,468 B2 | 12/2006 | Snyder et al. |
| D538,474 S | 3/2007 | Sheppard et al. |
| D548,334 S | 8/2007 | Izumi |
| D550,097 S | 9/2007 | Lepoitevin |
| D553,980 S | 10/2007 | VerWeyst |
| 7,276,035 B2 | 10/2007 | Lu |
| 7,314,456 B2 | 1/2008 | Shaw |
| D565,175 S | 3/2008 | Boyd et al. |
| 7,344,510 B1 | 3/2008 | Yande |
| D565,713 S | 4/2008 | Gao |
| 7,367,803 B2 | 5/2008 | Egeresi |
| D574,952 S | 8/2008 | Boyd et al. |
| 7,414,337 B2 * | 8/2008 | Wilkinson ................ B25F 5/00 15/21.1 |
| D577,198 S | 9/2008 | Jimenez |
| D577,814 S | 9/2008 | Seki et al. |
| D581,279 S | 11/2008 | Oates |
| 7,455,521 B2 | 11/2008 | Fishburne, Jr. |
| 7,469,440 B2 | 12/2008 | Boland et al. |
| D585,132 S | 1/2009 | Pukall |
| D588,262 S | 3/2009 | Pukall |
| 7,500,584 B2 | 3/2009 | Schutz |
| D590,492 S | 4/2009 | Powell |
| D592,748 S | 5/2009 | Boulton |
| D595,136 S | 6/2009 | Canamasas Puigbo |
| D601,694 S | 10/2009 | Rocklin |
| D601,697 S | 10/2009 | Sobeich et al. |
| D603,708 S | 11/2009 | Handy |
| D608,430 S | 1/2010 | Slothower |
| 7,670,141 B2 | 3/2010 | Thomas et al. |
| 7,677,888 B1 | 3/2010 | Halm |
| D613,550 S | 4/2010 | Picozza et al. |
| D621,949 S | 8/2010 | Seki et al. |
| D622,928 S | 9/2010 | Griebel |
| D623,376 S | 9/2010 | Griebel |
| D625,406 S | 10/2010 | Seki et al. |
| 7,814,585 B1 | 10/2010 | Reich |
| D629,884 S | 12/2010 | Stephens |
| 7,857,623 B2 | 12/2010 | Grez |
| 7,862,536 B2 | 1/2011 | Chen et al. |
| 7,878,403 B2 | 2/2011 | Hennick et al. |
| 7,959,597 B2 | 6/2011 | Baker et al. |
| D640,872 S | 7/2011 | Nanda |
| D648,539 S | 11/2011 | Wai |
| D651,409 S | 1/2012 | Papenfu |
| D651,805 S | 1/2012 | Hay |
| D653,340 S | 1/2012 | Goerge et al. |
| 8,113,832 B2 | 2/2012 | Snyder et al. |
| D655,380 S | 3/2012 | Taylor |
| D658,381 S | 5/2012 | Gebski |
| 8,220,726 B2 | 7/2012 | Qiu et al. |
| D666,912 S | 9/2012 | Kawai |
| 8,256,979 B2 | 9/2012 | Hilscher et al. |
| D668,339 S | 10/2012 | Luoto |
| D669,169 S | 10/2012 | Washington et al. |
| 8,297,534 B2 | 10/2012 | Li et al. |
| D670,373 S | 11/2012 | Taylor et al. |
| D670,958 S | 11/2012 | Picozza et al. |
| D671,637 S | 11/2012 | Gebski et al. |
| D672,018 S | 12/2012 | Bucher |
| 8,366,024 B2 | 2/2013 | Leber et al. |
| 8,403,577 B2 | 3/2013 | Khoshnevis |
| 8,403,665 B2 | 3/2013 | Thomas et al. |
| 8,408,483 B2 | 4/2013 | Boyd et al. |
| D686,311 S | 7/2013 | Mori |
| D694,378 S | 11/2013 | Bates |
| D694,398 S | 11/2013 | Taylor |
| D700,343 S | 2/2014 | Liu |
| D702,819 S | 4/2014 | Garland |
| D702,821 S | 4/2014 | Garland |
| D707,350 S | 6/2014 | Woodard |
| D709,183 S | 7/2014 | Kemlein |
| 8,801,667 B2 | 8/2014 | Taylor |
| D714,929 S | 10/2014 | Kim et al. |
| D714,930 S | 10/2014 | Kim et al. |
| D717,412 S | 11/2014 | Bucher |
| D717,427 S | 11/2014 | Kim |
| D718,855 S | 12/2014 | Kim et al. |
| D723,387 S | 3/2015 | Fath |
| D725,770 S | 3/2015 | Kim et al. |
| D731,640 S | 6/2015 | Kim et al. |
| 9,050,157 B2 | 6/2015 | Boyd et al. |
| D735,305 S | 7/2015 | Obara |
| D740,936 S | 10/2015 | Kim et al. |
| D745,329 S | 12/2015 | Ong |
| D746,975 S | 1/2016 | Schenck |
| D747,464 S | 1/2016 | Taylor |
| D754,330 S | 4/2016 | Kim et al. |
| D756,122 S | 5/2016 | Taylor |
| D764,051 S | 8/2016 | Wang |
| D766,423 S | 9/2016 | Kim et al. |
| D772,396 S | 11/2016 | Kim et al. |
| D772,397 S | 11/2016 | Kim et al. |
| D782,326 S | 3/2017 | Fath |
| 9,642,677 B2 * | 5/2017 | Luettgen ............ A61C 1/0092 |
| 2002/0090262 A1 | 7/2002 | Hall et al. |
| 2002/0108193 A1 | 8/2002 | Gruber |
| 2002/0119415 A1 | 8/2002 | Bailey |
| 2002/0152565 A1 | 10/2002 | Klupt |
| 2003/0060743 A1 | 3/2003 | Chang |
| 2003/0098249 A1 | 5/2003 | Rollock |

(56) References Cited

U.S. PATENT DOCUMENTS

| | | | |
|---|---|---|---|
| 2003/0162146 A1* | 8/2003 | Shortt | A61C 17/34 433/118 |
| 2003/0204155 A1 | 10/2003 | Egeresi | |
| 2003/0213075 A1 | 11/2003 | Hui et al. | |
| 2004/0045107 A1 | 3/2004 | Egeresi | |
| 2004/0076921 A1 | 4/2004 | Gofman et al. | |
| 2004/0122377 A1 | 6/2004 | Fischer et al. | |
| 2004/0126730 A1 | 7/2004 | Panagotacos | |
| 2004/0180569 A1* | 9/2004 | Chiou | H01R 13/5812 439/469 |
| 2004/0209222 A1* | 10/2004 | Snyder | A61C 17/02 433/80 |
| 2005/0004498 A1 | 1/2005 | Klupt | |
| 2005/0049620 A1 | 3/2005 | Chang | |
| 2005/0101894 A1 | 5/2005 | Hippensteel | |
| 2005/0102773 A1 | 5/2005 | Obermann et al. | |
| 2005/0144745 A1 | 7/2005 | Russell | |
| 2005/0177079 A1 | 8/2005 | Pan | |
| 2005/0271531 A1 | 12/2005 | Brown et al. | |
| 2006/0008373 A1 | 1/2006 | Schutz | |
| 2006/0010624 A1 | 1/2006 | Cleland | |
| 2006/0021165 A1 | 2/2006 | Boland et al. | |
| 2006/0026784 A1 | 2/2006 | Moskovich et al. | |
| 2006/0057539 A1 | 3/2006 | Sodo | |
| 2006/0078844 A1 | 4/2006 | Goldman et al. | |
| 2006/0079818 A1 | 4/2006 | Yande | |
| 2006/0207052 A1* | 9/2006 | Tran | A47L 11/34 15/320 |
| 2007/0082316 A1 | 4/2007 | Zhadanov et al. | |
| 2007/0082317 A1 | 4/2007 | Chuang | |
| 2007/0113360 A1 | 5/2007 | Tsai | |
| 2007/0202459 A1* | 8/2007 | Boyd | A61C 17/02 433/80 |
| 2007/0203439 A1* | 8/2007 | Boyd | A61C 1/0084 601/162 |
| 2007/0254260 A1 | 11/2007 | Alden | |
| 2008/0008979 A1 | 1/2008 | Thomas et al. | |
| 2008/0189951 A1 | 8/2008 | Molema et al. | |
| 2008/0213719 A1 | 9/2008 | Giniger et al. | |
| 2008/0307591 A1 | 12/2008 | Farrell et al. | |
| 2009/0070949 A1 | 3/2009 | Sagel et al. | |
| 2009/0071267 A1* | 3/2009 | Mathus | B01L 3/0227 73/864.14 |
| 2009/0082706 A1 | 3/2009 | Shaw | |
| 2009/0124945 A1 | 5/2009 | Reich et al. | |
| 2009/0139351 A1* | 6/2009 | Reichmuth | B01L 3/0279 73/864.11 |
| 2009/0163839 A1 | 6/2009 | Alexander | |
| 2009/0188780 A1 | 7/2009 | Watanabe | |
| 2009/0281454 A1 | 11/2009 | Baker et al. | |
| 2010/0010524 A1 | 1/2010 | Barrington | |
| 2010/0015566 A1 | 1/2010 | Shaw | |
| 2010/0190132 A1 | 7/2010 | Taylor et al. | |
| 2010/0239998 A1 | 9/2010 | Snyder et al. | |
| 2010/0261134 A1 | 10/2010 | Boyd et al. | |
| 2010/0261137 A1 | 10/2010 | Boyd et al. | |
| 2010/0326536 A1 | 12/2010 | Nan | |
| 2010/0330527 A1 | 12/2010 | Boyd et al. | |
| 2011/0027749 A1 | 2/2011 | Syed | |
| 2011/0076090 A1 | 3/2011 | Wu et al. | |
| 2011/0097683 A1 | 4/2011 | Boyd et al. | |
| 2011/0139826 A1 | 6/2011 | Hair et al. | |
| 2011/0144588 A1 | 6/2011 | Taylor et al. | |
| 2011/0184341 A1 | 7/2011 | Baker et al. | |
| 2011/0307039 A1 | 12/2011 | Cornell | |
| 2012/0021374 A1 | 1/2012 | Cacka et al. | |
| 2012/0045730 A1 | 2/2012 | Snyder et al. | |
| 2012/0064480 A1 | 3/2012 | Hegemann | |
| 2012/0077145 A1 | 3/2012 | Tsurukawa | |
| 2012/0141952 A1 | 6/2012 | Snyder et al. | |
| 2012/0179118 A1 | 7/2012 | Hair | |
| 2012/0189976 A1 | 7/2012 | McDonough et al. | |
| 2012/0266396 A1 | 10/2012 | Leung | |
| 2012/0277677 A1 | 11/2012 | Taylor et al. | |
| 2012/0277678 A1 | 11/2012 | Taylor et al. | |
| 2012/0279002 A1 | 11/2012 | Sokol et al. | |
| 2012/0295220 A1 | 11/2012 | Thomas et al. | |
| 2013/0089832 A1* | 4/2013 | Lee | A61C 17/0202 433/82 |
| 2013/0295520 A1 | 11/2013 | Hsieh | |
| 2014/0106296 A1 | 4/2014 | Woodard et al. | |
| 2014/0193774 A1 | 7/2014 | Snyder et al. | |
| 2014/0259474 A1 | 9/2014 | Sokol et al. | |
| 2014/0272769 A1 | 9/2014 | Luettgen et al. | |
| 2014/0272782 A1 | 9/2014 | Luettgen et al. | |
| 2014/0352088 A1 | 12/2014 | Wu | |
| 2015/0004559 A1 | 1/2015 | Luettgen et al. | |
| 2015/0147717 A1 | 5/2015 | Taylor et al. | |
| 2015/0173850 A1 | 6/2015 | Garrigues et al. | |
| 2015/0182319 A1 | 7/2015 | Wagner et al. | |
| 2016/0151133 A1 | 6/2016 | Luettgen et al. | |

FOREIGN PATENT DOCUMENTS

| | | |
|---|---|---|
| CN | 204049908 | 12/2014 |
| DE | 1466963 | 5/1969 |
| DE | 1566490 | 11/1970 |
| DE | 2019003 | 11/1971 |
| DE | 2409752 | 9/1975 |
| DE | 2545936 | 4/1977 |
| DE | 2714876 | 10/1978 |
| DE | 2910982 | 2/1980 |
| EP | 0023672 | 7/1980 |
| EP | 0515983 | 2/1992 |
| FR | 2556954 | 6/1985 |
| FR | 2654627 | 5/1991 |
| GB | 838564 | 6/1960 |
| GB | 1182031 | 2/1970 |
| GB | 2018605 | 10/1979 |
| GB | 2237505 | 5/1991 |
| JP | 2-134150 | 4/1990 |
| JP | 2009-39455 | 2/2009 |
| KR | 20120126265 | 11/2012 |
| WO | WO95/016404 | 6/1995 |
| WO | WO01/10327 | 2/2001 |
| WO | WO01/19281 | 3/2001 |
| WO | WO04/021958 | 3/2004 |
| WO | WO04/039205 | 5/2004 |
| WO | WO2004/062518 | 7/2004 |
| WO | WO2004060259 A2 | 7/2004 |
| WO | WO2008/070730 | 6/2008 |
| WO | WO2008157585 A1 | 12/2008 |
| WO | WO2013/095462 | 6/2013 |
| WO | WO2013/124691 | 8/2013 |
| WO | WO2014/145890 | 9/2014 |

OTHER PUBLICATIONS

Suvo. "Helical Gears vs Spur Gears—Advantages and Disadvantages Compared." Brighthub Engineering, Aug. 18, 2010, www.brighthubengineering.com/manufacturing-technology/33535-helical-gears-vs-spur-gears/.*

Waterpik WP 350W Oral Irrigator. Dentist.net. Copyright date 2013. Date accessed: Mar. 30, 2017, 2 pages <http://www.dentalhoo.com/waterpik-wp350.asp>.

iPik Portable Oral Irrigator. AliExpress. Date reviewed: Oct. 5, 2016. <https://www.allexpress.com/...e-Oral-Care-Product-Nasal-Irrigator-Tooth-Flosser-Water/1525541997.html?aff_platform=aaf&cpt=1490913714609&sk=yfAeyJa&aff_trace_key=c5a300c4f02e46d08c042f5292e1762f-1490913714609-07517-yfAeyJa>, 18 pages.

Brite Leafs Professional Portable 2-in-1 Nasal Sinus & Oral Irrigator. Brite Leafs. Copyright date 2012, <http://www.briteleafs.com/product6.html>, 1 page.

AliExpress. Date reviewed: Jan. 12, 2017. <https://www.aliexpress.com/item/Cordless-Water-Floss-Portable-Oral-Irrigator-Dental-Water-Flosser-Waterpic-Whatpick-Dental-Water-Pic-Whater-Pick/32769416341.html?spm=2114.40010308.4.75.Owuzfj>.

AliExpress. Date reviewed: Jan. 12, 2017. <https://www.aliexpress.com/item/Cordless-Water-Floss-Portable-Oral-Irrigator-Dental-

(56) References Cited

OTHER PUBLICATIONS

Water-Flosser-Waterpic-Whatpick-Dental-Water-Pic-Whater-Pick/ 32769416341.html?spm=2114.40010308.4.75.Owuzfj >.
The Right Tool, Electron Fusion Devices, Inc., 2 pages, at least as early as Feb. 1991.
Japanese Packaging, 2 pages, at least as early as Dec. 2002.
Japanese Instruction Brochure, 20 pages, at least as early as Dec. 2002.
Brochure: Woog International, "You have a 98% chance of getting gum disease. Unless you read this.", Lancaster, Pennsylvania, 5 pages, Feb. 1987.
Brochure: Woog International, "We put the control of home dental care back into the hands of the professional", Lancaster, Pennsylvania, 2 pages, Feb. 1987.
Brochure: WOOG International, "Products at a Glance: Home Dental Care System" WOOG ORAJET, 3 pages, at least as early as Dec. 18, 1998.
Website: http://www.just4teeth.com/product/Panasonic/ Panasonic_Portable_Irrigator.htm, 2 pages, at least as early as Jun. 20, 2003.
Website: http://www.videodirectstore.com/store/merchant. mv?Screen=PROD&Product_Code=EW1' . . . , 2 pages, at least as early as Jun. 20, 2003.
Website: http://products.consumerguide.com/cp/family/review/index.cfm/id/18742, 2 pages, at least as early as Jun. 20, 2003.
Website: http://www.racekarteng.com/images/walbroparts.gif and http://www.muller.net/mullermachine/docs/walbro1.html, 4 pages, at least as early as Jun. 20, 2003.
European Search Report, EPO Application No. 07250799.9, dated Jul. 5, 2007.
European Search Report, EPO Application No. 07252693.2, 14 pages, dated Apr. 28, 2008.
European Examination Report, EPO Application No. 07250799.9, dated Feb. 5, 2009.
International Search Report, Application No. PCT/US2010/028180, 2 pages, dated May 18, 2010.
International Search Report, PCT/US2010/060800, 2 pages, dated Feb. 11, 2011.
International Search Report, PCT/US2011/052795, 10 pages, dated Jan. 17, 2012.
Waterpik SinuSense Website: http://www.insightsbyapril.com/ 2012/03/waterpik-natural-remedy-for-sinus.html, 8 pages, retrieved on May 31, 2012.
Website: https://www.waterpik.com/about-us/, 3 pages.

\* cited by examiner

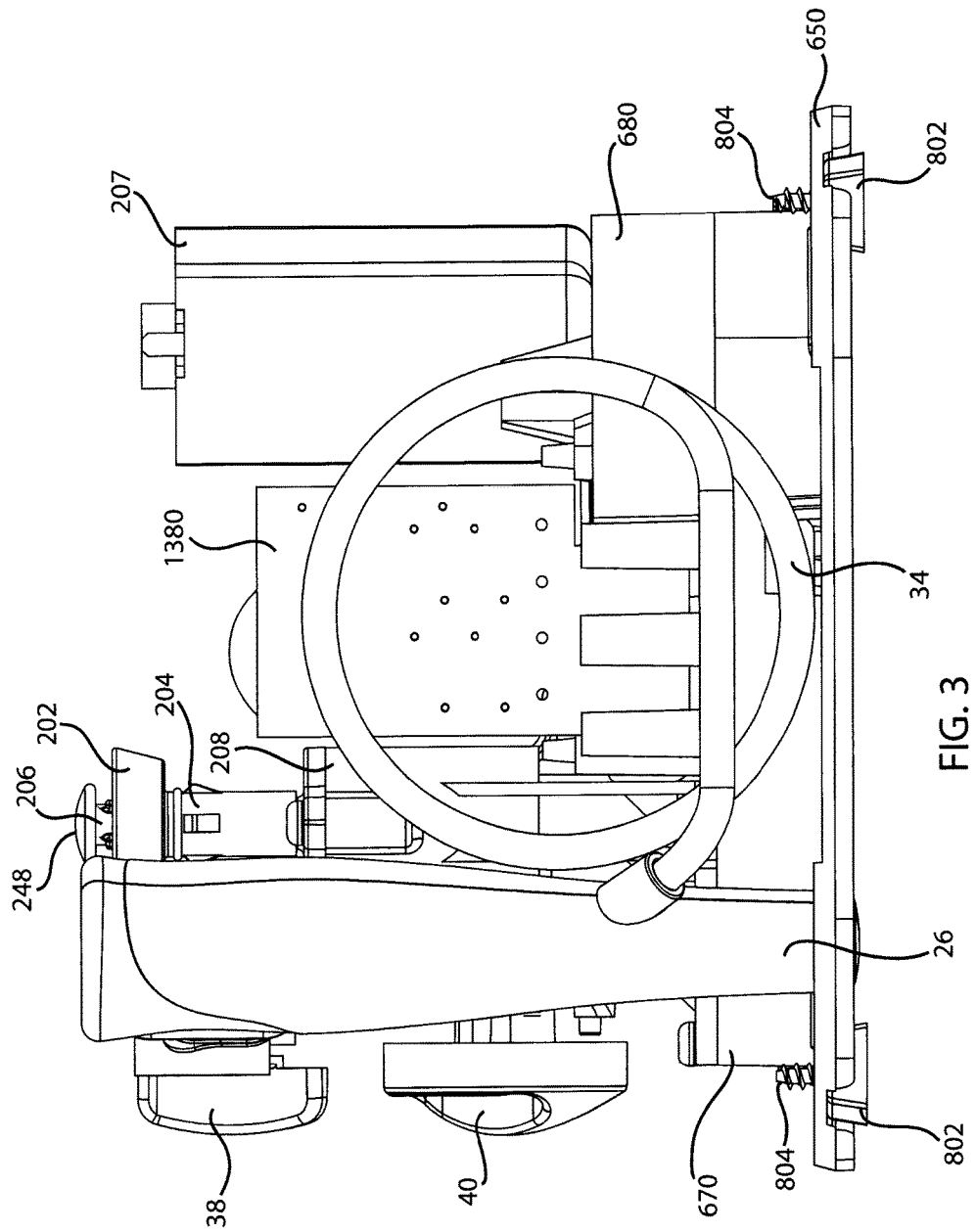

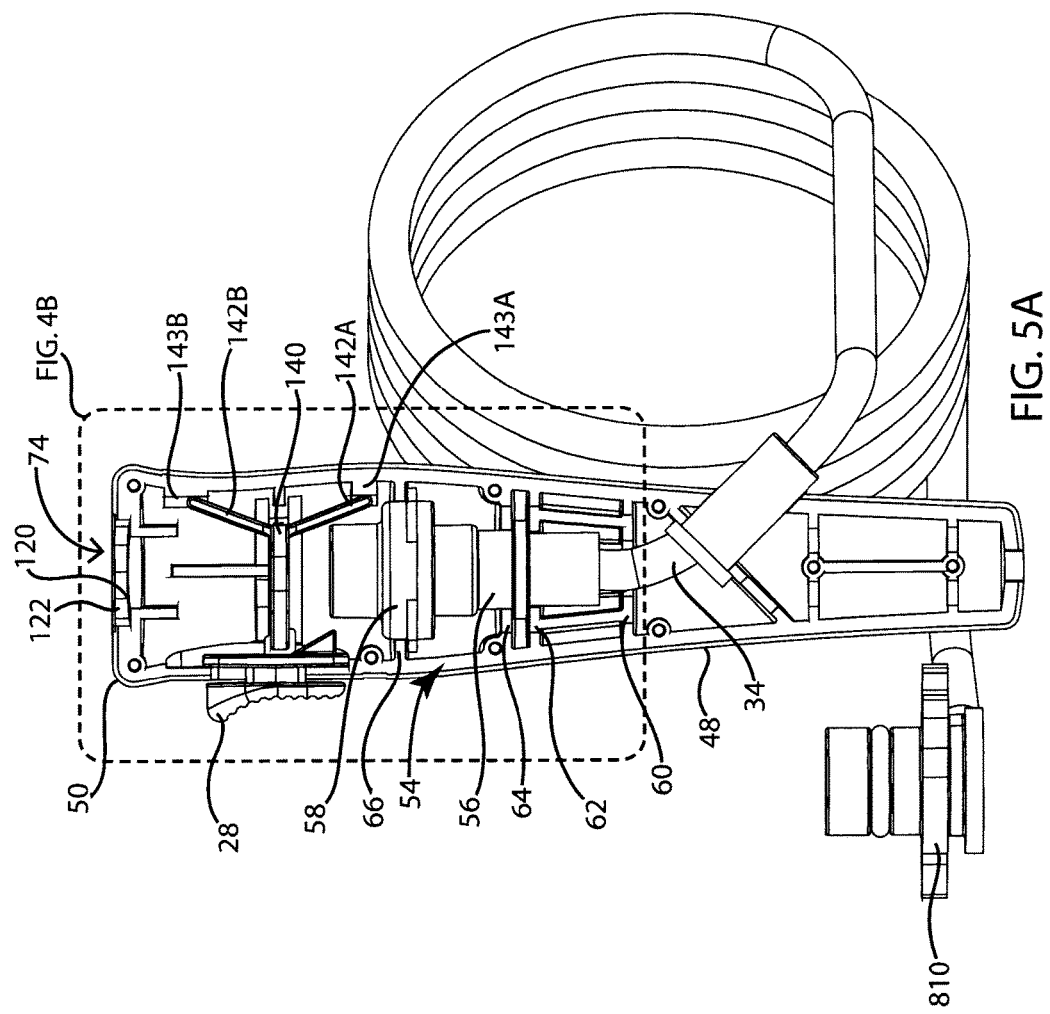

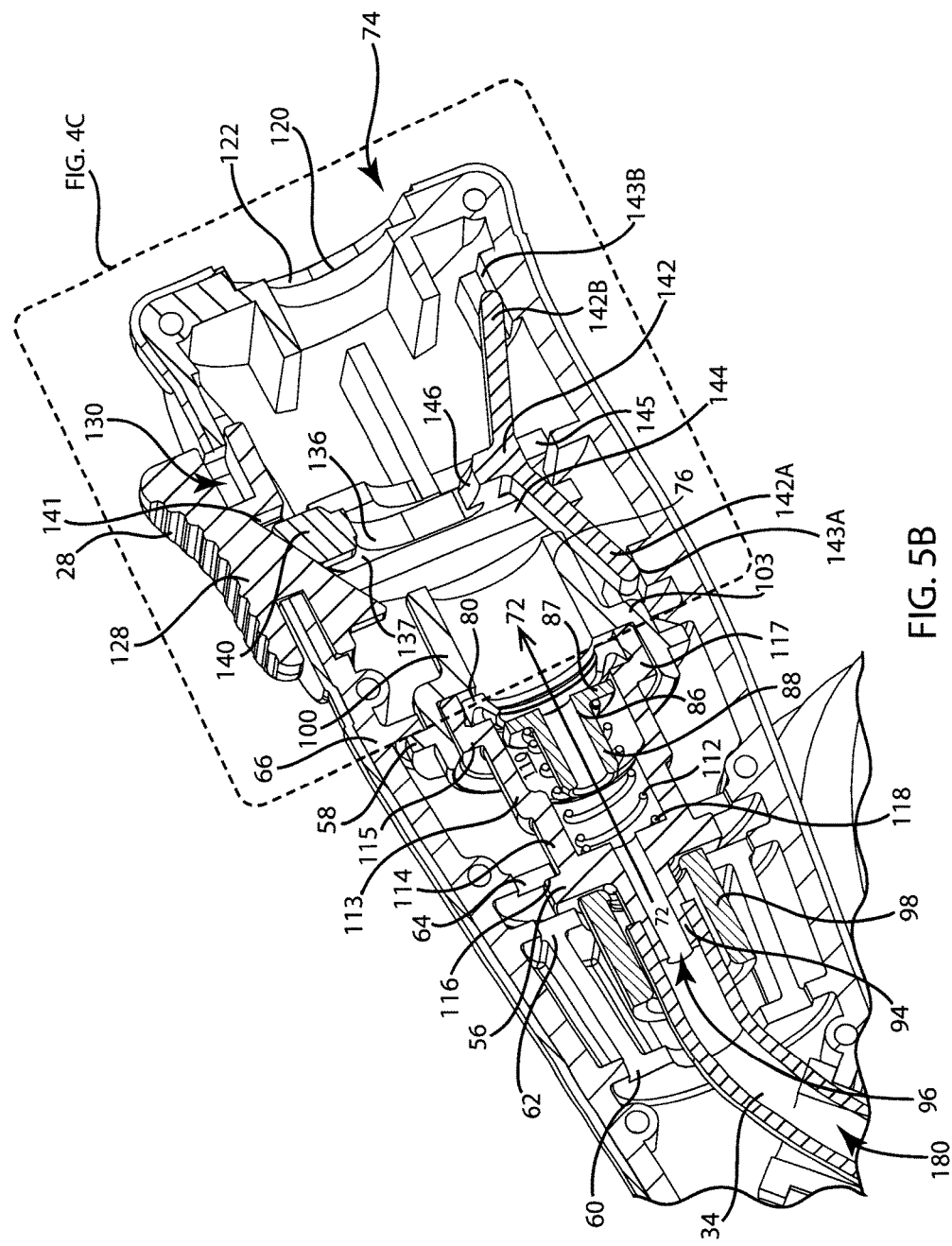

DENTAL WATER JET

CROSS REFERENCE TO RELATED APPLICATIONS

The present application claims priority pursuant to 35 U.S.C. § 119(e) to U.S. provisional application No. 61/919,511 filed 20 Dec. 2013 entitled "Dental Water Jet," which is hereby incorporated herein by reference in its entirety.

BACKGROUND

Harmful bacteria often grow deep between teeth and below the gum line. Traditional toothbrush and flossing often cannot reach these areas to remove the bacteria and food debris from these areas. To overcome the limitations of toothbrushes and flossers, a dental water jet may provide a pressurized water stream to remove trapped debris and harmful bacteria from areas not easily reached by a toothbrush or flosser. Such a dental jet unit typically consists of a pump supplying pressurized water from a water reservoir to a tip. The tip has an opening that permits the pressurized water stream to be directed to the desired locations within the mouth.

The pumps used in dental jet units for providing the necessary water pressures to effectively remove food debris and bacteria are often noisy. Both noise from moving parts and vibrations from the machine cause disturbances. Although the noise does not affect the dental jet's effectiveness at removing food debris and bacteria, it is often unpleasant for the user.

Further, many dental water jets may provide complicated retention mechanisms for when the tip is seated or mated with the dental water jet (typically within a handle). Thus, manufactures of such dental water jets may expend unnecessary resources in the manufacture of the oral irrigation devices.

Additionally, the water utilized in a water jet may leak into the base unit, handle, or other area of the device. Further, users of such water jets may experience a shortened life of the unit due to the leakage of water.

For these and other reasons, there is room in the art for an improved dental water jet.

SUMMARY

In accordance with various embodiments, a dental water jet may include a base housing enclosing a pump system driven by the piston and a motor which drives the piston. The water jet may also include a handle with a removable tip fluidly connected to the pump system. The water jet may also include a fluid reservoir removably positioned on the base. The water jet may also include a tube which fluidly connects the pump system to the handle. The base housing may include a gear housing attached to the bottom of the base housing. The gear housing houses a first gear attached to a motor shaft on the motor. The motor may be located above the gear housing and the motor shaft passes through the gear housing and into the first gear. The first gear engages a second gear which drives the piston. Gear housing may include a drain hole located at the bottom of the gear housing. The drain hole may be operable to direct liquids out of the gear housing. The base housing may be supported on a bottom surface by elastomer supports.

The handle may have a tip ejection switch which slides longitudinally along a portion of a length of the handle. The tip ejection switch may include a slide switch portion and an aperture portion. The aperture portion may engage the tip and prevent it from disconnecting from the pump system. The removable tip may include a retention groove which engages an aperture in the aperture portion. The aperture portion may have two spring arms extending out and in contact with one or more platforms formed on the interior wall of the handle. A ramped portion of the switch may contact a ramped portion of the aperture portion such that as the switch slides longitudinally the aperture portion slides laterally.

The tip may engage a spring loaded ejection unit. A proximal portion of the tip may pass through an o-ring sealing the tip into the fluidly connected system. The ejection unit may bias the tip into an aperture portion which engages a groove on the tip such that in response to the aperture portion being moved transversely out of the groove, the ejection unit forces the tip out of the handle. The proximal end of the tip may include a plurality of flat sides which engage a plurality of flat surfaces on the handle preventing the tip from rotating.

The tube may be supported by a plurality of hose retention brackets. The pump system may be powered by a power cord supported by internal strain relief comprising a strain relief wall which forms a 180 degree bend in the power cord.

The dental water jet may include a first helical gear attached to the motor and a second helical gear engaged with the first helical gear and engaged with the piston such that the motor drives the piston through the helical gears. A gear housing which houses the helical gears, wherein the motor is located above the gear housing and a motor shaft passes through the gear housing and into the first helical gear. The gear housing may include an aperture that the piston passes through and into a cavity of the base housing that encloses the pump the motor. The interior of the gear housing is sealed off from the cavity of the base housing that encloses the pump and the motor at the aperture by an elastomer seal that contacts the gear housing on all sides of the aperture and contacts the piston on all sides. The elastomer seal is a water resistant barrier which limits any contents of the gear housing from contaminating the water utilized in the dental water jet.

The elastomer support cushions may include a flat surface parallel with the bottom of the base housing and having annular walls which extend from the flat surface. The elastomer support cushions may also be connected to the bottom of the base housing by screws that are coaxial with the annular walls and extend through the flat surface and through the bottom of the base housing. The annular walls extend past the screw heads such that in response to being set on a flat surface the annular walls support the base housing.

The reservoir may include an elliptical step on the reservoir base which nests with an elliptical step located on the top exterior of the base housing.

The base housing may include an aperture on the outside for receiving a power cord. The aperture may extend through a side wall of the base housing and into the bottom surface of the base housing. The aperture may have a bottom wall with a second wall extending perpendicularly from the bottom wall such that the perpendicular wall directs the power cord to turn at a ninety degree angle and travel vertically into the housing along the perpendicular wall. A channel may be formed between the perpendicular wall and the bottom surface of the base housing which the power cord follows by making a 180 degree turn at the point where the perpendicular wall ends and following the perpendicular wall vertically back toward the bottom surface where the power cord makes a 90 degree turn and follows a path parallel with the bottom surface. After the power cord follows the path parallel with the bottom surface after the second 90 degree turn, the power cord may be restrained by a zip tie that passes through an aperture in the bottom surface and around the power cord.

BRIEF DESCRIPTION OF THE DRAWINGS

FIG. 3 depicts a front view with the outer housing removed showing an embodiment of the apparatus for providing a pressurized fluid stream.

FIG. 5A depicts a portion of the cross-sectional view of the handle shown in FIG. 1 showing a tip being inserted or removed from the handle.

FIG. 5B depicts a portion of the cross-sectional view of the handle shown in FIG. 1 showing a tip coupled to the handle.

DETAILED DESCRIPTION

One implementation of a dental water jet takes the form of an apparatus for providing a pressurized water stream for cleaning gums and teeth. The embodiment includes a base unit defining a cavity. The cavity contains a pump, which may move pressurized water from a reservoir to a tip in fluid communication with the pump. The reservoir may be supported on the base unit and in fluid communication with the pump. The pump may be connected to an electrical power source in order to power the pump. The pump may be turned on and off using a switch. A flow control knob may be turned to selectively adjust the water pressure supplied by the tip between a minimum and a maximum value. The reservoir may be removed from the base unit so that it may be filled with a fluid, such as water, from a fluid source (such as a water faucet).

Fluid may flow from the reservoir, through the base supporting the reservoir, along a tube, from the tube into the handle, and into the tip. The fluid may be propelled by a motive source, such as a piston, to facilitate this flow. Fluid may ultimately be ejected from the tip and into the mouth of a user (for example) to provide oral irrigation and/or cleaning of the teeth, gums, and tongue.

Figure 1:
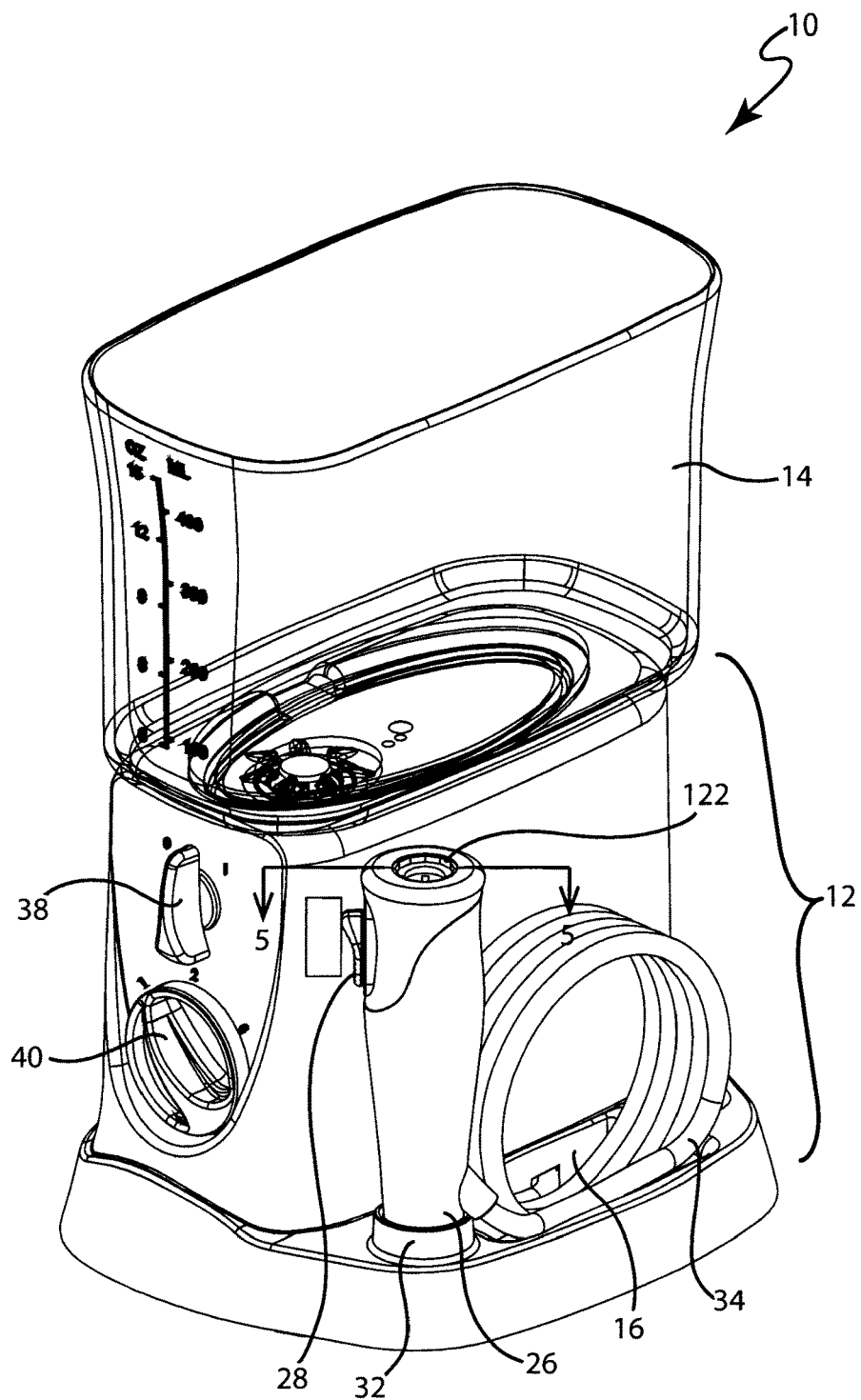
FIG. 1 depicts a perspective view of an embodiment of an apparatus for providing a pressurized fluid stream.

FIG. 1 depicts a perspective view of a first embodiment of an oral irrigator base unit 10 for providing a pressurized fluid stream. The embodiment may include a base unit 12, which may support a reservoir 14 for storing a fluid such as water. A container 16 having a depressed area for storing items, including accessories utilized with the apparatus 10. One exemplary accessory is a tip 24 having an opening for delivering a pressurized fluid stream. Such a tip 24 may be attached to a handle 26 having a latch 28 that selectively detaches the tip 24 from the handle 26. The handle 26 may be removably secured to the base unit 12 via a handle receptacle 32 joined to the base unit 12. Handle 26 may be coupled to a tube 34 in fluid communication with a pump contained within the base unit 12. A power cord 36 (not shown) may connect a power source (not shown) to the pump. A switch 38 may be connected to the base unit 12 for turning the pump on and off.

Additional controls may be used beyond the aforementioned switch 38. For example, a knob 40 may be connected to the pump for adjusting the fluid pressure of a fluid supplied by the pump. The knob 40 may be, for example, inserted through a knob aperture in the base unit 12 in order to be accessible to an operator. Each of the base unit 12, reservoir 14, container 16, tip 24, handle 26, handle receptacle 32, tube 34, switch 38, and knob 40 may be composed of plastic, metal, rubber, carbon composites, another suitable material, or some combination thereof.

Figure 2:
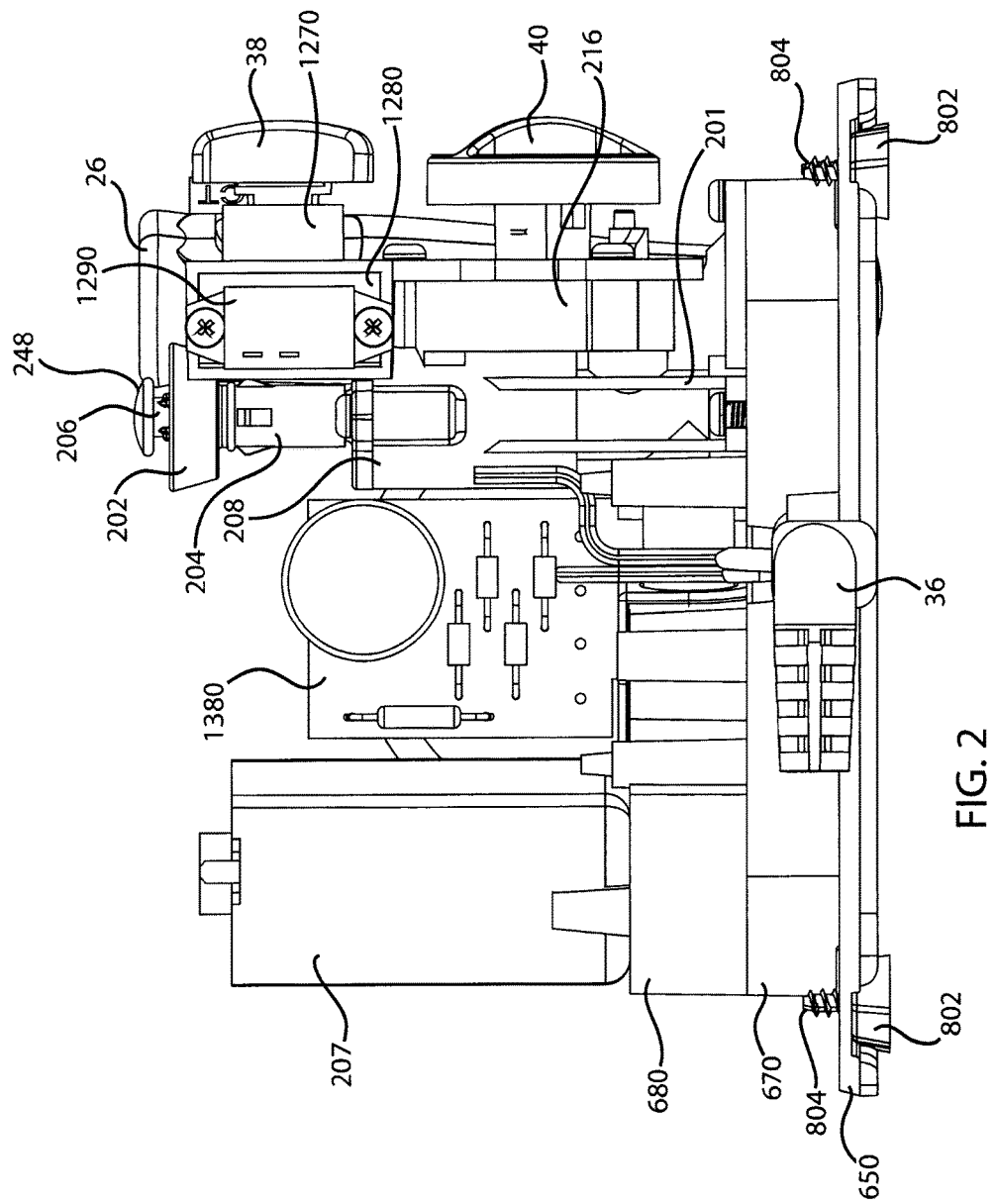
FIG. 2 depicts a rear assembly view with the outer housing removed showing an embodiment of the apparatus for providing a pressurized fluid stream.

FIGS. 2 and 3 depicts assembly views in which the outer housing and reservoir 14 are shown removed. With reference to these figures, the base unit may contain a motor 207 positioned above a gear housing 680. The gear housing 680 may be attached to a bottom shelf 670. The gear housing 680 and the bottom shelf may be a single contiguous structure or they may be separable structures. As discussed in more detail later the bottom shelf 670 is a recessed portion of the bottom surface of the base housing. The recessed portion provides access to certain serviceable components from the bottom of the apparatus 10. The base unit may also contain a rectifier circuit 1380, positioned between the motor 207 and a pump body 208. The pump body 208 may be supported by a pump bracket 201 below. Knob 40 is shown positioned on the front (described below) of the unit and is operable for adjusting the fluid pressure delivered to the tip 24 by the pump. A reservoir valve 206 may be connected to a tube stand 204, as described in more detail below. The tube stand 204 may be connected to a pump inlet body 202, which may be connected to a pump body 208 with fasteners (such as screws). A flow control 216 may also be connected to the pump body 208 with fasteners such as screws. A piston 1105, received within a piston housing, may be operatively associated with the pump body 208 as described in more detail below. The piston may also include a bushing 1103 within the housing. (see FIG. 15) The pump body 208 may also be connected to a fitting, which may be used to fluidly communicate the tube 34 with the pump.

Figure 4A:
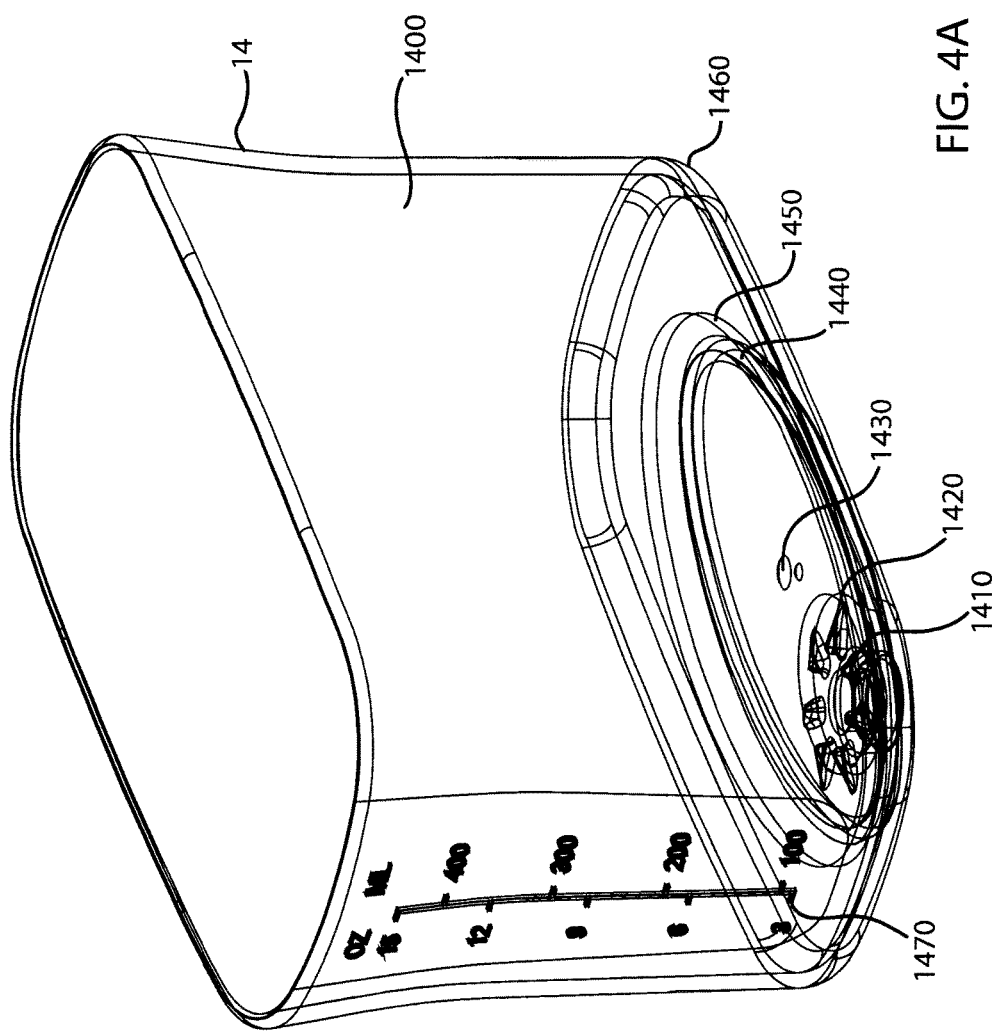
FIG. 4A depicts a perspective view of an embodiment of the reservoir of FIG. 1.
Figure 4B:
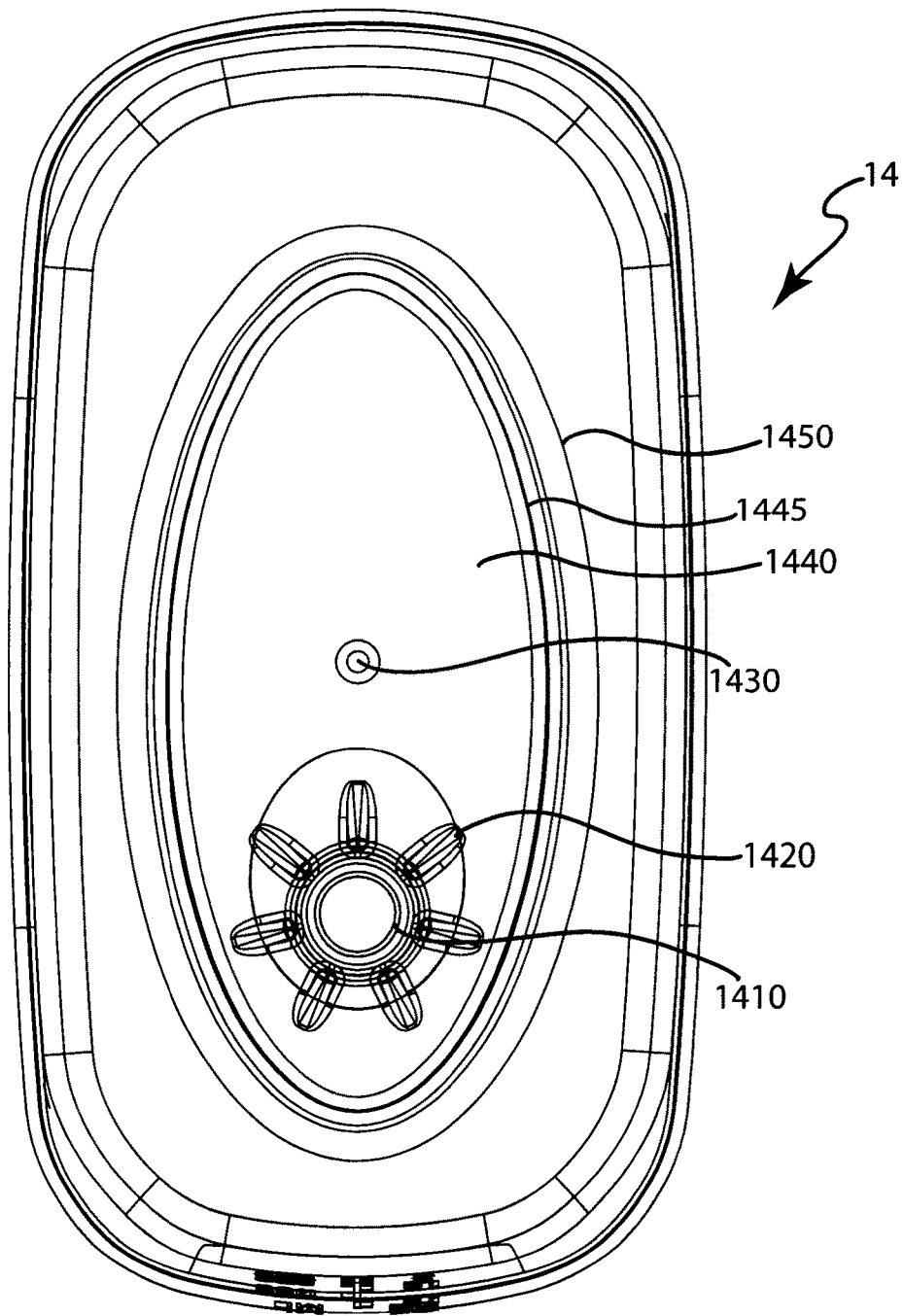
FIG. 4B depicts a bottom view of an embodiment of the reservoir of FIG. 1.

One or more tube stand projections 1420, as depicted in FIGS. 4A and 4B may be located within the reservoir around the reservoir opening 1410. The tube stand projections 1420 may contact the reservoir valve 206, which seats within a reservoir opening 1410. The reservoir opening 1410 may be an aperture located in the bottom of the reservoir 1440. The tube stand projections 1420 lift a reservoir valve head 248 off the bottom of the reservoir 1440, thereby enabling fluid to enter and exit the reservoir 14 through the reservoir valve 206 and the fluid passage within tube stand 204. In particular, when the reservoir 14 is supported by the base unit 12, the tube stand 204 and the reservoir valve 206 are generally co-axially aligned with the tube stand projections 1420 and reservoir opening 1410. This pushes the reservoir valve head 248 away from the bottom of the reservoir 1440. When the reservoir 14 is removed from the base unit 12, the reservoir valve head 248 will deform but then return to its original position. Gravity and/or fluid pressure may also aid in returning the reservoir valve head 248 to its original position.

The switch 38 may be connected to a switch unit 1270. The switch unit 1270 may connect the rotating switch 38 to the linear switch 1290. The switch unit 1270 may translate the rotational action of switch 38 to a linear input operable to actuate linear switch 1290.

The oral irrigator base unit 10 may include a bottom plate 650. The bottom plate 650 may be attached to bottom shelf 670. As viewed from the bottom, the bottom shelf 670 bay be recessed into the bottom plate 650. The bottom plate 650 may be attached to and supported by elastomer supports 802. The elastomer supports 802 may be attached to bottom plate 650 by screws 804. The bottom plate 650 may also receive power cord 36.

Figure 4C:
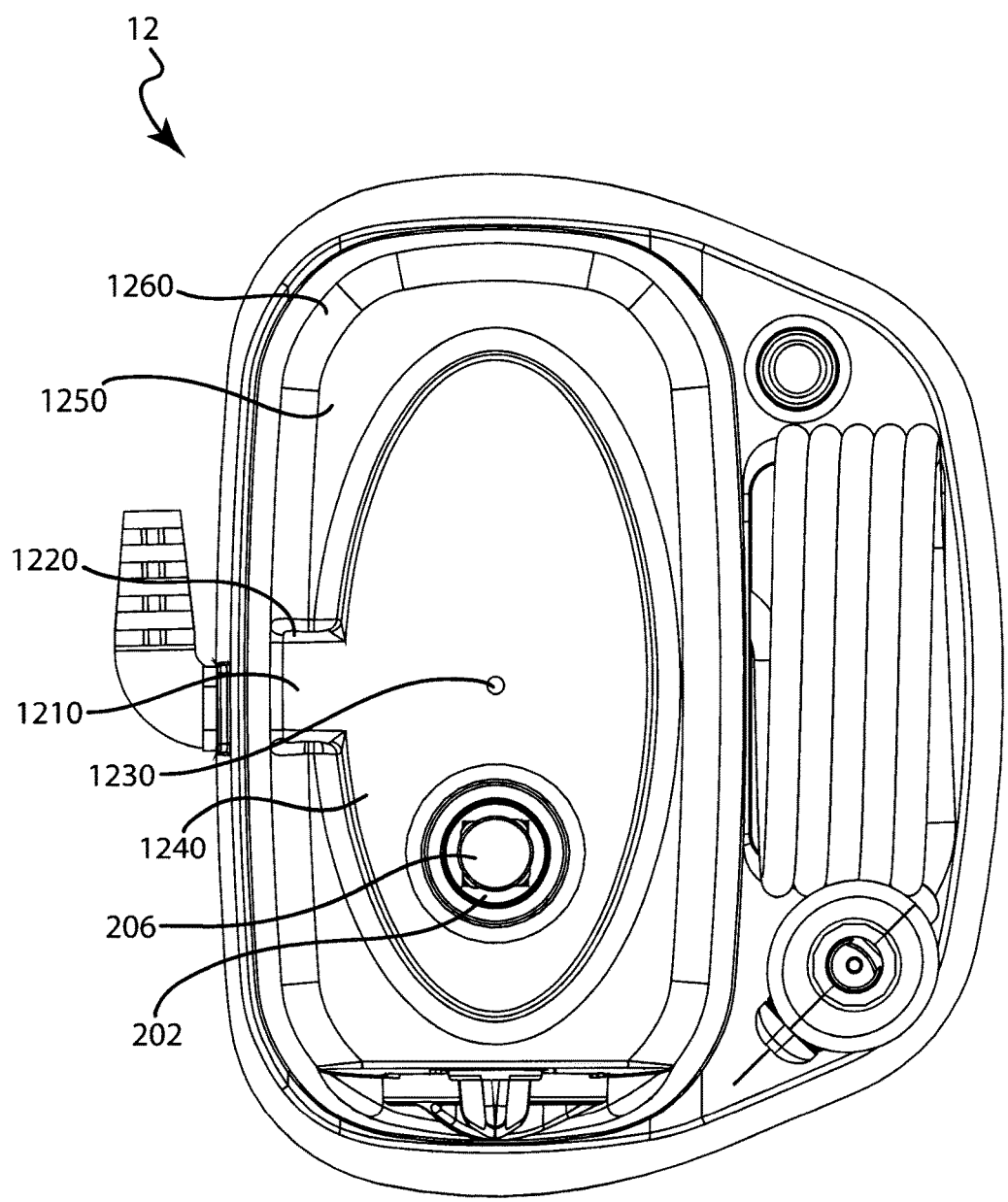
FIG. 4C depicts a top view of the base unit of FIG. 1 which receives the reservoir of FIG. 1.

FIG. 4A depicts a perspective view of an embodiment of the reservoir of FIG. 1; FIG. 4B depicts a bottom view of an embodiment of the reservoir of FIG. 1; and FIG. 4C depicts a top view of the base unit of FIG. 1 which receives the reservoir of FIG. 1. As illustrated in these figures, the reservoir 14 may include the reservoir base or bottom surface 1440 and a reservoir wall 1400. The reservoir base may have more than one level. For example the reservoir may have a bottom surface 1440 and a second surface 1450. The bottom surface and second surface 1440, 1450 may be connected by transition or step 1445. In various embodiments, the bottom surface 1440 may be formed of a specific shape configured to nest with the base unit 12 for locating the reservoir 14. For example the bottom surface 1440 may be elliptical. This shape may aid in placing the reservoir valve 206 above or adjacent to the tube stand 204. The reservoir wall 1400 may extend vertically from the reservoir base, meaning bottom surface 1440 and/or second surface 1450. The reservoir base may also have a rounded transition 1460 between the base and the wall 1400. The tube stand 204 may include a generally cylindrical tube stand shaft 232 with a generally partial-conical tube stand collar 236 formed on an end of the tube stand shaft 232. The reservoir valve 206 may include a generally cylindrical reservoir valve shaft 250 with a generally circular reservoir valve head 248 formed on an end of the reservoir valve shaft 250. The pump inlet body 202 may encompass the reservoir opening 1410 in the reservoir base, thereby substantially preventing a fluid from flowing through the reservoir opening 1410 when the reservoir valve head 248 bears against the reservoir base. The reservoir may have an additional locating feature 1430. The additional locating feature 1430 may be operable to align with another locating feature on the base unit 12 in order to easily and accurately align the reservoir and the base unit. The reservoir 14 may include molded in graduations 1470. The reservoir may be made of polypropylene forming a very strong structure that is resistant to breakage when dropped.

As depicted in FIG. 4C, the top of the base unit 12 may have features similar to the bottom of the reservoir 14. For example, the base unit 12 may have an elliptical surface 1240. The elliptical surface 1240 may be sized to receive the bottom surface 1440. The elliptical surface 1240 may transition along step 1220 to a second surface 1250 which is operable to provide additional support to reservoir 14. Base unit 12 may have locating feature 1230 that corresponds to locating feature 1430 on the reservoir. A channel 1210 may extend from the elliptical surface 1240 through the second surface 1250 out the side of base unit 12. This channel 1210 will thus have the same surface height as elliptical surface 1240. In some embodiments this channel 1210 may slope down from the elliptical surface 1240. The channel 1210 is operable to drain fluids out of the elliptical surface 1240 that may accumulate there from leakage or spills. The second surface 1250 may transition to the side walls of base unit 12 along curved transitions 1260.

Figure 5C:
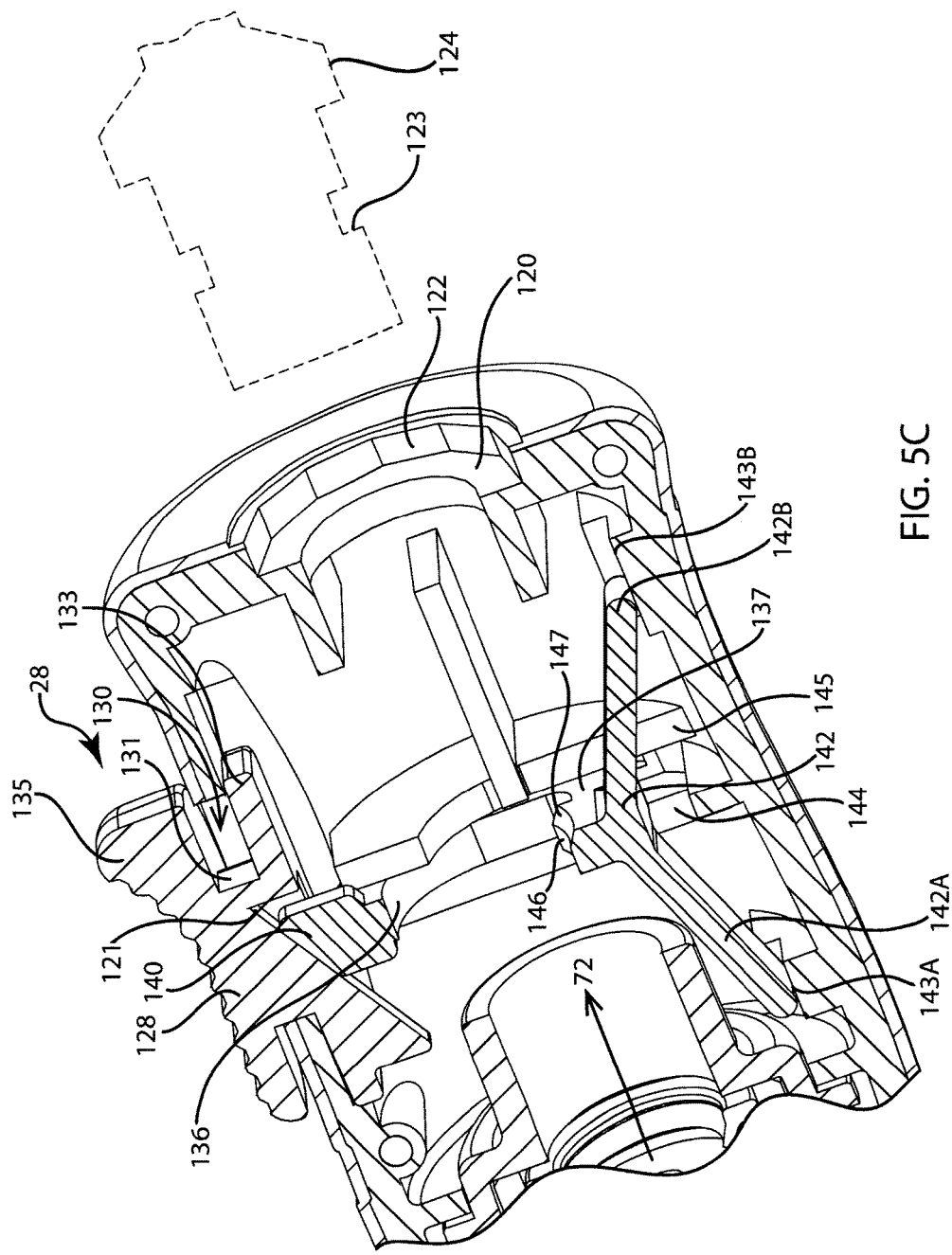
FIG. 5C depicts a portion of the cross-sectional view of the handle shown in FIG. 1 showing a tip coupled to the handle.

FIG. 5A depicts a portion of the cross-sectional view of the handle shown in FIG. 1, while FIG. 5B and FIG. 5C depict a portion of the cross-sectional view of the handle shown in FIG. 1. With reference to these figures, the handle 26 may include a handle housing 48 composed of a first and second housing segment 50, 52 (segment 50 shown in 5A-C and 50, 52 shown in FIG. 6). The first and second handle housing segments 50, 52 together define a cavity 54 in which an ejection unit 56, the tube 34, and a collar unit 58 may reside. The first and second handle housing segments 50, 52 may each include first, second, third and fourth interior walls 60, 62, 64, 66 for aligning the ejection unit 56, the tube 34, and the collar unit 58 within the cavity 54. The interior walls 60, 62, 64, 66 generally extend in a horizontal plane with respect to the handle 26, and inwardly from one of the first and second housing segments 50, 52. Each interior wall 60, 62, 64, 66 may align with a mating interior wall extending from the opposing housing segment when the handle 26 is assembled.

The ejection unit 56 may define a fluid passage along its length. In particular, an inner surface of the ejection unit 56 may define an ejection unit aperture for receiving a collar unit 58. An interior aperture extending through both the ejection unit 56 and the collar unit 58 define a first fluid passage 72 extending through the first and second handle housing segments 50, 52. The handle housing segments 50, 52 may define a handle head 74 formed at the top of the handle 26. (As explained below, the handle head 74 generally receives the tip 24.) The collar unit 58 may include a collar surface 76 that may encircle at least a portion of the first fluid passage 72. The collar surface 76 may be sized to receive the proximal end of the tip 24.

Additionally, the inner surface of the ejection unit 56 may be stepped to define an interior O-ring space operable to receive or contain O-ring 80 between the end of the ejection unit 56 (i.e., the end of the ejection unit 56 opposite the connection with tube 34) and the collar unit 76. This change in the cross-sectional area forms a step. The step may support ejection unit O-ring 80, which may prevent pressurized fluid from leaking into the handle housing 48 along the joint formed between the ejection unit 56 and the collar unit 58.

At a second end of the ejection unit 56 (i.e., the end of the ejection unit 56 adjacent the tube 34), an arrowhead shaped wall 94 for receiving the tube 34 may extend from the ejection unit 56 in a direction generally aligned with the handle's 26 longitudinal axis. The wall includes an aperture that extends coaxially with the first fluid passage 72. The arrowhead shaped wall 94 may be formed as an annular barb at the end of wall 94 and operable to engage and prevent or limit tube 34 from pulling off wall 94. When joined to the ejection unit 56 by the arrowhead shaped wall 94, the tube 34 may fluidly communicate with the first fluid passage 72 via an opening 96 in the arrow-head shaped wall 94. A tube clamp 98 may clamp the portion of the tube's 34 inner surface received by the arrowhead shaped wall 94 against the arrowhead shaped wall's 94 outer surface.

The first fluid passage 72 may also extend through the ejection unit 56 and toward the collar unit 58. The ejection unit 56 may include a collar engagement annular wall 115. The wall 115 may be coaxial with the first fluid passage 72. The exterior surface of wall 115 may insert into and along the interior surface of wall 102. The ejection unit 56 may have a various other segments with different walls. The ejection unit 56 may have a second annular wall 113 which is smaller in diameter than and connects to wall 115. The wall 115 and the second annular wall 113 may be connected by a wall 117 that extends away from annular wall 113 as a flange. The wall 115 may protrude from of wall 117 with a larger diameter than wall 113. The wall 117 may have a flat interior surface that mates with the O-ring 80. The ejection unit 56 may include anther annular wall 114. The wall 114 may connect to wall 113. The annular wall 114 may have a smaller diameter than the annular wall 113. A flange 116 extends annularly away from the annular wall 114. The flange 116 may align the ejection unit 56 with the first and second handle housing segments 50, 52. For example the flange 116 may be located between the interior walls 62 and 64. The flange 116 may also define an interior surface 118 within the interior space 110 which is defined by the annular walls 114, 113, and 115.

A spring 112 may be located within the space 110. The inner surface 118 may define a receiving surface for the spring 112. On the spring's opposite end, the spring 112 may contact plunger 86. The plunger may have an annular wall 88 extending longitudinally with a flange 87 extending outwardly from the annular wall on one end. The annular wall 88 may receive the spring 112 around its outside surface. The spring may slide along the annular wall 88 until it contacts flange 87. The spring 112 may compress between the inner surface 118 and the plunger 86 due to any force acting against the plunger 86. The spring 112 may exert an upward force against the plunger flange 87 when compressed. This upward force may tend to drive the plunger flange 87 away from the ejection unit 56. The plunger may also define a center passage through which the first fluid passage 72 passes through the plunger.

The first fluid passage 72 may extend through the collar unit 58 and toward the handle head 74. The collar unit 58 may include an annular wall 100 (or walls, in some embodiments) surrounding the first fluid passage 72. The interior surface of annular wall 100 may be collar surface 76. The collar unit 58 may have a various segments with different diameters. For example the annular wall 100 may have a first diameter with the collar surface 76 sized to receive and mate with an exterior surface of tip 24. The collar unit 58 may have a second annular wall 102 on the end of the collar unit 58 adjacent to the ejection unit 56. The second annular wall 102 may be sized to receive the end of the ejection unit 56. The second annular wall 102 may be larger in diameter than the annular wall 100. The annular wall 100 and the second annular wall 102 may be connected by a wall 103 that extends away from annular wall 100 as a flange and the second annular wall 102 may protrude off of annular 103. The wall 103 may have a flat interior surface that mates with the end of the ejection unit 56 or the O-ring 80. In this manner the O-ring may be restrained between wall 103 and wall 117. The collar unit 58 may include flange 104 which extends annularly away from the second annular wall 102. The flange 104 may align the collar unit 58 with the first and second handle housing segments 50, 52. For example the flange 104 may contact or mate with interior wall 66. As indicated above, the collar surface 76 may be composed of the inner surface of the annular wall 100 and have an axis that is generally parallel to the longitudinal axis of the handle 26.

The plunger 86 may be depressed when a tip 24 is received through collar unit 58 and coupled with the latch 28 as described in more detail below. A portion of tip 24 passes through O-ring 80 and contacts plunger 86. As the plunger 86 is depressed, the first spring 112 compresses. The compression of the first spring 112 will exert an upward force, which will force tip 24 out of the assembly but being restrained against latch 28. When the tip 24 is coupled with the latch 28 as described in more detail below, this upward force is opposed. When the tip 24 is decoupled from the latch 28, the force opposing the upward force exerted by the first spring 112 is removed, thereby allowing the first spring 112 to move the plunger 86 back to its original position. This movement of the plunger 86 from a compressed position to an uncompressed position allows the tip 24 to extend out of the housing 26 and provides an indication the tip 24 can be removed and/or replaced.

Figure 6:
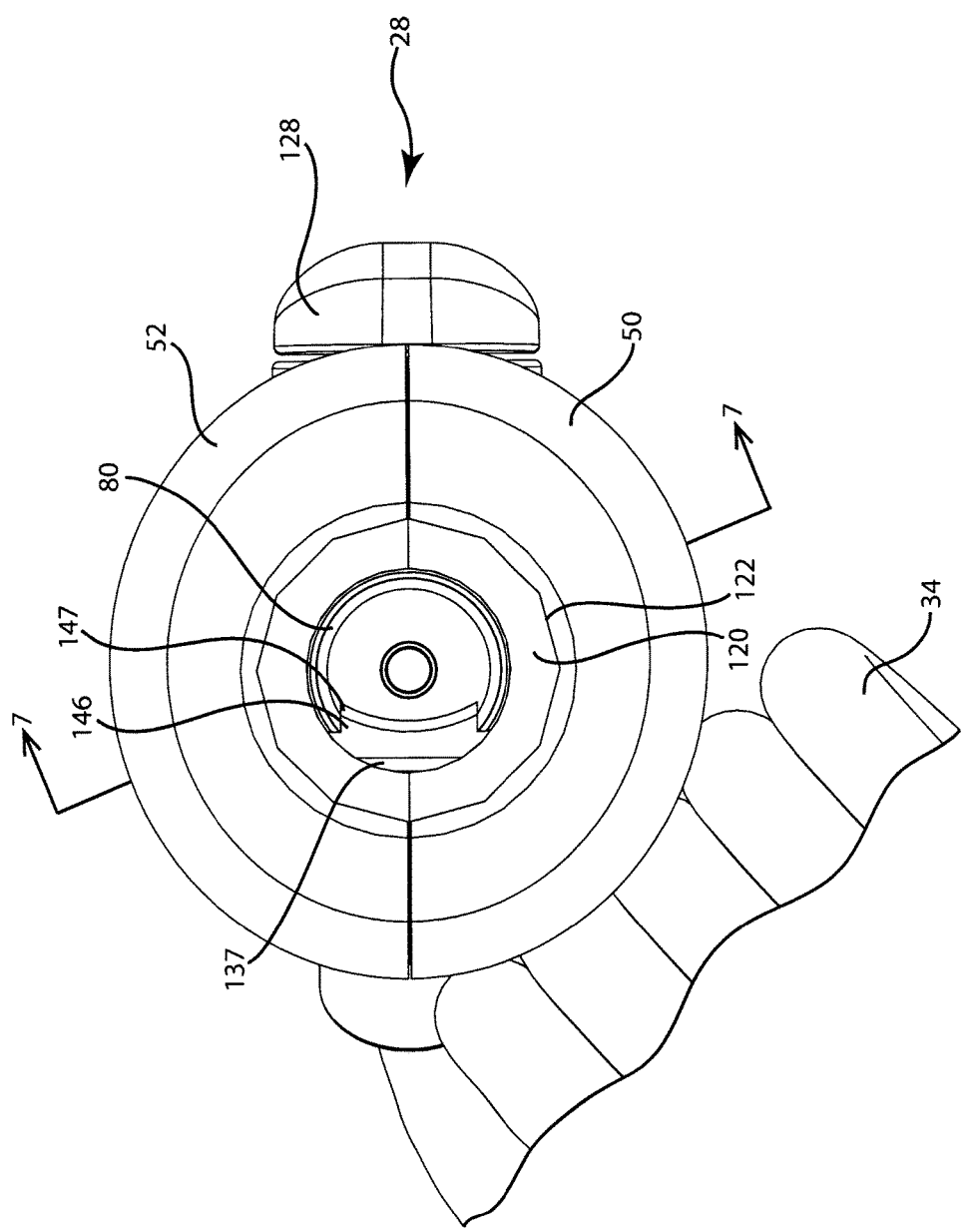
FIG. 6 depicts a top view of the handle shown in FIG. 1, showing a tip attachment receiver on the handle.
Figure 7:
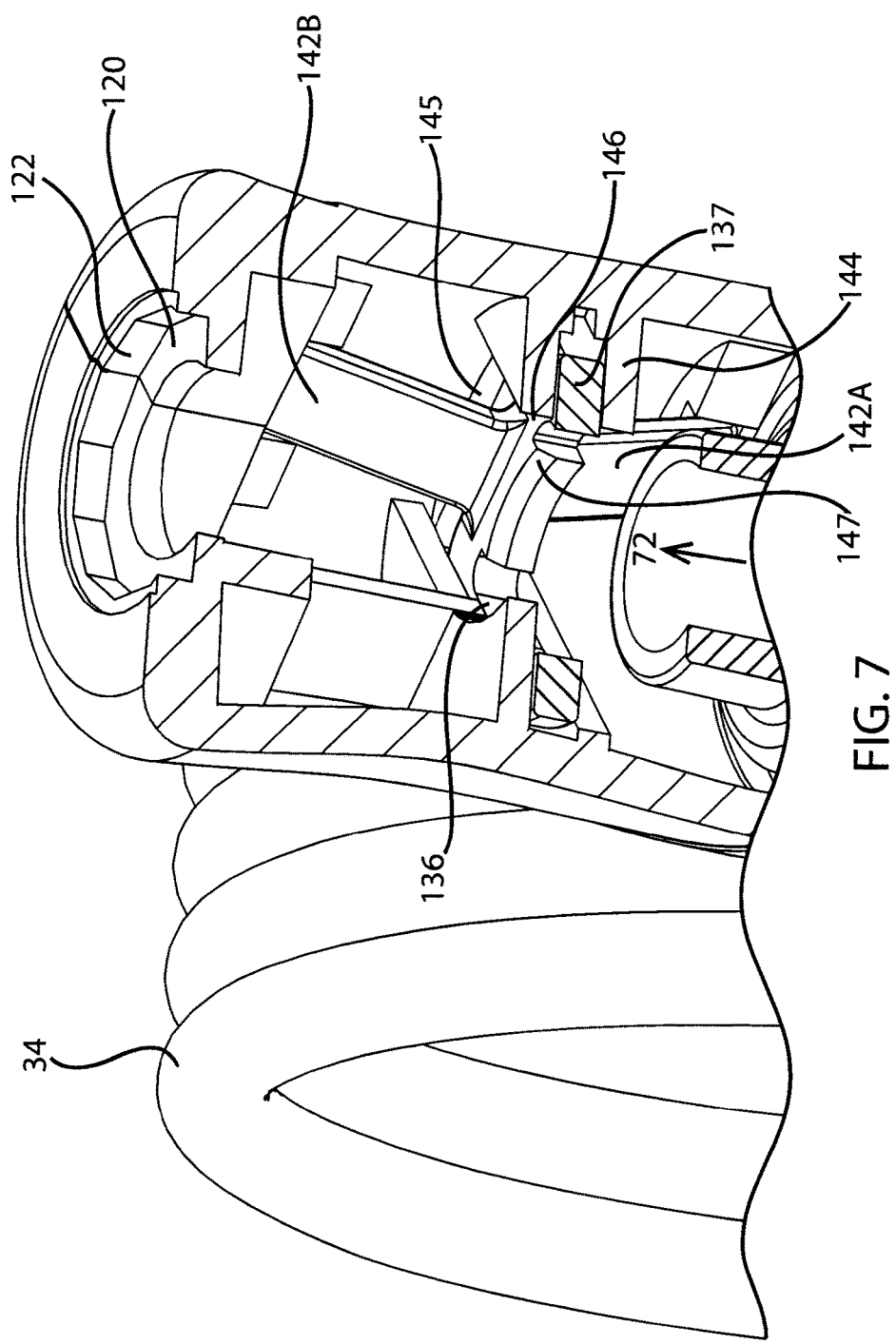
FIG. 7 depicts a portion of a cross-sectional view of the handle shown in FIG. 5.

The handle head 74 may include a recessed surface 120 encompassing an opening adapted to receive the tip 24 and surrounded by a recessed wall 122. With reference to FIGS. 5A, 5B, and 6, the recessed wall 122 may define a polygonal shape adapted to mate with a polygonal exterior surface 124 of tip annular ring extending from an exterior surface of a portion of the tip 24, namely a tip shaft 126. The engagement of the recessed wall 122 with the tip polygonal exterior surface 124 may limit or prevent the tip 24 from rotating around a longitudinal axis of the handle.

As mentioned above, the latch 28 may permit the tip 24 to be selectively attached or detached from the handle 26, and specifically from the handle head 74. The operation of the latch 28 will now be described. With reference to FIGS. 1, 5A, 5B, and 5C, the latch 28 may have a latch slide body 128 and a latch aperture structure 140. As shown in FIGS. 5B and 5C, an aperture 130 may extend through housing 48. The latch slide body 128 may extend through the aperture 130. The latch slide body may have a trunk 131 which extends between an internal flange 133 and external contact surface 135. The aperture 130 may be elongated such that latch trunk is free to move back and forth in a longitudinal direction within the aperture. The contact surface 135 and the internal flange 133 contact the exterior and interior surfaces of housing 48 respectively. This contact limits or prevents the switch from separating from housing 48 but permits movement in the longitudinal direction. The switch slide body 128 includes a slide body ramped surface 121.

The latch aperture structure 140 may be a separate component operable to interact with the latch slide body 128 in order to selectively attach or detach tip 24 from the handle 26. The latch aperture structure 140 may include a frame structure 137 which defines a central aperture 136. The central aperture 136 may be sized such that the tip 24 may pass through the central aperture 136 and engage the ejection unit 56. Protruding into the central aperture 136 from a wall of the frame structure is an engagement tab 146. The engagement tab 146 may be located on the side of the central aperture 136 that is opposite the location of the latch slide body 128. The engagement tab 146 may be sized to fit into and engage a retention feature 123 on the tip 24. The engagement tab 146 may have a chamfered surface 147 which is positioned between the inner most surface of the engagement tab and the surface of the engagement tab 146 which faces in the direction of the handle head 74. In this position, the contact between the engagement tab 146 and tip 24 may be a gradual engagement as the tip 24 is inserted into the central aperture 136.

The latch aperture structure 140 may include a ramped contact surface 141. The ramped contact surface 141 may contact the slide body ramped surface 121. The engagement between the ramped contact surface 141 and the slide body ramped surface 121 may be such that as the switch slide body 128 translates longitudinally relative to the housing 48, the slide body ramped surface 121 forces the ramped contact surface 141 in a transverse direction (i.e. in a direction perpendicular to the longitudinal axis of the handle 48) relative to the handle. The latch aperture structure 140 may be moved transversely by moving the switch slide body 128 longitudinally with respect to the handle. The latch aperture structure 140 may be posited between a first latch wall 144 and a second latch wall 145. While these walls are shown in FIGS. 5B and 5C as part of the housing segment 50 other latch walls may similarly position the latch aperture structure 140 relative to segment 52. With these latch walls 144/145 (and opposing walls in segment 52) the movement of the latch aperture structure 140 in the longitudinal direction may be limited or eliminated allowing for only a transverse motion of the latch aperture structure 140.

The latch aperture structure 140 may include a spring feature 142 (illustrated in FIG. 5A-C and FIG. 7 as 142A and 142B). The spring feature 142 may be supported by one or more platforms. For example, handle housing 48 may include interior surfaces that define one or more platforms such as platforms 143A and 143B. The spring feature 142 may have a first arm 142A which contacts a first platform 143A and a second arm 142B which contacts a second platform 143B. It may be noted that the spring feature 142 may be any structure operable to return the latch aperture structure 140 back to a laterally biased position. For example, a laterally biased position may be one in which the engagement tab 146 engages the retention feature 123 when the tip 24 is fully inserted into the ejection unit 56 and the collar unit 58. In this position the switch slide body 128 may be moved away from head 74 allowing the slide body ramped surface 121 and the ramped contact surface 141 to engage in a way that the spring feature 142 is either fully relaxed or partially relaxed. By moving the switch slide body 128 longitudinally toward the head 74, as discussed above, the latch aperture structure 140 may move transversely across the housing 48. This movement may disengage the engagement tab 146 from the retention feature 123 and also compress spring feature 142. The compression of spring feature 142 will have the reactive force which attempts to re-engage the engagement tab 146 with the retention feature 123 and also slide the switch slide body 128 longitudinally away from the head 74. It may be noted that the system may also be reversed merely be reversing the slopes of the slide body ramped surface 121 and the ramped contact surface 141 allowing the tip to disengage by sliding the switch slide body 128 away from head 74 and allowing the tip to re-engage by sliding the switch slide body 128 toward head 74.

With continuing reference to FIGS. 5A-C, the operation of attaching and detaching a tip 24 from the handle 26 will be described. A tip proximal end 162 is inserted into the first fluid passage 72 (the fluid passage through the collar unit 58 and into the ejection unit 56) through the opening in the handle head 74. As the tip 24 is inserted, the tip 24 passes through the latch aperture structure 140 and is received within the collar surface 76 in the collar unit wall 100. By pushing tip 24 into the latch aperture structure 140, the chamfered surface 147 slides along the sloped surface 163 of the tip proximal end 162, thereby pushing the engagement tab 146 out of the retention feature 123. As the engagement tab 146 is pushed out of the retention feature 123, the spring 142 is compressed against one or more of platforms 143A/B. As the tip 24 continues to be inserted within the first fluid passage 72, the tip annular ring 124 formed on the tip exterior engages the handle head's recessed surface 120.

To detach the tip 24 from the handle 26, the latch 28 is pressed towards the handle 26. When the latch 28 is pressed, the engagement tab 146 received within the tip retention feature 123 moves away from the retention feature 123. Once no portion of the engagement tab 146 remains within the retention feature 123, the first spring 112 expands. As the spring 112 expands the plunger 86 forces the tip 24 away from the handle head 74. This is able to occur because the plunger 86 and tip 24 contact one another on the proximal end 162 of the tip 24. This motion forces the tip 24 longitudinally along the handle 48 and out of the head 74. As the tip 24 moves upward, the tip retention feature 123 moves upward, and thus is no longer aligned with the engagement tab 146. Once the retention feature 123 ceases to be aligned with the engagement tab 146, the tip 24 may be removed from the handle 26 since it is no longer coupled to the handle 26 by the latch 28.

The handle 26 components of the embodiment may include the first and second handle housing segments 50, 52, the tube 34, the latch 28, the handle head 74, the collar unit 58, the ejection unit 56, the tube clamp 98, and plunger O-ring 80, and the springs 112 and 142. The first and second handle housing segments 50, 52 may separate in order to receive the collar unit 58, the latch 28, the tube clamp 98, a portion of the tube 34, the ejection unit 56 and plunger O-rings 80.

Semicircular notches may be formed in each of the first, second, third and fourth interior walls 60, 62, 64, 66 extending from the first and second handle housing segments 50, 52 cooperate to form first, second, third, and fourth handle housing apertures, respectively. When the first, second, third and fourth interior walls 60, 62, 64, 66 of the first handle housing segment 50 abut the first, second, third, and fourth interior walls 60, 62, 64, 66 of the second handle housing segment 52, the semicircular notches each such interior wall align with the corresponding notches formed in the mating interior wall. Thus, each of the aforementioned handle housing apertures are generally circular in shape, although in alternative embodiments the handle housing apertures may be of any desired shape.

The first, second, third, and fourth interior walls 60, 62, 64, 66 extending from the interior surfaces of the handle housing segments 50, 52 may each have a length generally parallel to the lengths of the other interior walls. The interior walls 60, 62, 64, 66 may generally be located along the lengths of their respective handle housing segments 50, 52 such that when the first and second handle housing segments 50, 52 are joined, the notches in the first and second interior walls 60, 62 define a pair of co-axially aligned first and second handle housing apertures that may receive the tube 34, and the notches in the third and fourth interior walls 64, 66 define a pair of coaxially aligned third and fourth handle housing apertures that may receive the ejection unit 56 and the collar unit 58.

One or more pegs may extend from the interior surface of the first handle housing segment 50 and may be adapted to mate with a corresponding hole in the second handle housing segment 52. The pegs and the holes may be dimensioned such that each will relatively snugly fit within its corresponding hole. The friction resulting from this fit may resist decoupling of the handle housing segments 50, 52. Alternatively and/or additionally, the first and second housing segments 50, 52 may be joined using glue, epoxy, fasteners, sonic welding, any other known method for joining two items, or by a combination of known methods. For example, the pegs may be glued or adhered within the holes.

Still with respect to FIG. 5A-C, an interior fluid passage 180 may be formed within the hollow tube 34. At a first end, the interior passage 180 may be dimensioned so that an end portion of the tube 34 may be received on the arrowhead wall 94 of the ejection unit 56. The tube clamp 98 may be a generally cylindrical and likewise hollow. The tube clamp 98 may be slid over the exterior surface of the tube 34.

Figure 5D:
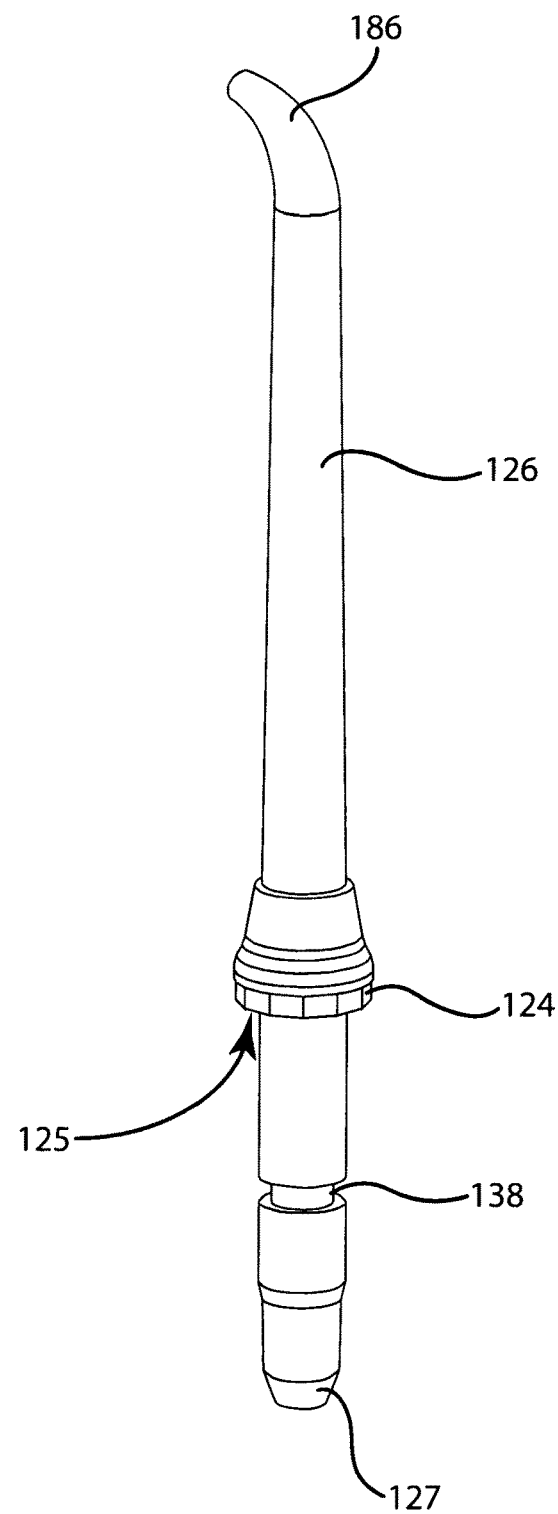
FIG. 5D depicts a perspective view of an embodiment of a tip.

As shown in FIG. 5D, the tip 24 may include an elongated, generally cylindrical shaft 126 that is bent or angled at a distal end 186. The inner surface of the tip shaft 126 may define a tip fluid passage, which may narrow along the tip shaft's length or at least near the distal end 186. The tip shaft 126 may include the tip groove 138. The tip groove 138 may also function as a retention feature 123, which may engage the latch 28 as described above, and the tip annular ring 124, which may extend around the tip shaft's circumference and engage the handle head 74 as described above. The tip annular ring 124 may have a plurality of flats that engage with the flats of recessed wall 122. The engagement between the flat surfaces may prevent or limit rotation of the tip 24 relative to the handle 26. The tip 24 may include a surface 125 which mates with recessed surface 120 limiting the distance that the tip 24 can travel into the handle 26. However it may be noted that the ejection unit may also limit the distance that the tip 24 can travel into handle 26 and may in fact bias tip 24 away from recessed surface 120. The tip 24 may include a tapered proximal end 127 which is configured to easily pass through o-ring 80.

Figure 8A:
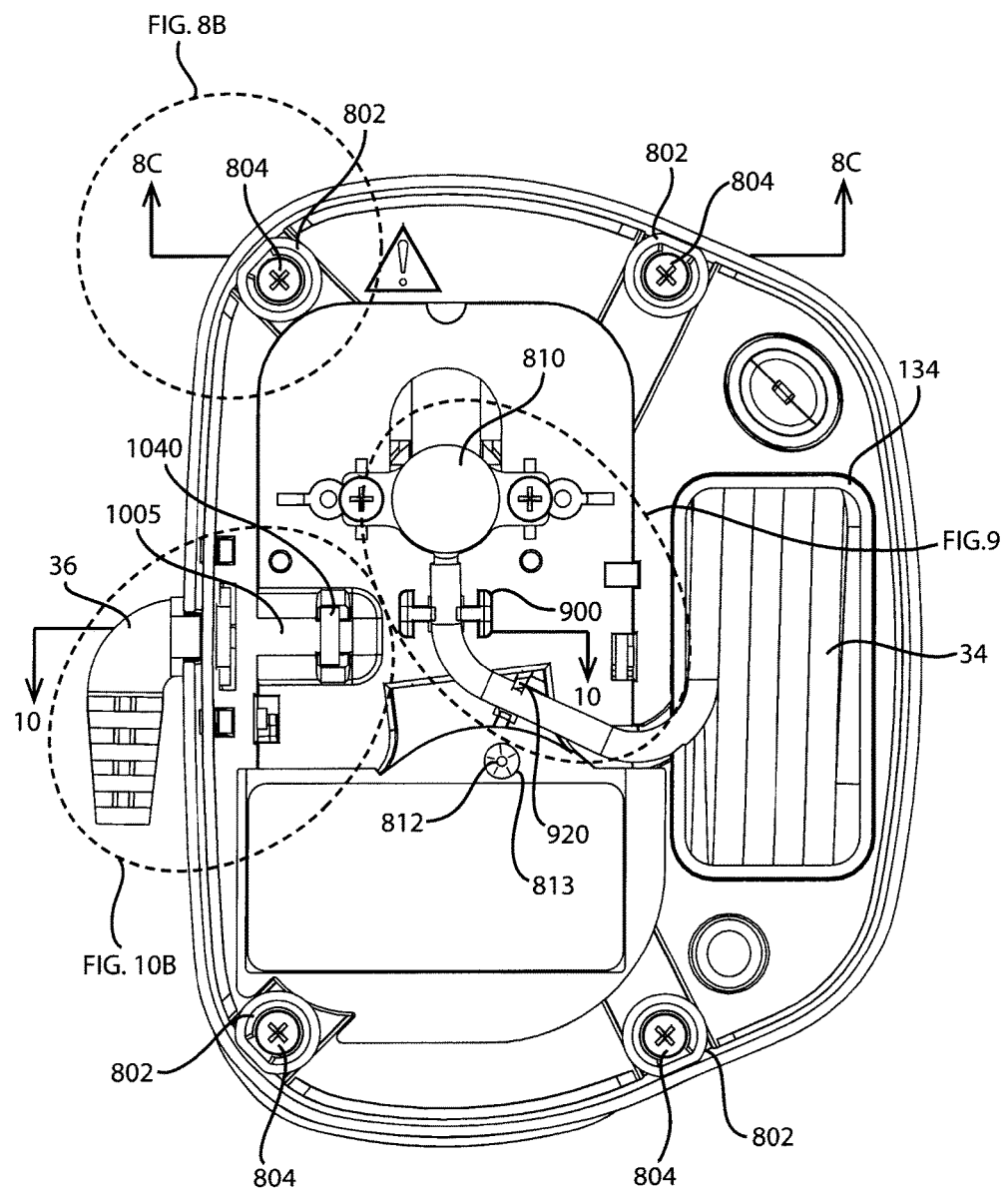
FIG. 8A depicts a bottom view of the apparatus shown in FIG. 1.
Figure 8B:
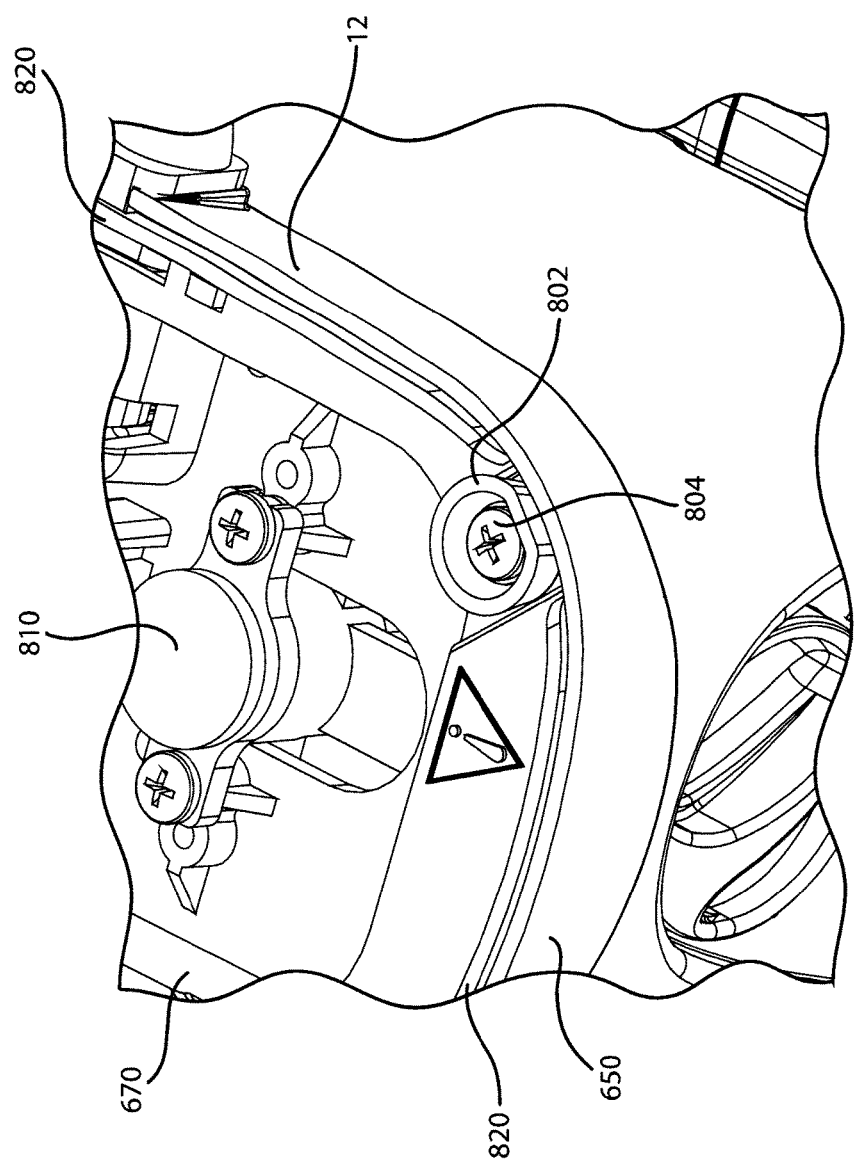
FIG. 8B depicts a sectional view of the bottom view of the apparatus shown in FIG. 8A.
Figure 8C:
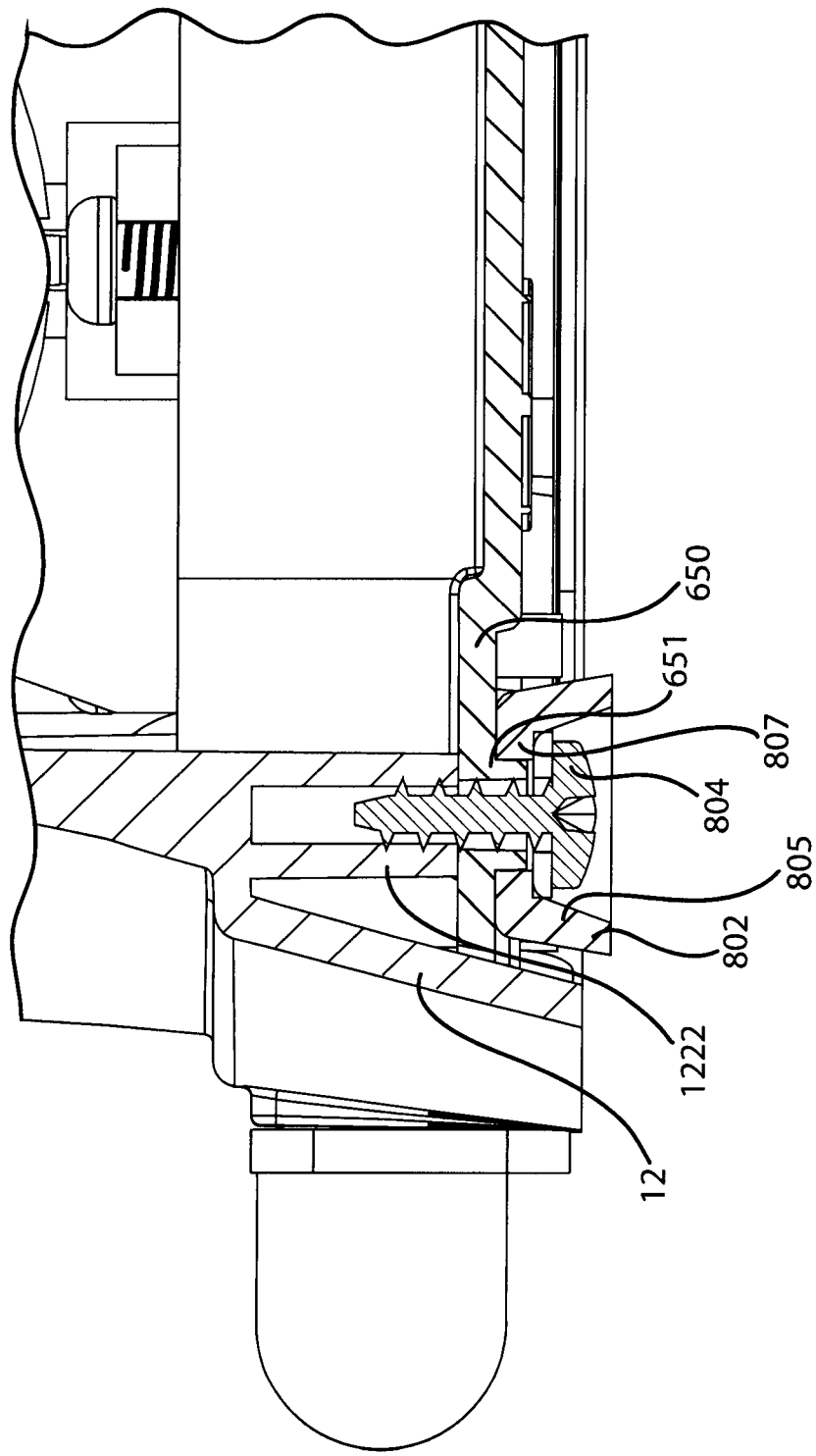
FIG. 8C depicts a cross-sectional view of a portion of the apparatus shown in FIG. 8B viewed along line 8-8 in FIG. 8B.
Figure 9:
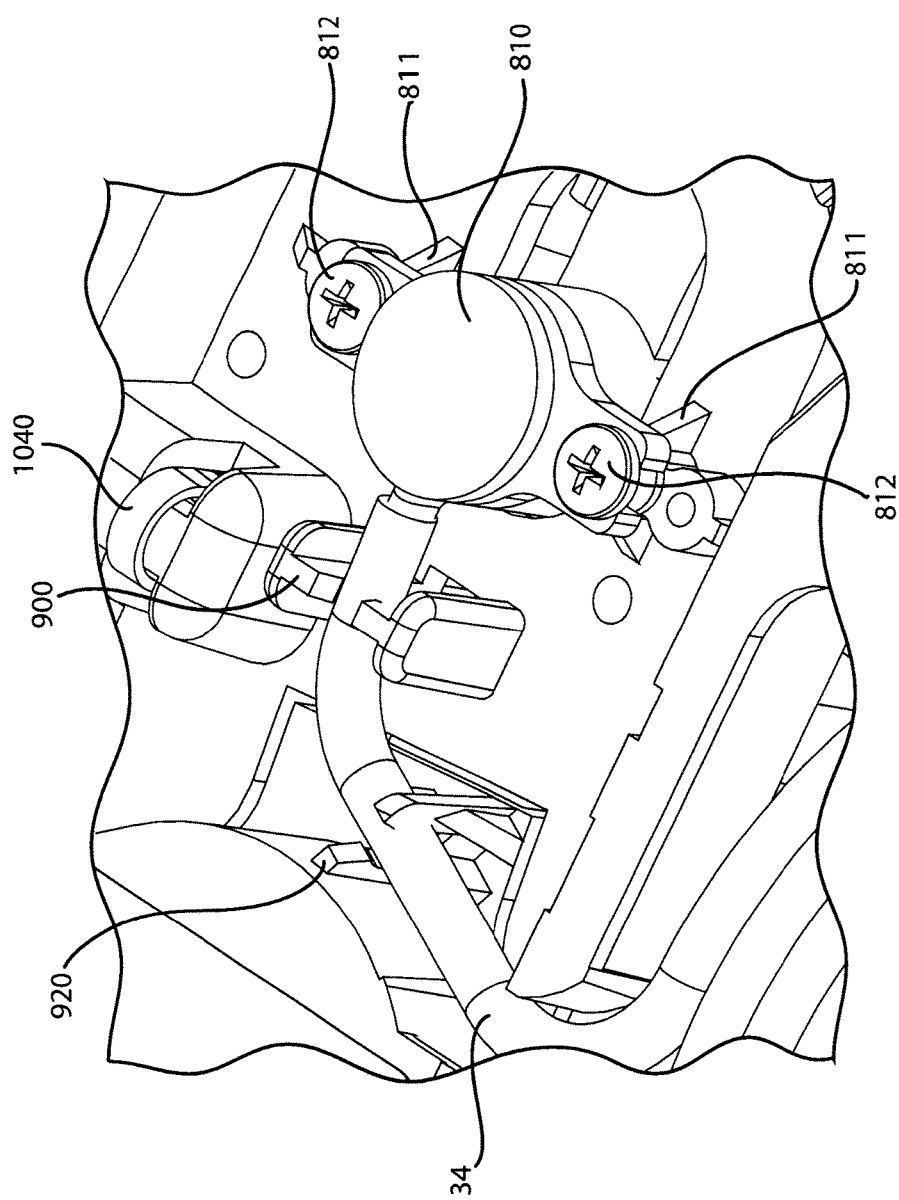
FIG. 9 depicts a sectional view of the tube and strain relief as depicted in FIG. 8A.

FIGS. 8-9 illustrate various views of the bottom of the base unit. Specifically, FIG. 8A depicts a bottom view of the apparatus shown in FIG. 1. The bottom of the base unit includes an aperture 134 open to the upper portion of the base unit and positioned adjacent to the tubing 34. As can be seen from the various figures, tubing 34 includes a substantial length of coiled tube such that that handle can be utilized away from the base unit. The coiled tubing 34 may be stored above aperture 134. The end of the coiled tubing 134 may pass through the aperture 134 and engage a pump outlet 810. The tubing 34 may be restrained as it is directed between aperture 134 and the pump outlet 810. For example clamps 900 may be molded into the bottom of the base unit with a gap sufficient for the tubing 34 to be pressed between two of the clamps 900. The clamps 900 may be positioned adjacent to where the tubing 34 engages the pump outlet 810. A second set of clamps 920 may be positioned a short distance away from clamps 900. The second set of claims may be positioned at an angle to the first clamps 900 such that when tubing 34 is engaged between the second set of claims 920 the clamps cause tubing 34 to turn toward aperture 134. The tube 34 may be removably restrained by claims 900/920 such that the tube 34 can be removed from the clamps. Additionally tube 34 may be removably attached to the pump outlet 810 such that the tube 34 and the pump outlet 810 can be separated allowing the entire handle and tube to be separated from the base oral irrigator base unit 10 and ultimately be replaced or serviced. Additionally, as illustrated in FIGS. 8A and 9, the pump outlet 810 may include the fitting outflow 304, which mates with the tube 34. The pump outlet 810 may be connected to the pump or the base unit 12 using fasteners thereby enabling the pump outlet 810 to be selectively detached from the pump. Because the pump outlet 810 may be selectively detached from the pump, the handle 26 may be readily decoupled from the pump, thereby enabling replacement of the handle 26, if desired.

Elastomer supports 802 may be used to elevate the outer surface of the base unit above a surface upon which the base unit may be supported. Further vibration reduction for the pump may be obtained by use of elastomer supports 802 composed of rubber or other suitable vibration dampening material. FIG. 8C is a cross-sectional view, viewed along line 10-10 in FIG. 8A showing the connection between elastomer supports 802 and the bottom plate 650 of the base unit. The elastomer supports 802 may include a footing body. The footing body may include a flat surface 807 parallel with the bottom surface 650 of the base housing. The elastomer supports 802 may have annular walls 805 which extend from the flat surface. The elastomer supports 802 may be connected to the bottom plate 650 of the base housing by screws 804 that are coaxial with the annular walls and extend through the flat surface 807. The screws 804 may extend through the bottom plate 650 of the base unit and into a standoff attached to the housing 12 of the base unit thus attaching the bottom plate 650 bottom plate 650 of the base unit to the housing 12 of the base unit. The annular walls 605 may extend past the screw heads such that in response to being set on a flat surface the annular walls support the base housing and prevent or limit any contact between the flat surface and the heads of screws 804. The elastomer supports 802 may be generally cylindrical and may include a recessed surface from which a generally circular footing wall 805 may extend. However it may be noted that the elastomer supports 802 may be any shape sufficient to support the base unit. In various embodiments the elastomer supports 802 may be feet. The feet may be sliding resistant feet. The feet may be rubber to help resist sliding. The feet may reduce vibrations that may be transmitted from the oral irrigator base unit 10 to the surface supporting oral irrigator base unit 10.

Figure 10A:
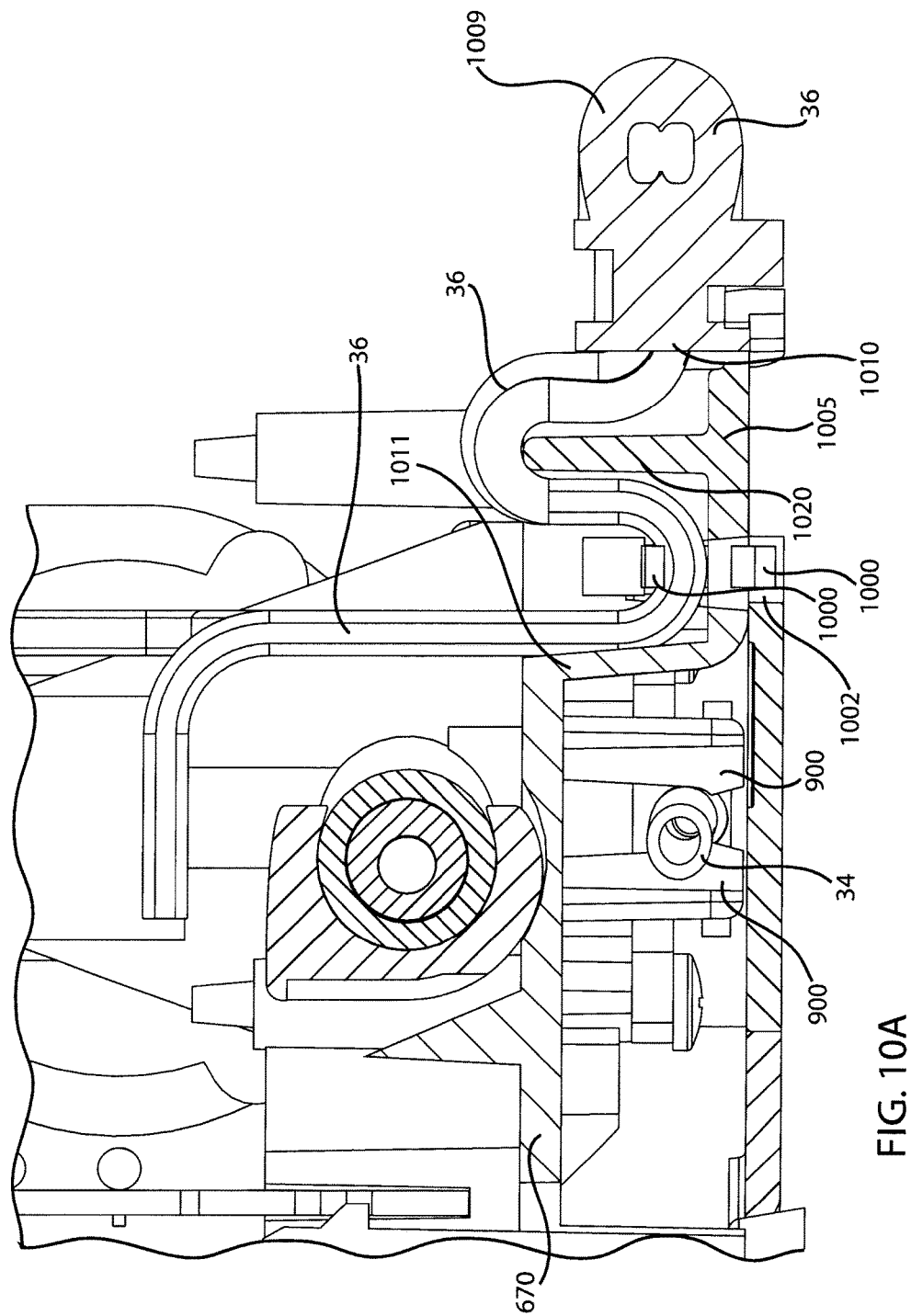
FIG. 10A depicts a sectional side view of the apparatus of FIG. 1 as viewed along line 10-10 in FIG. 2.
Figure 10B:
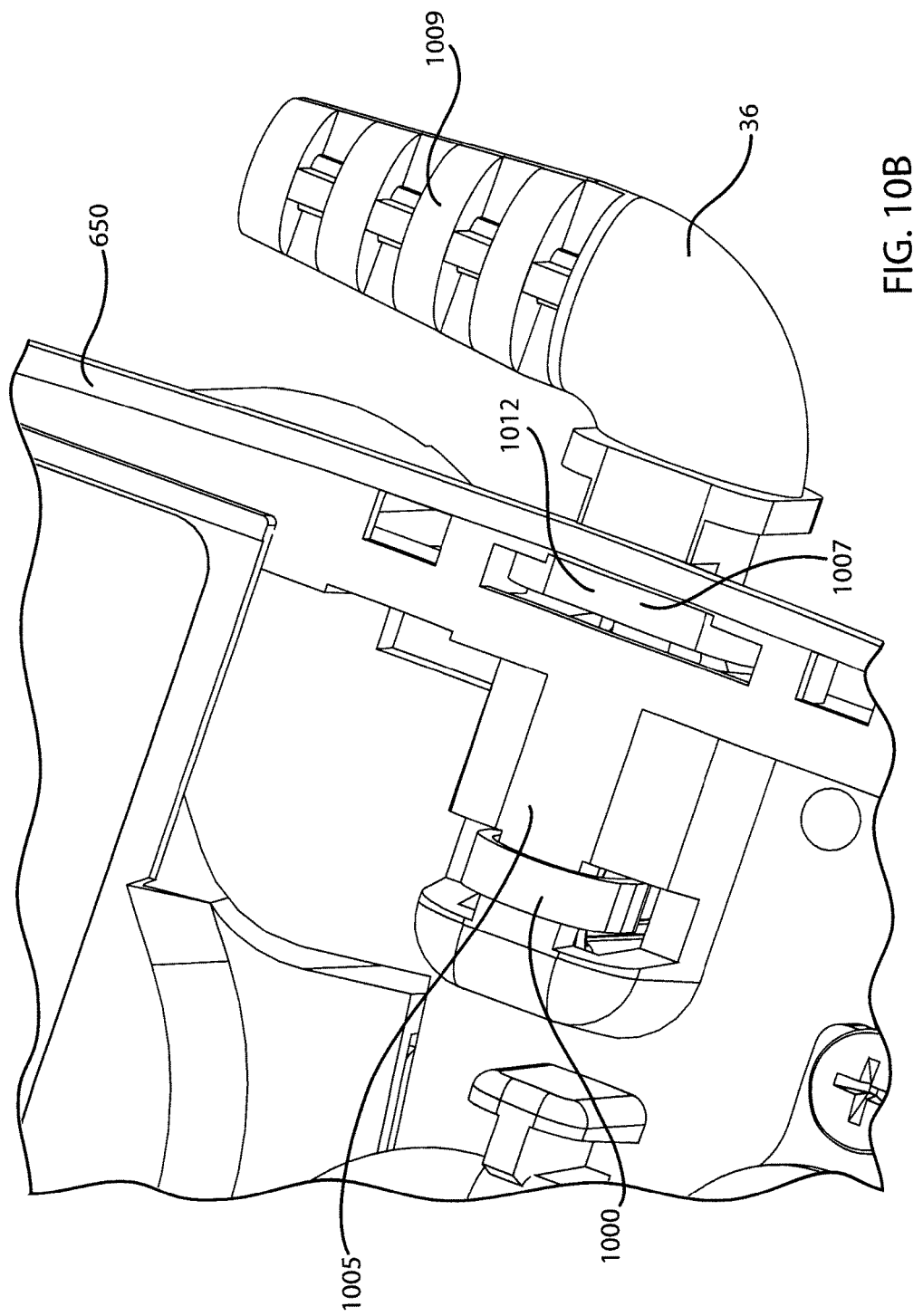
FIG. 10B depicts a bottom perspective sectional view of the power cord strain relief.
Figure 11A:
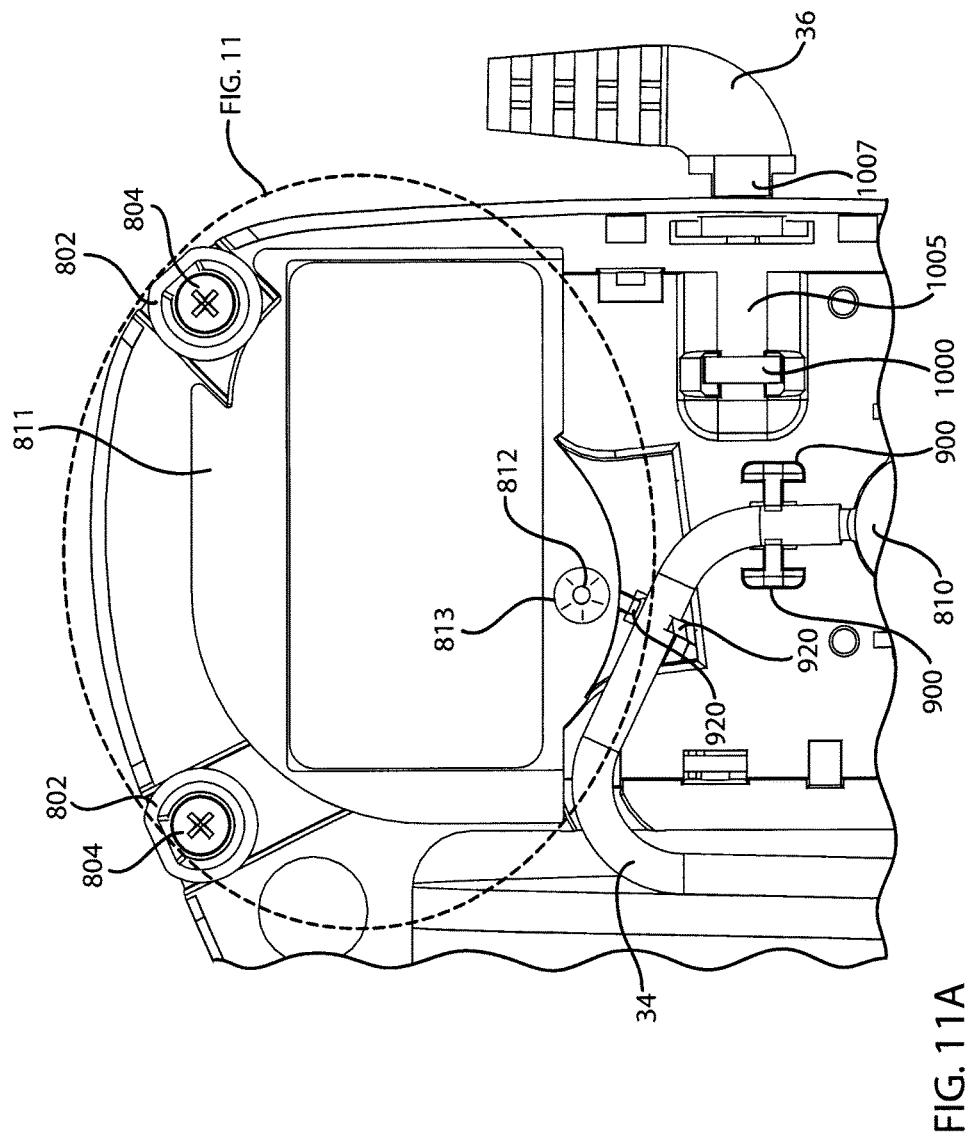
FIG. 11A depicts a bottom sectional view of the apparatus of FIG. 1.

As illustrated in FIGS. 10A-B and 11A, the power cord 36 or cable connects through the side of the base unit 12 wall. In some embodiments, the oral irrigator base unit 10 may include one or more strain relief features for the power cord 36. The cord 36 may include a relief collar 1010 where it passes through the base unit 12 wall. The strain relief 1009 forms a frustum shape that expands the diameter of the cord 36 as it nears the base unit 12. In some embodiments, the strain relief 1009 may be formed of a stiffer material than the cord 36. Additionally, due to the increased diameter of strain relief 1009, the strain relief 1009 acts to reduce strain on the cord 36 and the interior portion of the cord, which reduces wear on the cord over time. The oral irrigator base unit 10 may include a u-shaped power cord structure for receiving the power cord 36 into the base unit. A wall 1005 may extend out from bottom plate 650 as shown in FIG. 10B. The wall 1005 may define a strain-relief channel for cord 36. Relief collar 1010 on the strain relief 1009 may position the strain relief portion of the cord 36 relative to bottom plate 650. As shown in FIG. 10B, the relief collar 1010 may have flanges 1007. The cord 36 may follow wall 1005. A second wall 1020 may extend perpendicularly from wall 1005. The cord 36 may follow the second wall 1020 may making a 90 degree turn and traveling toward the top if oral irrigator base unit 10. At the end of wall 1020 the cord 36 may make a 180 degree turn back toward wall 1005. At wall 1005 the cord 36 may make a second 90 degree turn and follow wall 1005 once again. The cord 36 may be restrained against wall 1005 after this second 90 degree turn by a zip tie 1000 which passes through aperture 1002 and around cord 36. Thus the cord 36 forms a U shape around wall 1005. The path limits the ability of the cord 36 to be pulled out of oral irrigator base unit 10 or for the cord interior connections to be stressed. The cord 36 may make and additional turn back to the interior of oral irrigator base unit 10 when the cord reaches wall 1011 which is part of bottom shelf 670. The walls 1005, 1020, and 1011 may generally be configured to correspond to a desired position of the cord 36. For example, the second channel walls may be a curved semi-circle that defines a bend in the cord 36. The shape, dimensions, and configurations of the cord channel and the channel walls may be varied based on the desired position, bending strength, and other factors of the cord and interior cord. Bottom plate 650 may include apertures 1012 for receiving flange 1007 and restraining the cord 36 against bottom plate 650.

Figure 11B:
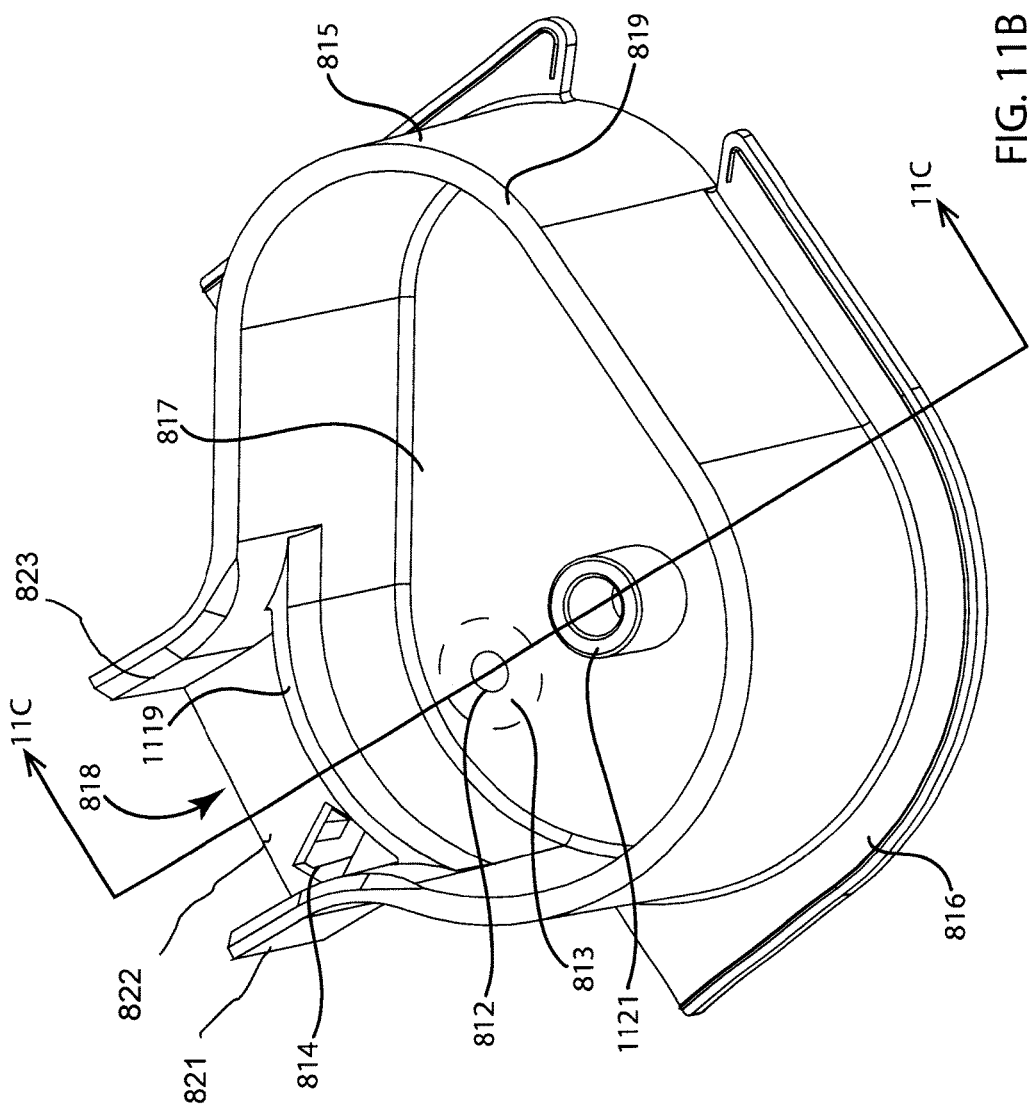
FIG. 11B depicts a perspective view of the gear housing cover as shown in FIG. 11A.
Figure 11C:
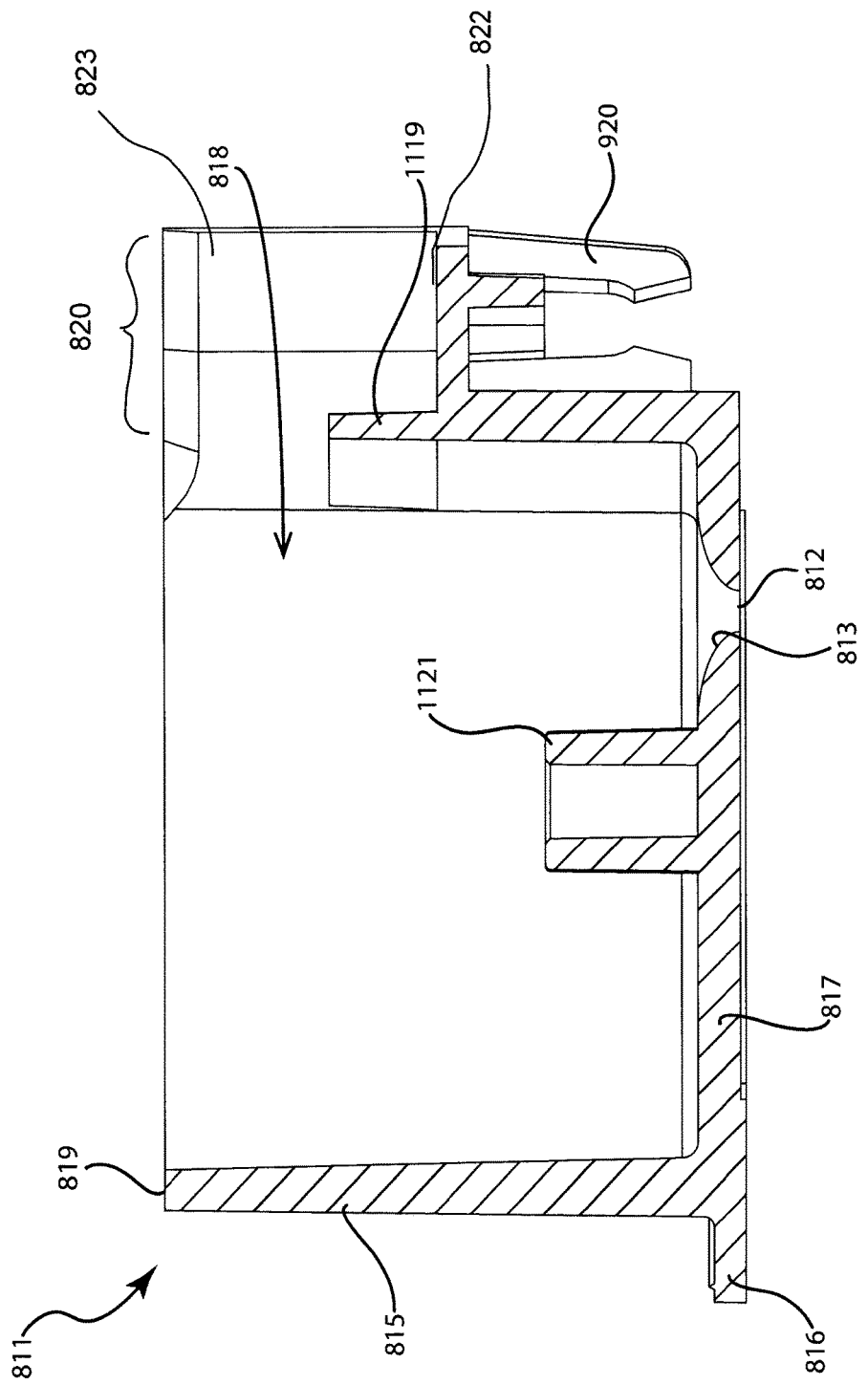
FIG. 11C depicts a cross section view of the gear housing cover of FIG. 11B as viewed along line 11C-11C.

As illustrated in FIG. 11A-C, a gear housing cover 811 may be attached to the bottom of the oral irrigator base unit 10. In various embodiments the gear housing cover 811 may be attached to the bottom shelf 670 and/or the gear housing 680. The attachment between the gear housing cover 811 and the bottom shelf 670 and/or the gear housing 680 may be a contiguous attachment wherein the gear housing cover 811 and the bottom shelf 670 and/or the gear housing 680 form a single part or the gear housing cover 811 may be removably attached to the bottom shelf 670 and/or the gear housing 680. The gear housing 680 and a gear housing cover 811 may form a cavity which contains the gearing 1118, 1130 and linkage to the plunger assembly including the piston 1105 and piston housing 1320 shown in FIG. 11D. As illustrated in FIG. 11A, which depicts a bottom sectional view of the apparatus of FIG. 1, a drain hole 812 may be positioned in the bottom of the gear housing cover 811. The drain hole 812 may be a part of depression 813 which surrounds drain hole 812. Depression 813 may be operable to collect and funnel liquids toward drain hole 812 for expulsion from the gear housing cover 811. The drain hole is discussed in more detail below.

Figure 14:
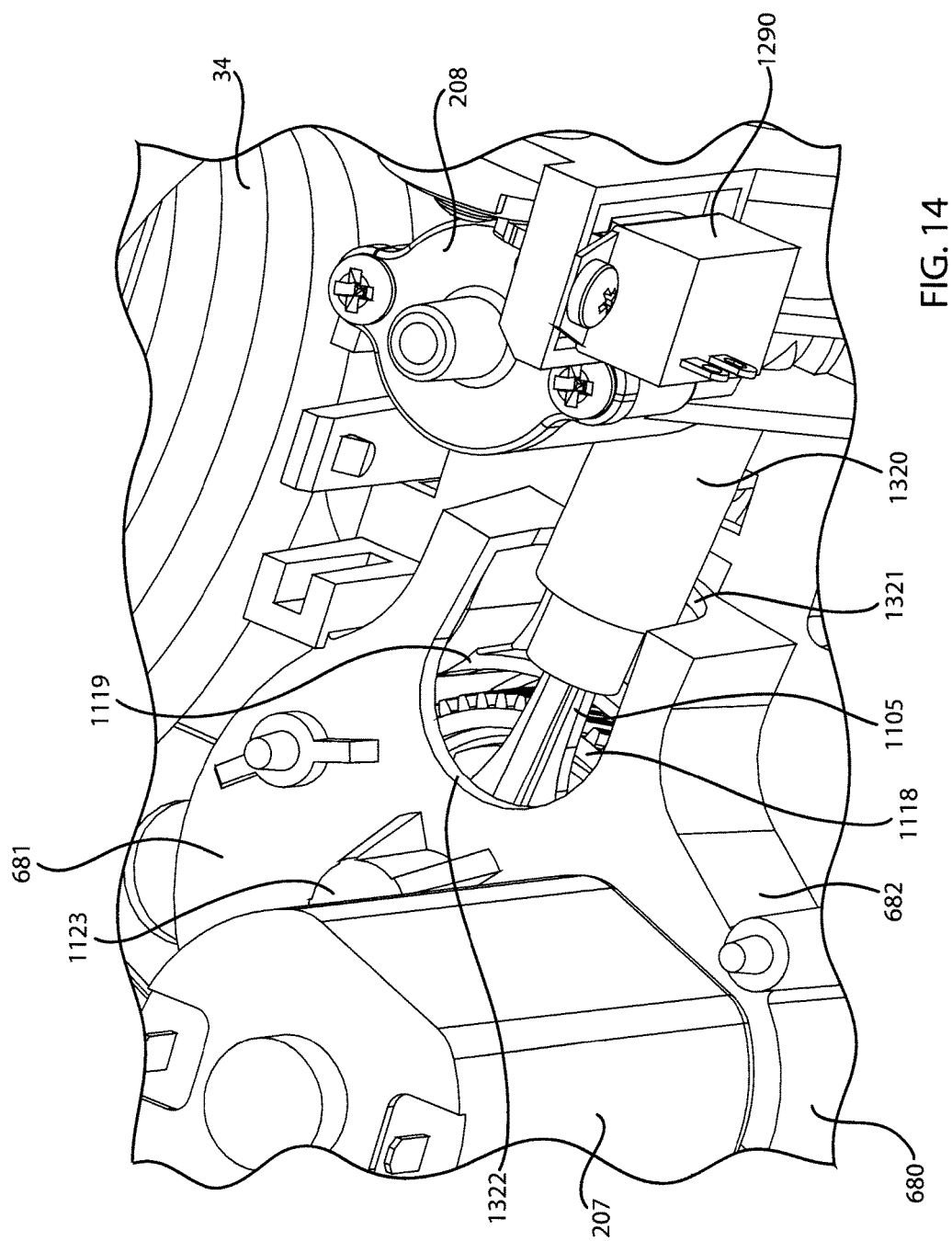
FIG. 14 depicts a sectional view of the partial assembly, perspective view of the apparatus depicted in FIG. 13 with the shield removed.
Figure 15:
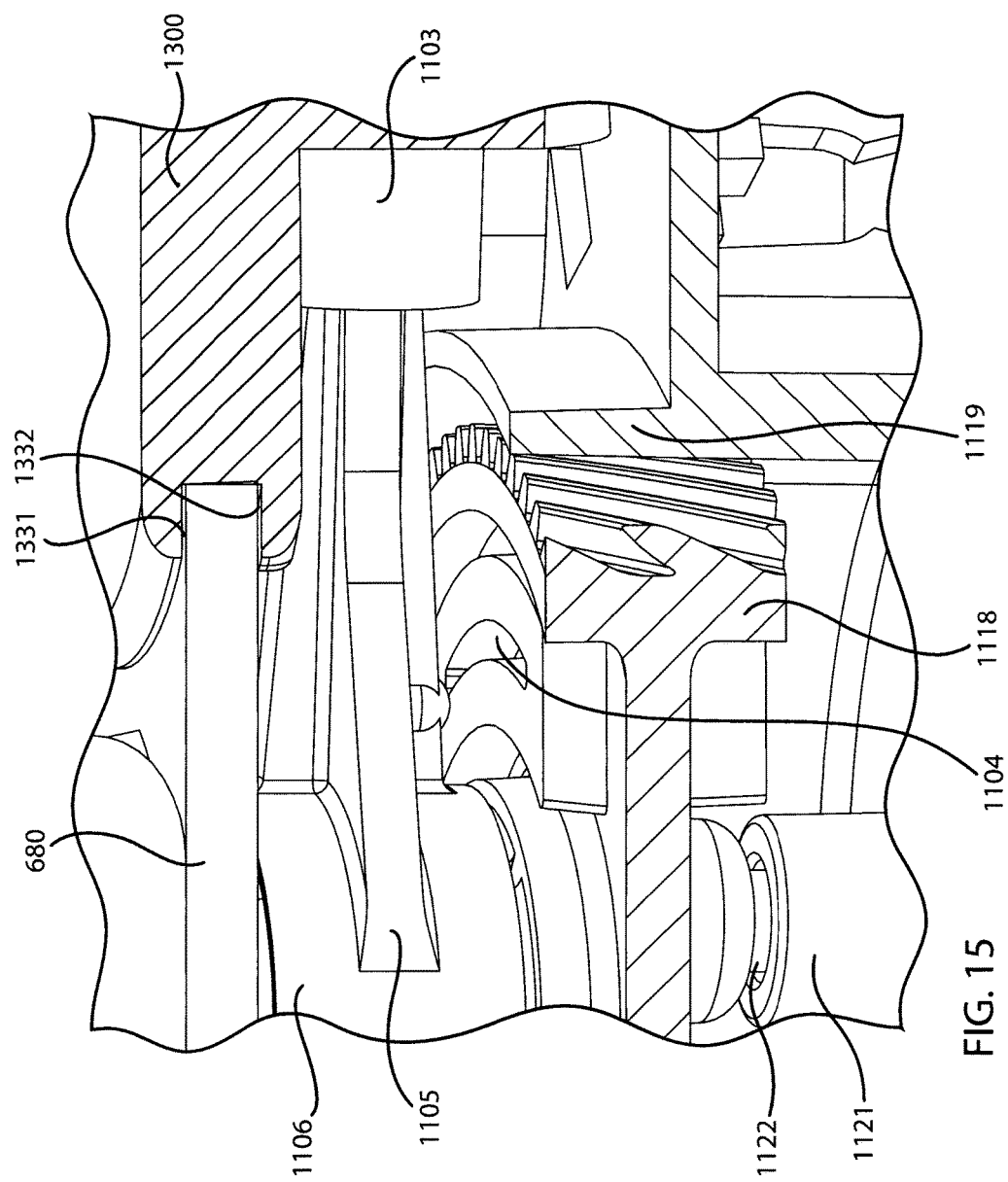
FIG. 15 depicts a cross section view of the partial assembly of FIG. 14 as viewed along the line 15-15 in FIG. 13.

As illustrated in FIG. 11B-C, which depicts a perspective view and cross section view of the gear housing cover 811 as shown in FIG. 11A, the gear housing 811 may include a gear housing exterior wall 815 which is sized and shaped to closely surround the gears 1118, 1130 in the gear housing. The gear housing exterior wall 815 may extend perpendicularly from a bottom surface 817. An annular support protrusion 1121 may extend from the bottom surface 817 and be operable to support gear 1118. The gear housing exterior wall 815 may include a top surface 819. The top surface 819 mates with an inside surface of top wall 681 forming the interior cavity which houses the gears 1118, 1130 and a portion of the linkage to the plunger assembly including 1105/1320. The gear housing cover 811 may also include a flange 816 that extends coplanar with bottom surface 817 and away from and perpendicular with exterior wall 815. Wall 815 may extend around the majority of the perimeter of the gear housing cover 811, however an opening 818, may extend through a portion of the wall 815 near the top surface 819. The opening 818 may allow the linkage to the plunger assembly 1105/1320 to pass through wall 815 in order to connect with the gears 1118, 1130 housed within the gear housing cover 811. In various embodiments, the opening 818 may be defined by a protrusion 820 having side wall 821, bottom wall 822, and side wall 823. Each of the walls 821, 822, and 823 extend from the gear housing exterior wall 815. As shown in FIG. 11C this protrusion 820 may include a vertical wall 1119 (which is also shown in FIGS. 14 and 15). The vertical wall 1119, discussed in more detail below, may aid in containing contaminants and debris from the gears 1118, 1130.

In accordance with various embodiments, the gear housing cover 811 may include one or more drain holes. For example, bottom surface 817 may include drain hole 812. The drain hole 812 may be a part of depression 813 which surrounds drain hole 812 as discussed above. Bottom wall 822 may also include a drain hole 814. As the pump operates some water from the pump gets into the gear housing and may mix with gear oil and/or debris found in the gear housing (e.g. material that accumulates due to wear on moving components). The drain holes enable drainage of the water, oil, and/or debris from the gear housing and limit the ability of contaminated water from re-entering the system.

Figure 11D:
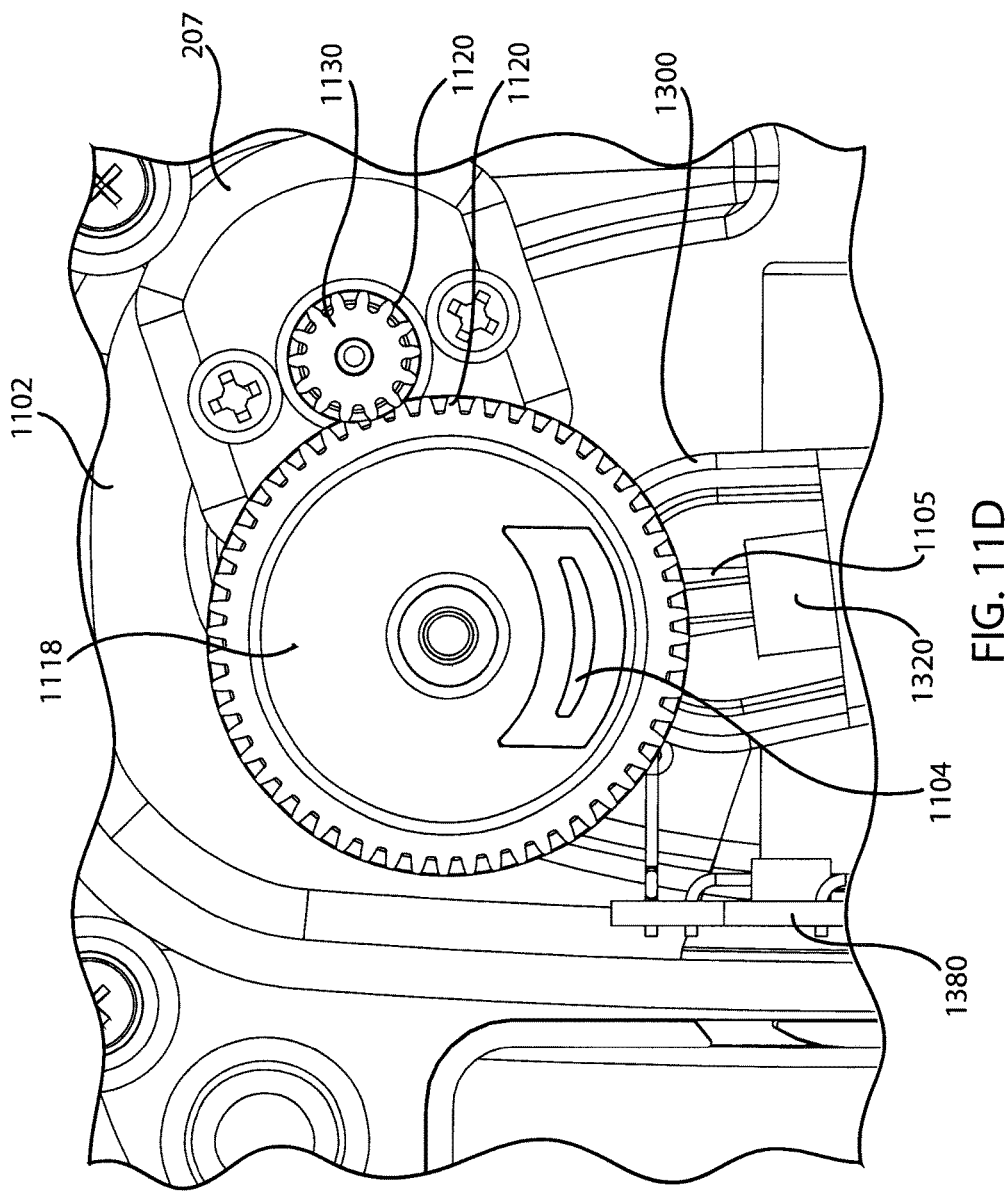
FIG. 11D depicts bottom sectional view of various components (e.g. drive gears) of the apparatus depicted in FIG. 1 with the gear housing cover removed for viewing of gears.

FIG. 11D is. As illustrated in FIG. 11D, which shows a bottom sectional view with the gear housing cover 811 removed from the bottom of oral irrigator base unit 10, the gear housing 680 may contain a plurality of gears. The first gear 1130 may be connected to the motor 207 (see also FIG. 18), and the second gear 1118 may engage the first gear 1130. The piston 1105 may be connected to the second gear 1118 by a second gear shaft (not shown) extending from the second gear 1118. The longitudinal axis of the second gear shaft may be eccentric to the axis about which the second gear 1118 rotates. The second gear 1118 may also include slot 1104. The first gear 1130 and the second gear 1118 may include helical teeth. The piston 1105 may be received within the piston housing 1320 connected to the pump body 208. A seal 1300 may separate the interior cavity of gear housing 680 from the interior of oral irrigator base unit 10 wrapping around the piston housing 1320.

Figure 12:
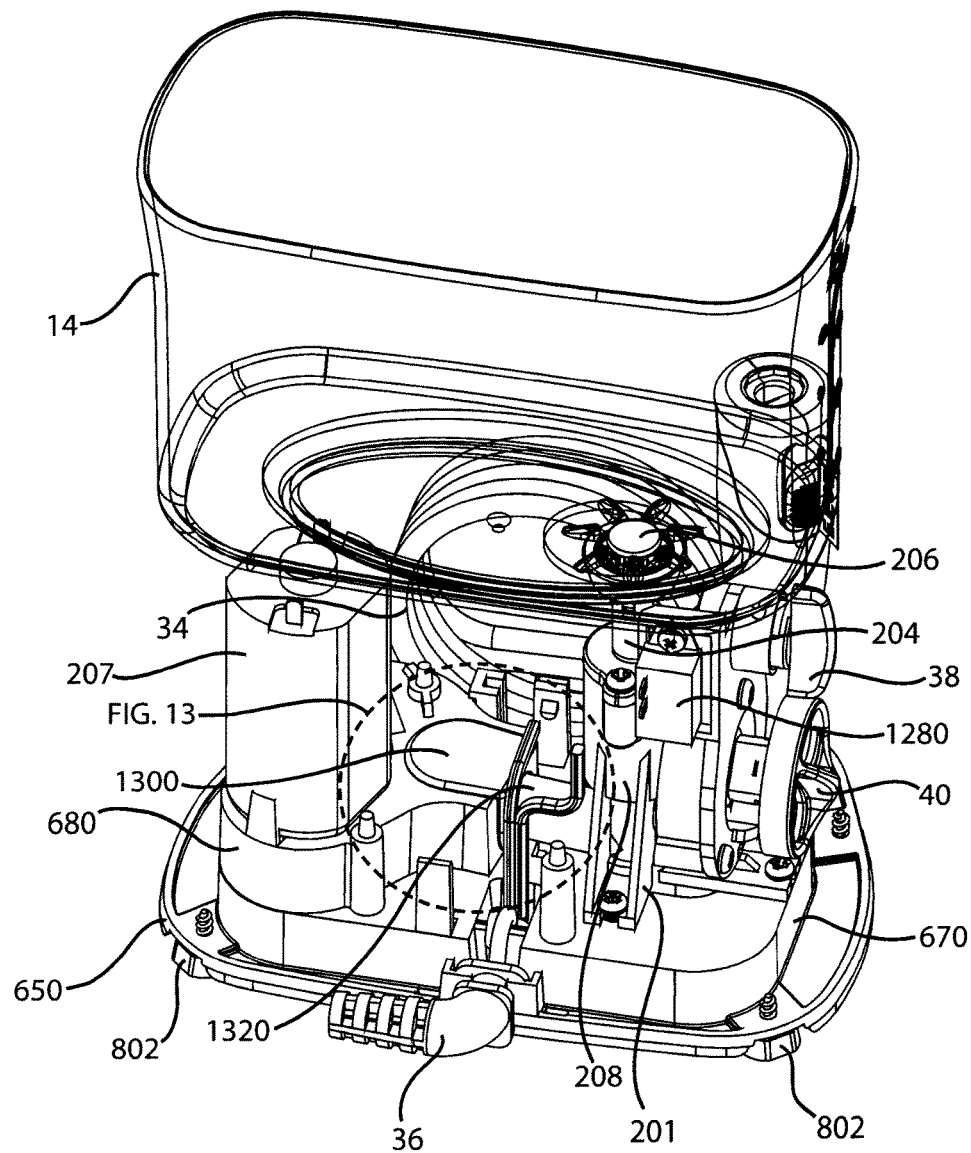
FIG. 12 depicts a partial assembly, perspective view of the apparatus depicted in FIG. 1.

FIG. 12 is a perspective view of the embodiment depicted in FIG. 1 with the base unit housing 12, not shown to better show the internal system. With reference to this figures, the base oral irrigator base unit 10 contain the motor 207 positioned above a gear housing 680. The gear housing 680 may be attached to a bottom shelf 670. As discussed in more detail later the bottom shelf 670 is a recessed portion of the bottom surface of the base housing. The recessed portion provides access to certain serviceable components from the bottom of the apparatus 10. The pump body 208 may be supported by a pump bracket 201 below. Knob 40 is shown positioned on the front of the unit and is operable for adjusting the fluid pressure delivered to the tip 24 by the pump. A reservoir valve 206 may be connected to a tube stand 204, as described in more detail below. The tube stand 204 may be connected to a pump inlet body 202, which may be connected to a pump body 208 with fasteners. A piston 1105 (not shown), received within the piston housing 1320, is associated with the pump body 208 as described in more detail below. A seal 1300 may separate the interior cavity of gear housing 680 from the interior of oral irrigator base unit 10 shown in FIG. 12. The pump 208 may include pump bracket 201 that support the pump. The oral irrigator base unit 10 may include a switch 1280 which is associated with the switch 38.

In accordance with the various embodiments as discussed herein, the oral irrigator base oral irrigator base unit 10 is arranged in a compact packaging particularly in comparison to other oral irrigators. The relationship of the motor to gear box to circuit card to pump assembly to switches are depicted in FIGS. 2, 3, 11, 12, and 14. As discussed in more detail below, the motor 207 may be a high voltage direct current motor which operates on 120V alternating current that is rectified to 170V direct current (DC). By operating a high voltage DC motor, the motor is able to be much smaller than a lower voltage DC motor while still being able to operate the pump at similar levels. The decrease in motor size enables the motor to be positioned closer to the circuit card and/or the pump assembly. The decrease in motor size also enables the motor to better fit between 681 and the top of the base unit housing under reservoir 14. As shown in FIG. 11D, the motor is separated from the pump by driven gear 1118 which drives piston 1105 within the piston housing 1320. The piston 1105 and the piston housing 1320 are connected to the pump 208 as depicted in FIG. 12. As such, due to this stack up of components the motor is limited in its position. The motor may be positioned such that its distance from the pump is minimized. Having a smaller package aids in minimizing this distance. In various embodiments, the pump 208 may engage the driven gear 1118 at a location other than the opposite side of driven gear 1118 from where the piston 1105 extends. However, it may be noted that the motor 207 may be positioned opposite of piston 1105 if minimizing the package size is not a concern. In one example, as shown in FIG. 11D the pump may engage driven gear 1118 between 2 and 3 o'clock as viewed from the bottom of oral irrigator base unit 10. As the motor is positioned closer to the piston housing 1320 the motor approaches seal 1300. A smaller motor 207 housing diameter enables the motor to be positioned closer to seal 1300 and thereby be positioned closer to the other components enabling an overall reduction in the size of the oral irrigator base unit 10. As such, utilizing the high voltage DC motor 207 the motor is positioned such that the overall packaging of the components within oral irrigator base unit 10 is minimized.

Operation of the embodiment depicted in FIGS. 1-19 involves filling the reservoir 14 with a fluid (such as water) and supporting the filled reservoir 14 on the base unit 12. Once the filled reservoir 14 is supported by the base unit 12, fluid may flow through the opened reservoir valve 206 in the reservoir 14 to the pump body 208 as described above. The pump may be activated using the switch 38. Once activated, the piston 1105 will supply pressurized water to the tip 24 as described above.

Figure 13:
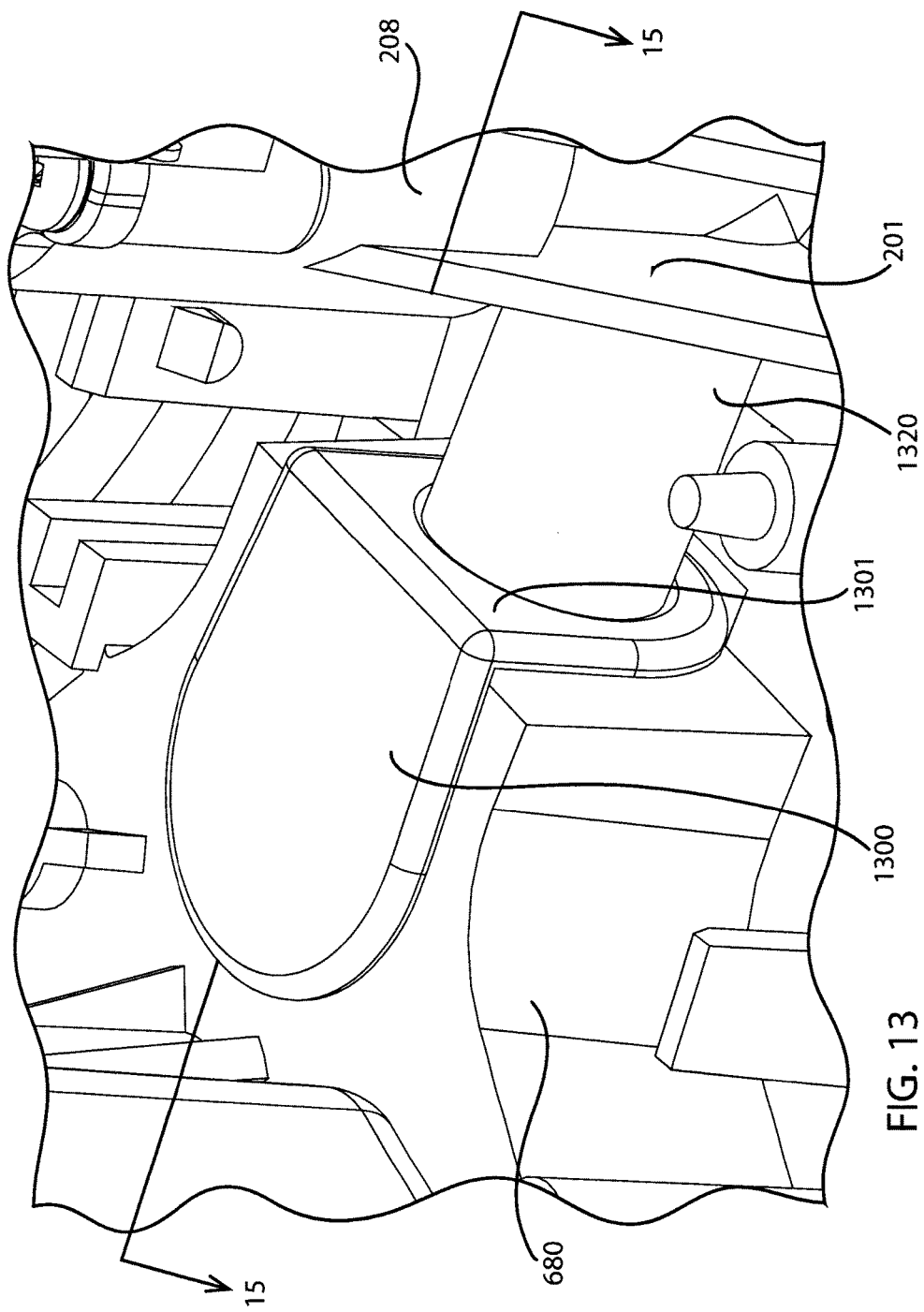
FIG. 13 depicts a sectional view of the partial assembly, perspective view of the apparatus depicted in FIG. 12.

As illustrated in FIGS. 13-15, the pump assembly may include piston 1105. Fluid flows from the reservoir 14 to the pump outlet 810 only on a backstroke of the piston 1105 connected to the pump outlet 810 through a piston housing 1320 (as described below). Suction generated by the piston 1105 backstroke pulls a check valve down within the interior of the pump. On a forward stroke of the piston 1105, positive pressure is generated in the pump outlet 810 (and, by extension, in portions of the present embodiment fluidly connected to the pump outlet 810). This positive pressure has several effects. First, it forces fluid out of the pump outlet 810. One end of the aforementioned tube 34 is connected to the pump outlet 810. Accordingly, fluid entering the pump outlet 810 may flow through the pump outlet 810, into the tube 34, through the handle 26, and ultimately into the tip 24 in order to irrigate or spray fluid into a user's mouth. Thus, fluid may be driven by the piston 1105 into the pump outlet 810 through the associated fitting and into the tube 34. Ultimately, and by means of the tube 34, the piston 1105 propels fluid into the tip 24, as well as out of the tip distal end 186.

Adjusting the flow control with knob 40 can vary fluid flow out of the pump outlet 810. It should be appreciated that by decreasing the fluid flow more fluid passes to a return channel and less fluid is available to enter the tube 34 from pump outlet 810. Accordingly, increasing the flow through the return channel diminishes fluid flow to the tip 24, which decreases the fluid pressure of fluid exiting the tip 24. In this manner, the user may directly control the volume of fluid exiting the reservoir 14 and being pushed by the piston 1105 through the tip 24. Thus, the user may control fluid flow out of the tip 24 by manipulating the flow control, which enables the user to control the fluid pressure of fluid exiting the tip 24.

In summary, the flow path for fluid during a backstroke of the piston 1105 follows. Fluid may exit the reservoir 14 through the reservoir opening 1410 in which the reservoir valve 206 resides, flowing into the tube stand. The fluid may enter the pump from the tube stand; flow into the interior pump and around the check valves, and into the pump outlet 810. The backstroke suction draws the check valve down within the interior pump chamber to permit fluid flow between the pump inlet fluid passage and interior pump. During a forward stroke of the piston, fluid may be propelled from the pump outlet 810, into the tube 34, through the handle 26, into the tip 24, and out of the tip distal end 186.

As illustrated in FIGS. 13-15, the oral irrigator may also include a gear housing orientation that helps to shield the electronic components from grease and water. FIG. 13 is a top perspective view of a section of the pump assembly. FIG. 14 is a top perspective view of a section of the pump assembly with seal 1300 removed. FIG. 15 is a cross-section of the oral irrigator illustrating the pump assembly through the seal 1300. The bottom plate 650 may include a recessed gear housing 680 that is positioned around the gears 1118, 1130. The gear housing 680 is extends over the gearing for the pump. The motor 207 is mounted outside of gear housing 680 with the drive shaft extending through the gear housing 680. In this configuration, the gear housing 680 prevents grease from the gears 1118, 1130 and other debris from the pump from affecting other components of the oral irrigator base unit 10. The gear housing 680 includes an aperture in the side wall 1321 which allows for the piston 1105 and piston housing 1320 to pass through the gear housing 680. Seal 1300 contacts all sides of aperture 1321 and piston housing 1320 completing the sealing off of the inside cavity of gear housing 680 from the rest of the oral irrigator base unit 10. Gear housing 680 includes a top wall 681 and side wall 682 which reduce water and grease from leaking out of the gear housing. The side wall 682 extending upwards from a bottom plate 650 and or bottom shelf 670. The side wall 682 generally traces the footprint of the gears 1118, 1130 and includes a side wall 682 between the location of the gears 1118, 1130 and the extension of the connecting rod and piston 1105 from the second gear 1118. For example, the connecting rod 1105 connects to the second gear 1118 and extends outward over the aperture 1321 in the side wall 682 to be received in the pump body 208. As shown in FIG. 15, the chassis 420 may further include a mounting hole 1104 for receiving a driven gear shaft to support the driven gear 1118 in the gear housing. Additional barrier wall 1119 may be included around the gears to further contain debris from the gears. Also shown is a hub 1106 of piston 1105 which receives the eccentric shaft of gear 1118. The gear housing seal 1300 extends into a cavity defined by the chassis 420 and the gear housing cover 680 and around the piston 1105 and connecting rod.

The gear housing seal 1300 may be any sealing material. In one example, the sealing material may be an elastomer or rubber due to their flexible nature and ability to form water tight seals. In one embodiment, the gear housing seal 1300 may be a cylindrically shaped with an annular seal extending around its outer surface. A first portion of the seal 1300 is received inside the cavity defined by the gear housing 680. The seal may extend out to connect to the pump body 208 or a portion of the pump such as the piston housing. In addition to sealing the gear housing and drive components of the pump, the gear housing seal 1300 further acts to provide vibration isolation and noise dampening, reducing the vibrations that are transmitted from the motor 207 and gears to the other components of the oral irrigator, as well as reducing the sound waves that are transmitted from the gear housing by absorbing them.

The piston 1105 is exposed to water as it operates. In some embodiments, the piston 1105 may be formed of a polyamide 6/10 (Nylon 6/10) material. This material has a higher dimensional stability and does not expand due to water absorption. This allows the pump to have an increased reliability as compared to conventional materials for the piston, as the wear resistance is improved along with the dimensional stability as the piston does undergo significant changes in size due to undesired water absorption.

As discussed above, in some examples, the gears 1118, 1130 may include helically oriented teeth. The first gear 1130 includes teeth helically shaped teeth that extend at an angle around the outer surface. Similarly, the driven or second gear 1118 includes teeth that are helically shaped. The helical shape of the teeth 1120 reduces noise and stress on the teeth as compared to straight cut gears. In particular, as the gears 1118, 1130 mesh and rotate, the teeth contact each other gradually along the length of a particular tooth. The helix angle of the teeth increases the gear-tooth contact ration, helping to ensure that at least two teeth on each of the gears 1118, 1130 are in contact at all times. On the contrary, with straight cut gear teeth, the contact ratio typically drops below two, such that only one tooth is engaged with the mating gear, increasing the load applied to the individual teeth. With the gears 1118, 1130 as described herein, the load applied to each tooth is reduced by at least half and the gear tooth deflection under load is also reduced by almost half. The reduction in gear deflection and because the load is applied gradually along the length of each tooth, noise is reduced during operation.

A support shaft 718 for the driven gear 1118 may be supported on both ends. As discussed above, the gear housing cover 811 may include an annular support protrusion 1121. A bottom end of the support shaft 1122 is received into the annular support protrusion 1121 from an interior side of the gear housing cover 811. The top end of the support shaft 1122 is then positioned within another support protrusion 1123 on the opposite side and formed into the top wall 681. In this manner the support shaft 1122 is anchored on both ends, helping to provide stability and strength to the driven gear 1118 as it rotates as it is driven by the first gear 1130.

Figure 16:
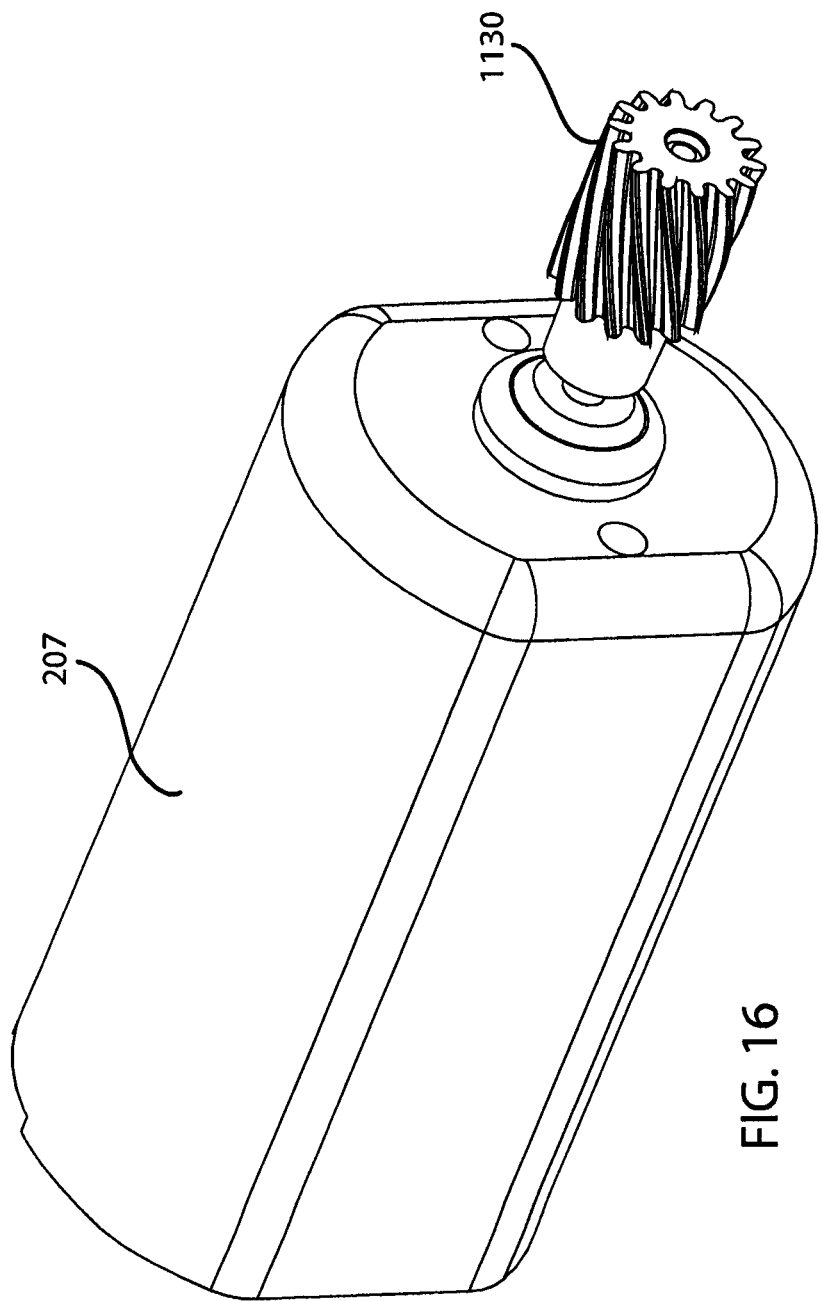
FIG. 16 depicts a perspective view of a drive motor of the apparatus of FIG. 1.

The motor and control assembly will now be discussed in more detail. FIG. 16 is a perspective view of the motor 207 for the oral irrigator. The motor 207 may be a high voltage direct current motor. In one example the motor 207 operates at 120V alternating current (AC) and is rectified to 170 V direct current (DC), without using a transformer. This allows the motor 207 to be compact and suited for high volume production, as the manufacturing processes for the motor 207 are automated, reducing manufacturing costs for the oral irrigator and improving reliability. In other embodiments, the motor 207 may be a 12 VDC motor with a switching/global power supply. The motor may include the first gear 1130 extending from the end. The first gear 1130 may have a length longer than the diameter.

Figure 17:
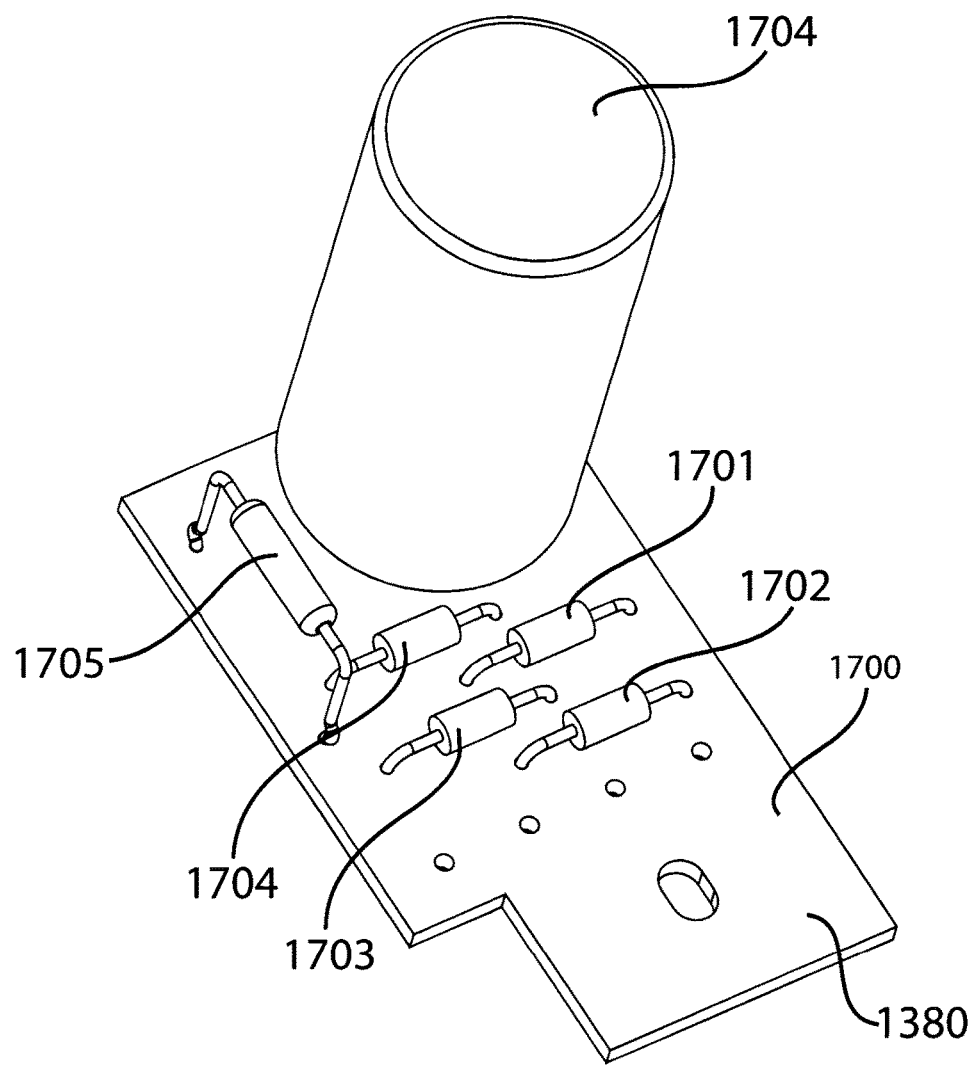
FIG. 17 depicts a perspective view of a rectifier circuit of the apparatus of FIG. 1.

With reference to FIG. 17, the rectifier 1380 may include a substrate 1700, such as a printed circuit board, four diodes 1701, 1702, 1703, 1704, a resistor 1705, and a smoothing capacitor 1704. The circuit 1380 helps to smooth the voltage signals applied to the motor 207 and the resistor 1705 and capacitor 1704 help to protect the diodes 1701, 1702, 1703, 1704 from in-rushes or spikes in the current.

Figure 18:
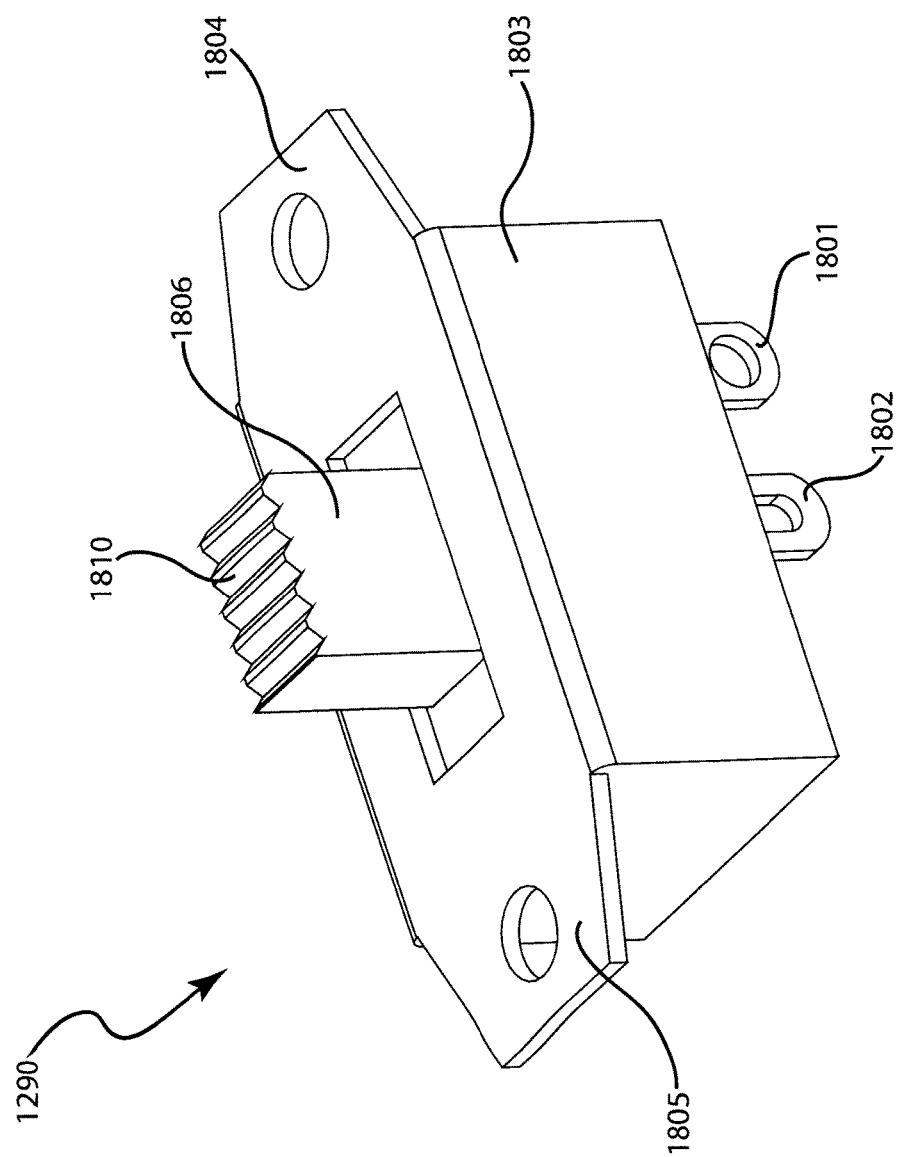
FIG. 18 depicts a perspective view of a switch as utilized in the apparatus of FIG. 1.

As illustrated in FIG. 18, a high current slide switch 1290 may reduce costs and improve reliability by leveraging automation and the expertise of the common switch manufacturers. The switch may include connectors 1802 and 1801 to connect to a power supply. A housing 1803 may enclose the interior contacts. Flanges 1805 and 1804 may be present for attaching the housing to a surface. Slide plate 1806 may be utilized to manipulate interior contacts. Teeth 1810 may be included to engage other mechanisms as discussed below.

Figure 19:
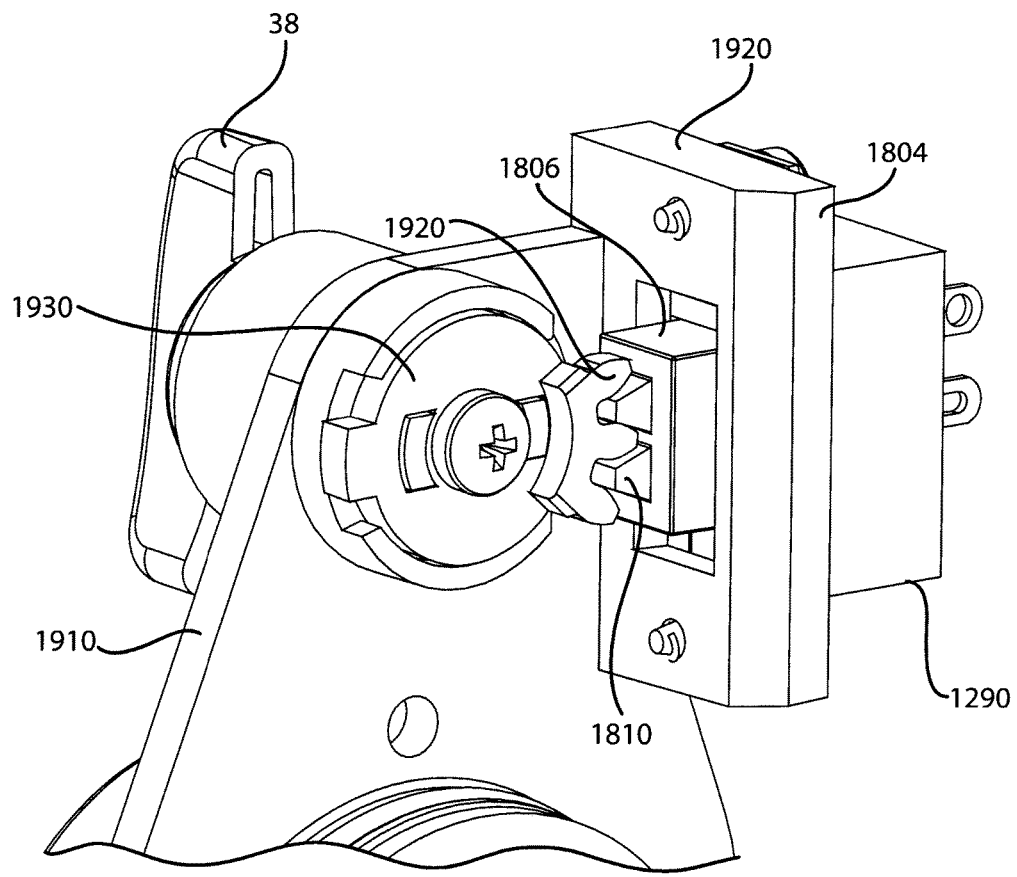
FIG. 19 depicts a perspective view of a power switch assembly as utilized in the apparatus of FIG. 1.

Operation of the pump depicted in throughout involves moving the switch 38 from the off position to the on position. With reference to FIGS. 18 and 19, switch 38 may comprise a switch body 1925, a switch plate 1930, and switch gear teeth 1920. This assembly allows a rotational force from the switch 38 to be translated to a linear force on plate 1806. When the switch 38 is moved, the switch plate 1930 is rotated causing the switch gear teeth 1920 to rotate. The switch gear teeth 1920 contact the connector switch body teeth 1810. The connector switch body teeth 1810 receive a force from the movement of switch gear teeth 1920 causing plate 1806 to linearly translate. This rack and pinion action between the switch plate teeth 1810 and the switch gear teeth 1810, respectively, transitions the contacts within the electrical circuit with the housing 1290. This transition of the contacts either closes or opens the circuit. Closing the electrical circuit permits electrical power from a power source to be supplied to system. As power is supplied to the switch 1290, the motor 207 is activated causing the first gear 1130 to rotate. As the first gear 1130 rotates, it causes the second gear 1118 to rotate. The rotation of the second gear 1118 causes the piston 1105 to move back and forth within the piston housing 1320. The back and forth motion of the piston 1105 causes pulsating, pressurized fluid to be supplied from the reservoir 14 to the tip 24 as described in more detail above. Switch body 1925 is located on support structure 1910. Wall 1920 extends perpendicularly from support structure 1910. Housing 1290 attaches to wall 1920 at a location to align teeth 1810 with the teeth 1920.

All directional references (e.g., upper, lower, upward, downward, left, right, leftward, rightward, top, bottom, above, below, vertical, horizontal, clockwise, and counterclockwise) are only used for identification purposes to aid the reader's understanding of the embodiments disclosed herein, and do not create limitations, particularly as to the position, orientation, or use of an embodiment unless specifically set forth in the claims. Joinder references (e.g., attached, coupled, connected, joined, and the like) are to be construed broadly and may include intermediate members between a connection of elements and relative movement between elements. As such, joinder references do not necessarily infer that two elements are directly connected and in fixed relation to each other.

In some instances, components are described with reference to "ends" having a particular characteristic and/or being connected with another part. However, those skilled in the art will recognize that embodiments are not limited to components which terminate immediately beyond their points of connection with other parts. Thus, the term "end" should be interpreted broadly, in a manner that includes areas adjacent, rearward, forward of, or otherwise near the terminus of a particular element, link, component, part, member or the like. In methodologies directly or indirectly set forth herein, various steps and operations are described in one possible order of operation, but those skilled in the art will recognize that steps and operations may be rearranged, replaced, or eliminated without necessarily departing from the spirit and scope of the present invention as claimed below. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A dental water jet comprises:
    a base housing enclosing a pump system driven by a piston and a motor which drives the piston, the base housing including a bottom wall;
    a gear housing attached to the bottom wall of the base housing, wherein the gear housing houses a first gear and a second gear, and includes a top wall, a bottom plate, and a side wall extending between the top wall and the bottom plate, wherein the top wall and the side wall extend around the first and second gears to enclose the first and second gears therebetween, wherein the first gear is attached to a motor shaft on the motor, wherein the motor is located above the gear housing and the motor shaft passes through the top wall of the gear housing and into the first gear wherein the first gear engages the second gear which drives the piston, wherein the gear housing is positioned at least partially below the bottom wall of the base housing;
    a drain hole located at the bottom of the gear housing operable to direct liquids out of the gear housing;
    a handle with a removable tip fluidly connected to the pump system;
    a fluid reservoir removably positioned on the base housing; and
    a tube which fluidly connects the pump system to the handle.

2. The dental water jet of claim 1, wherein the base housing is supported on a bottom surface by elastomer support cushions.

3. The dental water jet of claim 1, wherein the handle having a tip ejection switch which slides longitudinally along a portion of a length of the handle.

4. The dental water jet of claim 3, wherein the tip ejection switch comprises a slide switch portion and a latch portion, wherein the latch portion engages the tip and prevents it from disconnecting from the pump system.

5. The dental water jet of claim 4, wherein the removable tip includes a retention groove which engages an engagement tab defining an aperture in the latch portion.

6. The dental water jet of claim 1, wherein the tip engages a spring loaded ejection unit.

7. The dental water jet of claim 6, wherein a proximal portion of the tip passes through an O-ring sealing the tip into the fluidly connected system.

8. The dental water jet of claim 7, wherein the ejection unit biases the tip into a latch portion which engages a groove on the tip such that in response to the latch portion being moved transversely out of the groove, the ejection unit forces the tip out of the handle.

9. The dental water jet of claim 8, wherein the proximal end of the tip includes a plurality of flat sides which engage a plurality of flat surfaces on the handle preventing the tip from rotating.

10. The dental water jet of claim 1, wherein the tube is supported by a plurality of hose retention brackets.

11. The dental water jet of claim 1, wherein the pump system is powered by a power cord supported by a strain relief wall which forms a 180 degree bend in the power cord.

12. The dental water jet of claim 1, wherein:
    the first gear is a helical gear attached to the motor; and
    the second gear is a helical gear engaged with the first helical gear and engaged with the piston such that the motor drives the piston through the helical gears.

13. The dental water jet of claim 1, further comprising elastomer support cushions each including a flat surface parallel with the bottom of the base housing and having annular walls which extend from the flat surface.

14. The dental water jet of claim 1, wherein the fluid reservoir comprises an elliptical step which nests with an elliptical step located on the top exterior of the base housing.

15. The dental water jet of claim 1, wherein:
    the base housing includes a first aperture on an outside surface and a second aperture in a bottom surface;
    the first aperture receives a power cord; and
    the power cord is restrained by a zip tie that passes through the second aperture and around the power cord.

16. The dental water jet of claim 1, wherein the drain hole is defined within a recessed portion of the bottom of the gear housing.

17. The dental water jet of claim 16, wherein the drain hole is formed as part of a depression to direct liquids from the bottom of the gear housing into the drain hole.

18. The dental water jet of claim 1, wherein the gear housing is attached to a bottom shelf of the base housing.

19. The dental water jet of claim 18, wherein the bottom shelf is a recessed portion of a bottom surface of the base housing.

20. The dental water jet of claim 1, wherein the gear housing includes an aperture defined through the side wall and through which the piston passes.

21. The dental water jet of claim 20, wherein the piston moves within a piston housing, the piston housing extending through the aperture defined through the side wall of the gear housing.

22. The dental water jet of claim 1, wherein the second gear drives the piston through a connecting rod, the connecting rod positioned at least partially between the second gear and the top wall of the gear housing.

23. The dental water jet of claim 1, wherein the top wall of the gear housing is defined by the bottom wall of the base housing.

24. The dental water jet of claim 1, wherein the gear housing defines an exterior surface of the base housing.

25. The dental water jet of claim 1, wherein the first and second gears are positioned below the bottom wall of the base housing.

* * * * *